US006787344B2

(12) United States Patent
Beasley et al.

(10) Patent No.: US 6,787,344 B2
(45) Date of Patent: Sep. 7, 2004

(54) ISOLATED HUMAN ENZYME PROTEINS, NUCLEIC ACID MOLECULES ENCODING HUMAN ENZYME PROTEINS, AND USES THEREOF

(75) Inventors: Ellen M. Beasley, Darnestown, MD (US); Gennady V. Merkulov, Germantown, MD (US); Valentina Di Francesco, Rockville, MD (US)

(73) Assignee: Applera Corporation, Norwalk, CT (US)

( * ) Notice: Subject to any disclaimer, the term of this patent is extended or adjusted under 35 U.S.C. 154(b) by 8 days.

(21) Appl. No.: 10/369,626

(22) Filed: Feb. 21, 2003

(65) Prior Publication Data

US 2003/0143624 A1 Jul. 31, 2003

Related U.S. Application Data

(62) Division of application No. 09/820,924, filed on Mar. 30, 2001, now Pat. No. 6,555,351.

(51) Int. Cl.$^7$ ............................. C12N 9/10; C12N 1/20; C12N 15/00; C12N 5/00; C07K 1/00

(52) U.S. Cl. .................... 435/193; 530/350; 435/252.3; 435/325; 435/320.1; 435/6

(58) Field of Search .......................... 530/350; 435/193, 435/320.1, 325, 252.3, 6

(56) References Cited

PUBLICATIONS

Rotig et al. "Widespread Coenzyme Q10 Deficient in Familial Mitochondrial Encephalomyopathy." Nov. 1, 1999. Database SPTREMBL. Accession No. Q9Y2W5.
International Search report dated Jul. 24, 2003.
Results of BLAST search of SEQ ID No. 2 against Derwent (FastAlert and GeneSeqP) and NCBI (pataa) protein patent databases on Jul. 23, 2003.

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the enzyme peptides of the present invention. The present invention specifically provides isolated peptide and nucleic acid molecules, methods of identifying orthologs and paralogs of the enzyme peptides, and methods of identifying modulators of the enzyme peptides.

16 Claims, 25 Drawing Sheets

```
   1 CTCCGCACGC CCCTGCCCCG TCGCCTCCCG GGAGCGGCTG CAGTCCCCGT
  51 TGGCTGCAGA CGGGCAGACA CCCGAAGTGT CCGCGCCGGC AGCCGGACCG
 101 CAAGCGATGA ATATCGAACC GCGCTCCCGG GCCTGGCCGA AGCGCTTCCT
 151 GTGCCAGGTT TCCGGCTCCG GGTCCCGGGA GGAGGATCGC GGGCCATTAT
 201 GCGGAGCCGC CGCCCTGCCG CGACTTTCAG ACTCCGACCA TGGCCTCGCG
 251 CTGGTGGCGG AGGCGGCGCG GCTGCTCCTG GAAGCCGGCG GCGCGGAGCC
 301 CCGGGCCCGG CTCCCCCGGC CGTGCGGGAC CGTTGGGGCC GATCGCCGCT
 351 GCCGATATTC CGCGCGCAGG TTCATAGGCG AAGGGACTT GACTTGTCTC
 401 AGATACCCTA TATTAATCTT GTGAAGCATT TAACATCTGC CTGTCCAAAT
 451 GTATGTCGTA TATCACGGTT TCATCACACA ACCCCAGACA GTAAAACACA
 501 CAGTGGTGAA AAATACACCG ATCCTTTCAA ACTCGGTTGG AGAGACTTGA
 551 AAGGTCTGTA TGAGGACATT AGAAAGGAAC TGCTTATATC AACATCAGAA
 601 CTTAAGGAAA TGTCTGAGTA CTACTTTGAT GGGAAAGGGA AAGCCTTTCG
 651 ACCAATTATT GTGGCGCTAA TGGCCCGAGC ATGCAATATT CATCATAACA
 701 ACTCCCGACA TGTGCAAGCC AGCCAGCGCG CCATAGCCTT AATTGCAGAA
 751 ATGATCCACA CTGCTAGTCT GGTTCACGAT GACGTTATTG ACGATGCAAG
 801 TTCTCGAAGA GGAAAACACA CAGTTAATAA GATCTGGGGT GAAAAGAAGG
 851 CTGTTCTTGC TGGAGATTTA ATTCTTTCTG CAGCATCTAT AGCTCTGGCA
 901 CGAATTGGAA ATACAACTGT TATATCTATT TTAACCCAAG TTATTGAAGA
 951 TTTGGTGCGT GGTGAATTTC TTCAGCTCGG GTCAAAAGAA AATGAGAATG
1001 AAAGATTTGC ACACTACCTT GAGAAGACAT TCAAGAAGAC CGCCAGCCTG
1051 ATAGCCAACA GTTGTAAAGC AGTCTCTGTT CTAGGATGTC CCGACCCAGT
1101 GGTGCATGAG ATCGCCTATC AGTACGGAAA AAATGTAGGA ATAGCTTTTC
1151 AGCTAATAGA TGATGTATTG GACTTCACCT CGTGTTCTGA CCAGATGGGC
1201 AAACCAACAT CAGCTGATCT GAAGCTCGGG TTAGCCACTG GTCCTGTCCT
1251 GTTTGCCTGT CAGCAGGTAG GTTTTACAAA CTCCCTTTGA CACATCACTG
1301 CATAGCCCCA CAGAACTGAT GTCCCGCGGC ACAGCTGATG GGAAGATTGC
1351 ATAAAGGAAT AGATGGGAAG GCATTCAGAT AAGAGATCAC AGGTCTGCAT
1401 TTGATCCTGG CTGAGTGAGA TGTTGGGGCT GGTCATTTCA CCTTGCTAAG
1451 ACTGTTTCCT TATCTGTAAA ATTGAGAAGA TCACCTTTCT CCCAGGGTGG
1501 TTGTGAGGAT TAGCTAAGAT CCTATTTGAG ATCTTTGTGT CTTGTGGTGT
1551 GCCATAGGCA TTTGAGGTAG CATCGTGATT ATTTCCATAT ATTTTGGCCA
1601 CTGGCAAAGT GAACGGTTTC TAAGGTTCTA TTATAGGACT GGACTTTGGT
1651 GGTCCTCAGA GCCCCTTAAA AGGCATAGGA AGCATCAAGG GCTCCAAGC
1701 ATAAGAAATT CTCCGGTTCT AGAAGTTTAA TGAGACTCTG CTGCTCTGAG
1751 AGAGGCTTTA GAACCTCGGC CATTGCCTCA AAATGTCAGG AAGTCAGTGG
1801 AGTGCAGTAG ACCCACATAG TTCCTTCTTT CTCCGGATTG AGGGACTGAG
1851 TCCCCCTTAA TGTGAATGAA AGGCTTAGGA AGCTTCAAAG ATGTTCCCTC
1901 GACTGACAAA GCAGACATTC TCACAGCCTC CTCCAGACCC TGCCACATGG
1951 CTTGTGGCTG TACTGAATGT TACTTGAAAT AAGTGAGACA TTAGCTGGTG
2001 TTGGAACATC TCGTTAATAG ATTTTCATCT TAGTAGTATT TAATTTGTTA
2051 TGTTGCAAAG CAGTAAGATG TTCATCACCG TGCCATGAAA TTCAACATTA
2101 GCTCTTTGGT GTAAAATTAT AGTAACTTTT GGTCTTTCAG AGATTTTGCC
2151 TCTATTCTGT CTTCACGTTT ACAAAGGTCA GTCATGTCCT CCATAAAATT
2201 CAGTGATTCC ACTGTGATAC AGAAACCACG GCCCTTGCTT TTGGTGGGTT
2251 TCTGATTGGA GAGAGGAAAG GTCATCTTTC ACCCACTATC TAGCATAGCC
2301 ATTGGCAGCA TGATTCTTCC CAGGGGAGGC TGACGTTCTG GGTGGCTGGA
2351 CCAGGCTACT TTGGCAGCTT GCTAAGGCTA TGAATGGAGA TGTTGGGGTA
2401 CTCGGTAGGA ACACCCGCCC TCATTATTAC AAGGCTTCCA TCCTCTCAAA
2451 CTTTGGAGGC TGAGGTAAGA AGTGAAAGGT ATGCTGTAAA TAGGTCCTCT
2501 CTCCCAATGA GGCTTACTTG CCAGCCCAAA ATCAAAGAGT ATAATACATG
2551 TGCCCAGTTT TGACAAAAAT TTATAAAACC TCCTTTTGTA CATTAAGGCA
2601 AGAGTGAGGA ACATTTGAGC CATGTAGGTG TTATGCTGGG GATTAGAAAA
2651 ATGAGGCACT GGCTACCAGT AACCTATATA ACTGCGAACA TTACTTCTCA
2701 GATACTTGTT AGTAAACATG AGTGAAGGAA AGCAAGATGG ACTGAGTGTG
2751 CTGAAATCCA GCTAGCTTGG TAAAGATTCC TTTACCTAGG CTCAGATTAT
2801 CAGGATAAAA GGAAAAAGCC TTTTTCCCTG GAGAAGTCTA TGAGAAAGTT
2851 TTGGTTGCTC TATTTGTAAA AATCTTCAAA TTGTTAAGTA CTTGTTATGA
2901 ACCCCAGGAT ACTAAGTTAC CGGTTGAGTC CTACTTAAAC CTTAAGGTGA
2951 CTGGGTGAGA GGAGGCTGGC CTCTTCGGAC TGTGTTTCAC TCTGAATATA
3001 TTTCAGAAGA AACTAACTTA CTTTCCCCTA CACACACAAA GGAGTAATGG
3051 CTATCTCTGC TTTCATATAT AGTGGGGGAA AGGGGAAATG GACCTCTGCA
3101 TAGTATCTGT CAGTAATCTA CAAGAGACTG AAAAATGCTG GTTAGGCGGT
3151 GGCTCATGCC TGTAATCCCA GCACTTTGGG AGGCTGAGGC AGTTGGATTA
3201 TGAGGTCAGG AGTTCAAGAC CAGCCTGACC AATATGGTGG AAACCCCGTC
3251 TCTACTAAAA ATACAAAAAT TAGCCGGGCC TGGTGGTGCA TGCCTGTAAT
3301 CCCAGCTACT CGGGAGGCCA AGGAAGGAGA ATCCTTGAAC CTGGGAGGCA
3351 GAGGTTGCAG TGAGCCGAGA CTGCACTCCA GCCTGGGTGA CAGAGTGAGA
3401 CTCCGTCTCA AAAAAAAAAA AAAAAAAAAA AAA
(SEQ ID NO: 1)
```

FEATURES:
5'UTR:       1 - 198
Start Codon: 199
Stop Codon:  1288
3'UTR:       1291

FIGURE 1A

Homologous proteins:
Top 10 BLAST Hits

```
                                                              Score     E
Sequences producing significant alignments:                   (bits)  value
CRA|18000005225619 /altid=gi|7657653 /def=ref|NP_055132.1| tran...  578   e-163
CRA|18000005219502 /altid=gi|9507201 /def=ref|NP_062374.1| tran...  490   e-137
CRA|98000043619170 /altid=gi|12848965 /def=dbj|BAB28153.1| (AK0...  359   1e-97
CRA|89000000203428 /altid=gi|7302032 /def=gb|AAF57135.1| (AE003... 294   3e-78
CRA|154000124062378 /altid=gi|12055493 /def=emb|CAC20852.1| (AJ... 217   7e-55
CRA|18000005058296 /altid=gi|1703631 /def=gb|AAB37678.1| (U8044... 210   1e-52
CRA|18000005069761 /altid=gi|7447582 /def=pir||JC5429 di-trans,... 208   3e-52
CRA|335001098640701 /altid=gi|11279237 /def=pir||T43193 trans-p.. 207   6e-52
CRA|335001098678167 /altid=gi|11322965 /def=emb|CAC16849.1| (Y1.. 206   1e-51
CRA|335001098678171 /altid=gi|11322972 /def=emb|CAC16851.1| (AJ.. 202   3e-50
```

EST:

```
                                                              Score     E
Sequences producing significant alignments:                   (bits)  value
gi|12902640 /dataset=dbest /taxon=960...                       1766   0.0
gi|12907677 /dataset=dbest /taxon=960...                       1709   0.0
gi|12780065 /dataset=dbest /taxon=960...                       1340   0.0
gi|12385033 /dataset=dbest /taxon=96...                        1207   0.0
gi|12762180 /dataset=dbest /taxon=960...                        884   0.0
gi|12950123 /dataset=dbest /taxon=960...                        835   0.0
gi|6894771  /dataset=dbest /taxon=9606...                       537   e-150
gi|10082349 /dataset=dbest /taxon=960...                        488   e-135
gi|10082361 /dataset=dbest /taxon=960...                        454   e-125
gi|10082359 /dataset=dbest /taxon=960...                        454   e-125
```

EXPRESSION INFORMATION FOR MODULATORY USE:
```
gi|12902640   T cells from T cell leukemia
gi|12907677   B cells from Burkitt lymphoma
gi|12780065   neuroblastoma cells
gi|12385033   duodenal adenocarcinoma, cell line
gi|12762180   adenocarcinoma, cell line
gi|12950123   B cells from Burkitt lymphoma
gi|6894771    stomach
gi|10082349   breast
gi|10082361   breast
gi|10082359   breast
```

Tissue expression:
whole liver

FIGURE 1B

```
  1 MRSRRPAATF RLRPWPRAGG GGGAAAPGSR RRGAPGPAPP AVRDRWGRSP
 51 LPIFRAQVHR RKGLDLSQIP YINLVKHLTS ACPNVCRISR FHHTTPDSKT
101 HSGEKYTDPF KLGWRDLKGL YEDIRKELLI STSELKEMSE YYFDGKGKAF
151 RPIIVALMAR ACNIHHNNSR HVQASQRAIA LIAEMIHTAS LVHDDVIDDA
201 SSRRGKHTVN KIWGEKKAVL AGDLILSAAS IALARIGNTT VISILTQVIE
251 DLVRGEFLQL GSKENENERF AHYLEKTFKK TASLIANSCK AVSVLGCPDP
301 VVHEIAYQYG KNVGIAFQLI DDVLDFTSCS DQMGKPTSAD LKLGLATGPV
351 LFACQQVGFT NSL
(SEQ ID NO: 2)
```

FEATURES:
Functional domains and key regions:
[1] PDOC00001 PS00001 ASN_GLYCOSYLATION
N-glycosylation site Number of matches: 2
    1    172-175 NNSR
    2    243-246 NTTV

---

[2] PDOC00005 PS00005 PKC_PHOSPHO_SITE
Protein kinase C phosphorylation site

Number of matches: 8
    1    8-10 SRR
    2    34-36 SRR
    3    207-209 SRR
    4    14-16 TFR
    5    8-10 SRR
    6    34-36 SRR
    7    207-209 SRR
    8    180-182 SQR

---

[3] PDOC00006 PS00006 CK2_PHOSPHO_SITE
Casein kinase II phosphorylation site

Number of matches: 4
    1    99-102 TTPD
    2    136-139 STSE
    3    333-336 SCSD
    4    342-345 TSAD

---

[4] PDOC00008 PS00008 MYRISTYL
N-myristoylation site

Number of matches: 5
    1    24-29 GGGGGA
    2    25-30 GGGGAA
    3    26-31 GGGAAA
    4    68-73 GLDLSQ
    5    266-271 GSKENE

---

[5] PDOC00407 PS00723 POLYPRENYL_SYNTHET_1
Polyprenyl synthetases signature 1

196-210 LVHDDVIDDASSRRG

---

[6] PDOC00407 PS00444 POLYPRENYL_SYNTHET_2
Polyprenyl synthetases signature 2

318-330 VGIAFQLIDDVLD

Membrane spanning structure and domains:

| Helix | Begin | End | Score | Certainty |
|---|---|---|---|---|
| 1 | 217 | 237 | 0.726 | Putative |
| 2 | 343 | 363 | 0.957 | Putative |

FIGURE 2A

BLAST Alignment to Top Hit:
>CRA|18000005225619 /altid=gi|7657653 /def=ref|NP_055132.1|
    trans-prenyltransferase; polyprenyl pyrophosphate
    synthetase [Homo sapiens] /org=Homo sapiens /taxon=9606
    /dataset=nraa /length=376
        Length = 376

Score = 578 bits (1474), Expect = e-163
Identities = 288/308 (93%), Positives = 294/308 (94%)
Frame = +1

```
Query:  364  AQVHRRKGLDLSQIPYINLVKHLTSACPNVCRISRFHHTTPDSKTHSGEKYTDPFKLGWR  543
             AQ HR+KGLDLSQIPY NLVKHLT ACPNV  IS+FHHTTP SKTHSGEKYTDPFKLGWR
Sbjct:    3  AQAHRQKGLDLSQIPYFNLVKHLTPACPNVYSISQFHHTTPYSKTHSGEKYTDPFKLGWR   62

Query:  544  DLKGLYEDIRKELLISTSELKEMSEYYFDGKGKAFRPIIVALMARACNIHHNNSRHVQAS  723
             DLKGLYE IRKE LIST+ELKE+SEYYFD KGKAFRPIIV LMARACNIHHNNSRHVQAS
Sbjct:   63  DLKGLYEGIRKEPLISTTELKEISEYYFDVKGKAFRPIIVVLMARACNIHHNNSRHVQAS  122

Query:  724  QRAIALIAEMIHTASLVHDDVIDDASSRRGKHTVNKIWGEKKAVLAGDLILSAASIALAR  903
             QRAIALIAEMIHTASLVHDDVIDDASSRRGKHTVNKIWGEKKAVLAGDLILSAASIALAR
Sbjct:  123  QRAIALIAEMIHTASLVHDDVIDDASSRRGKHTVNKIWGEKKAVLAGDLILSAASIALAR  182

Query:  904  IGNTTVISILTQVIEDLVRGEFLQLGSKENENERFAHYLEKTFKKTASLIANSCKAVSVL 1083
             IGNTTVISILTQVIEDLVRGEFLQLGSKENENERFAHYLEKTFKKTASLIANSCKAVSVL
Sbjct:  183  IGNTTVISILTQVIEDLVRGEFLQLGSKENENERFAHYLEKTFKKTASLIANSCKAVSVL  242

Query: 1084  GCPDPVVHEIAYQYGKNVGIAFQLIDDVLDFTSCSDQMGKPTSADLKLGLATGPVLFACQ 1263
             GCPDPVVHEIAYQYGKNVGIAFQLIDDVLDFTSCSDQMGKPTSADLKLGLATGPVLFACQ
Sbjct:  243  GCPDPVVHEIAYQYGKNVGIAFQLIDDVLDFTSCSDQMGKPTSADLKLGLATGPVLFACQ  302

Query: 1264  QVGFTNSL 1287
             Q   N++
Sbjct:  303  QFPEMNAM  310  (SEQ ID NO: 4)
```

Hmmer search results (Pfam):
Scores for sequence family classification (score includes all domains):
Model       Description                                    Score    E-value    N
--------    -----------                                    -----    -------    ---
PF00348     Polyprenyl synthetases                         167.7    2e-46      1

Parsed for domains:
Model       Domain   seq-f   seq-t     hmm-f   hmm-t      score    E-value
--------    ------   -----   -----     -----   -----      -----    -------
PF00348     1/1      134     353 ..     1       241 [.    167.7    2e-46

FIGURE 2B

```
   1 CATCAATATG GCAAGAAAAT GTCTTGGAGG GTACCTAACA CTCCAACCTC
  51 AAAACGACAA CCTTGATCGC TTTCAGTTAC ACATAGGCCA TTTTGATCCA
 101 TCTGTACTGG CTCTTTTCAT TTGTCTAAGG GCAGCAAAAT AGACTAAAGT
 151 TGTTTTCAGA CTGCACAAGA GAAGTCTGTT CTTTAGCACT TACCTGCATA
 201 ACTCAGATAG TGTTTTTAAC TTCCTCAACT CATGCTTGGC CTAGTTGGGT
 251 CAAAAGAACT ACTTGTGAAT TCCGTATGTC CAATTGGTAG GTTACTGTTT
 301 TTTCTCAAGA GTTTAGCTAT ACAGTAATGT TGGAAGTCTT GAGGAACTTC
 351 AGCTGCTGTC CCTACTTAGC CTTGCAATAC TACGGCATCT TTTCTTCTTT
 401 TTCTTTTTTT TAAAGACGGA GTCTCACTTT GTCACCTAGG CCGAAGTGCA
 451 GTGGCACAAT CTCGGCTCAC TGCAACCTCT GCCTCCCAGG TTCAAGTGAT
 501 TCTCTTGCCT CAGCCTCCTA AGTAGTTGGG ATTACAGAAC ATGCACCACC
 551 ATGCCCAACT AATTTTTAAA TATTTAGTAG AGACGGGTTT CACCATGTTG
 601 GCCAGGCTGG TCTCAAACTC CTGACCTCAA GTGATCCACC TGCCTCGGCC
 651 TCCCACAGTG CTGGGATTAC AGGCTGAGCC ACTGTGCCCC CGACCTACAG
 701 CATCTTTTTA AGAGCAATGT TTTCTGTTTT AATGTGGCCA AGCAATCTCT
 751 AAACGAACAT GGTCTGACAA AATTGTGTAG TGACATACTT GACAACTGGG
 801 TGAGCTTGAG TGTGATACTT ATTTGACCAT ACGGTATTTC CTCTATATGT
 851 TTCCTTATCT TTATATACAA AAAAGGGCAA ATGATAATGT CTTAGTCATA
 901 GGATCAAGTA CAACCCAAGT GCTTACTGCT ACACTCTACT TGGCAAATTC
 951 CACCTTATGA ATGTTTCTTA ATATATAAAC CTAATCTAAA CCAAGATAAG
1001 CTACAGGTGC ATATTAACAA TCTTTACTCA TAAAGTTTTG CATATTTTTA
1051 CATACTATTC TTCAAGATGG AAAAAACACC ATCAAACTGG CTTATTTTCA
1101 TAGATGTCTT TATATAGTCT ATGATGTCTT CATTCCATAA AAAATCCACA
1151 CGATTAAATA TGAAATTAAT GTACCCAGCT ATGAGGCTAC CGCATTCTTT
1201 AACCCAAGAA CAAGAAAATA CATGAATCAG AGAACTGCAA TTACCTACTT
1251 GCTGGTCTAT TTCCTCATTA GAGTGAATTT TTTGAGGACT AAATTGCATT
1301 TCTCTATCTC TAATGCTTAT CCCCTATCTC ACTGGCTCTG TGTGTTTGAG
1351 TGCATGCGCT GAATGTTTAT ATCACTTAAT TTCTGTTCGG AACACGCTGT
1401 CTCTTAGCAC CAGTAGATCT GGCCTTAGAG CTAAGGAAAG AAGGCCTTTC
1451 TAACCCATAA GGGGTACTAA TCCTGTACAG ACTCCAATAT CTCCCGGGCT
1501 GGGTACACGC AGGTTCACAC CCAGGTGTGA GCAAGATTGC CAAACTATAC
1551 CTATAAGGCG TTTGGAGGAG AGAGTCCAAA AGTCACGAGA CCCGGCTAAT
1601 TTAGCTACTA TTTCACAACA ACCCTGATCG TGGTCGGACT TGTTTCTAGG
1651 AAGATGCGAT GGGCTGGAAC TTCCTTCAAG AACAGATTGC AAAAGGCAGC
1701 CGACCAGGGC GTGTCAGGTC ACTGCCAAGG GAAGCAGCAG CGGAAACCGT
1751 CGCCTCCGGC TTAGGCTGCG GAGCGGGAAC CCCATTCTCT GAGTTATGTT
1801 TCTGCCTAAA CACGCAGAAC AAAAGAGTTC GTGGCTGCAA GGGTGGCGCG
1851 CGGTAGTATT TCTTGCTAAT AAAAGGTCCC CACAGGGACA TTTTTGCTAT
1901 GACTGCAGGG GTGGCCAGTG CCCCTGCACA GCTTCCGGGA AGAGGTGGGG
1951 ATAGGAGGCT CGCCCCGGGG AAGGTCACGC TCGGGGTCCC CAGACCAGGT
2001 CTCCGCACGC CCCTGCCCCG TCGCCTCCCG GGAGCGGCTG CAGTCCCCGT
2051 TGGCTGCAGA CGGGCAGACA CCCGAAGTGT CCGCGCCGGC AGCCGGACCG
2101 CAAGCGAGGA AGAGCGAACC GCGCTCCCGG GCCTGGCCGA AGCGCTTCCT
2151 GTGCCAGGTT TCCGGCTCCG GGTCCCGGGA GGAGGATCGC GGGCCAGAGG
2201 CGGAGCCGCC GCCCTGCCGC GACTTTCAGA CTCCGACCAT GGCCTCGCGC
2251 TGGTGGCCGT GGCGGCGCCG CTGCTCCTGG AAGCCGGCGG CGCGGAGCCC
2301 CGGGCCCGGC TCCCCCGGCC GTGCGGGACC GTTGGGGCCG AGCGCCGCTG
2351 CCGAAGTCCG CGCGCAGGTG AGGTTGGGAG GCGCGCGCCC GGCGGGGCTC
2401 AGAGGTCACG GCTCCAATGA CAGCAGTGGG CGGAATGAAT GGGAGCGGGG
2451 AGCACGTGCG TCGCGACGTC GGGGCGCGCG GGGTAGCTCC GGGGTAGCTC
2501 CGGGGTGGGA CTCCGGAGCT GAGGGGTGCT CGCGGTGGGA CGGAGCCGCG
2551 CGTTGGACTG AAGTAGGGGC GCCCTACACG GGGTTGCAGA AAGCGGTGTC
2601 CTGGGGACCC CGGGAGCGTT TTGGGGGGTG GAGAAAGCGG TGGGATCCGT
2651 GTCCTGGGGG AAGCGCAGGA GCGATCAGAT TGACCGCTGC TATATGGACA
2701 AGGTTAATTA AGCCTGGAGA GCGACTGCAG CTATTTACTT TGGAGTTAGA
2751 GGAAGACAGA TCTTGCCTGA AATTTTAGAG CCAAAGTGCT CAGAGCTCTC
2801 TCCGAGAAAC GGAGGATCGA ATCGGCCTCG GAATAGTCCG AAAAGGTCTT
2851 GTGGAGAATG CAGGGCTGGT GCTAGGGTGG ACCGGACCTT AGTTGTCCAG
2901 CAGTGGCTTC GGGAGGAGAG CACACCTGGA TGGGGCTGGA ATGACACTGG
2951 AAGGAGAAAG GCCCGAGGCC GTCAGGAGGA GAGAAACCCT GGAGTCATCT
3001 AAAGTCAGAA TCTCAGTGAT AGCCCATTCT TTCAGGGTCT CCTCTGCTGC
3051 CTTTGGGTTC CGATCTCCTT TTTCTCCCTT TCTGGTCAGT TTAGCCCCTG
3101 TAAATGGACA CTGTGAGCCC TTCTGCACTT TGTAATGATT CTCAGTGTGC
3151 CATGGGGTAG GCCCATGCTA TTAGCATAAC CGTGCAAAAT CTATGGACTC
3201 ACTGTTACTT AAGTTTATTT GAATTTAGTA CTCTTTTAAT TCAGATTTGG
3251 TATACTTTAT GTGTCCGTGT TCTCATCAAA CATCATTTCC CAGTATGAAA
3301 TATATAACAC TTATAAATAT CTACTTTGTA CCAAAGTAGA TGCGTATCAC
3351 AAATTATCCA AAACAAGGCT TGGGCCAGGC ACAGTGGCTC ACACCTGTAA
3401 TCCCAGCACT TTGGGAGGCT GAGGTGGGAG AATCGGTTGA GGCCAGGAGT
3451 TTGGGACCAG CCTAGGCAAC ATAGCAAGAC TCTGTCTCTA TAAAAAATAG
3501 AAAAAATTCA CCAGGTGGGG TGGTGCATGC CTGTAGTTCT ACCTACTCAG
3551 GAGCCTGAGG GAGGAGGATT GTTCGATCCC AGGAGTTCAA GATTACAGTG
3601 AGCTGTTTAT TGTGATAGTG CCAGTGCACT CCAGCCTGGG CAACAGTGTG
3651 AGACCCTATC TCTAAAAAAT CTAAAGCAAA AAAGACGTTT GGAGACCAAG
3701 TGGCAGCTGG GCAACTGAGC AATGCTAGAG AGTAAAGAGA ACAGAATATG
3751 GGGGGTGAGG GGCACGTGGG AGAAGAGGCT TAGAGGAGGA AGGTAGGCTT
3801 TGCTGTGATC CATTTCAGGA CTGTTCTCTC CAGACTTCAG ATATTTCTAG
```

FIGURE 3A

```
3851 TTCCACAGAA GAAGCCAGTA TTTGAAGAGA TGGGTGCATC CACCCTCTTA
3901 TGCCACTACA TGCTTCTTCT TCTTCTTCTT TTTTTTTTTT TTTTGACACA
3951 GAGTCTCACT CTGTCGCCCA GGCTGGAGTG CAGTGGCGGA ATCTCGGCTC
4001 ACTGCAAACT CCACCTCCCA GGTTCAAGCG ATTCTCCTGC TGCAGACTCC
4051 CAAGTAGCTG GGATTACAGG CGTACACCAC GACCCCCAGC TAATTTTTGT
4101 ATTTTTAGTA GAGACAGCAT TTCACCATGT TGCCCAGGCT GGTCTGGAAC
4151 TCCTGACCTC AAGTGATCCA CCCCCTCCTC GGCCTCCCAA AGTGCGGGGA
4201 TTACAGGTGT GAGCCACCAC GCCTGGCCTG ACACTTCTTT TTAAAAAAGT
4251 TTCTTGCCCA CCAAGCAACC TTAGCCAGGG AAAGTGTGCT TTTCTGGAGA
4301 GAATATGCTT TATGGCCTCC CCGTCTGCAT GACGACAAGG AGGAATTCTG
4351 TGGACTCATG ATGCCAAGAT CATGTATTTC TGATGTGTGT GTCAGTGATG
4401 CCTTTCACTA TACGTTAATA TGTTAGCATT CTGGTGTCTG CCTCAGGCAT
4451 GTGTATTTTG GTTACTTCAA GTCTCTTAGG GCCTGATAGT CCTTGGGGAC
4501 ACAGAACTAC AATAACTAAG CCACAGGGAC AAAGAGCGGC AATAATTAAG
4551 CCACGTCTTG CTCTCCACCA GAGTTGTACAT ACCTCCTAAT GGTTGTACAT
4601 TCTTCTGACT TCACTAGTAG TGTGAACAAA TATTGTAATA CAATAAAAAC
4651 CAGTGTGCAT GTGATCGTGC CAAATCACTT CTCAATATAT CTTTGATTTT
4701 TTTTTTTAAT TTATTTTTTT AGAGACGGGG ACTTTTTGTG TTGGCCAGGT
4751 TGGTCTTGAA CTCTTGGACT CAAGCCATTC CCCCCTCCCC CCCACCCCGC
4801 TTGAGGATTG GCACACGGCC ATGTATTTGA TTCTTACCCA GCACTTTCTC
4851 TTTAGCTGAG CGTGGTGGCT CACGCCTGTA ATCCCAACAG TTTGGGAGGC
4901 CGAGGCAGGA GAATCCCTTT AGCTCAGGAG TTCGAGACCA GCCTGGGCCA
4951 CTTAGTGAGA CCTCCTGATA CGGTTTGGCT CTGTATGCCC ACCCACATCT
5001 ATCTCGAACT GTAATCCCCA ATTACATTTG GGGACCAGGG AGGGTCAAGG
5051 GAGGGACCAG GTGGAGGTAA TTGGATCATG GGGGTGGATT CCCCCATGCT
5101 GTTCTCATGA TAGGGAGTTC TCACAAGATC TGCTGGTTTT ATAAGTGTTT
5151 GGTAGTTCCT CCTGTGTTCA TTCTGTCTCC TGCCGCCTTG TGAAGAAGGT
5201 GCTTGTTTCT CCTTCTCCTT CTTCTGAGGT GATTCTAAGT TTCTGAGGCC
5251 TCCCCAGCCA TTCAGAACTG TGAGTCAATT AAACCTCTTT CCTATAATTA
5301 TAAATTGCCC AGTCATGGGT AATTTCTTTA TAGCAGTGTG AGAATGGACC
5351 AATACAGATA ATTGGTACCA AAGTAGTTGG CATTGATATA AGATACCTGA
5401 GAATGTGGAA ATTACTTTGG AACTGGGTAA CAAGCAGAGG TTGGAATAGT
5451 TTGGAGGGCT CAGAAGAACA AAGGAAGATG TAGGAAAGTT TGGAAATTCC
5501 TAGAGTCTTG TTGAATGGCT TTGACCAAAA TGCTGAAAGT GATATGGATG
5551 ATGAAGTCCA GGCTGAGGTG GTCTCAGATG GAGATGAGGA GCTTCCTGGG
5601 AACTGGGCAA AGGTCACTCT TGCTATGCTT TAGCAAAGAG ACTGGTGGCA
5651 TTTTGCCCCA CCCTAGAGAT CTGTGGAACT TTGAGCCTGA GAGAGATGAT
5701 CTGAAATTGG AACTTAAATT TAAAGGGGAA GCAGAGCATA AACGTTTGGA
5751 AAATTTGCAG CCTGAAGATG TGATAGAAAA GAATTTTCTG GGGAGGAATT
5801 CAAGCTGGCT GCAGACATTT GCATAAGTAA CAAGGAGCCG AATGTTAATA
5851 GCCAAGAGAA TGGGGAAAAT GTCTCCAGAG CATGTCAGAG ACCTTCTCTG
5901 CAGCCCCTCC CATCACAGGC CAGGAGGCCT AGGAGGGAAA AATGGATTCA
5951 TGGGCTGGGC CCAGGGCCCT GCTGCTCTGT GCAAGAGCAG CCTTGGGACT
6001 TGGTGCCCTG CTTCCCAGCC GTAGCTAAAA GGGGCCAAGG TACAGCTTGG
6051 GCCATTGCTT CAGAGGGTAT AAGCCCCAAG CCTTGGTGGC TTCCATGTGC
6101 TGCTGAGCCT GCAAGGTGCA CAGAAGACAA CAATTTGGGA ACTTCTGCCT
6151 AGATTTCAGA GGATGTATGG AAATGCCTCA ATGCCCAGGC AGAAGTCTGC
6201 TGAAGGGGGG AGAACCCTCA TGGAGAACCT CTGTTAGGAC AGTGCAGAAA
6251 GGAAATGTGG GGTTGCAGCC CCCACACGGA GTCCCTGCTG GGGCACTGCC
6301 TAATGGAGCT GTGAAAGGAG GGCCACCGTG CTCTAGACCC CAGAATGGTA
6351 GGTCCACCAA CAGCTTCCAC CGTGCACCTG GAAAAGCTGC AGGCACTCAA
6401 TGCCAGCCCA TGAAAATAGC AGTGGGGGTT GAACCCTGCA AAGCCACAGA
6451 GGCAGAGCCA CCCAAGTTCT TGGGAGCCCA CCCTTTGCAT CAGTGTGACC
6501 TAGATGTGAG ACATGGAGTC AAAGATCATT TTGGAGCTTT AAGTAATGAC
6551 TGCCCTGCTG GGTTTGGACT TGCATGAGGC CTGTAAGCCC CTTCGTTTTG
6601 GCCAATTTCT ACCATTTGGA ATGGGAACAT TTAACCAATG CCTGTACCCC
6651 CATTGTATCT TGGATGTAAC TAACTTGTTT TTGATTTTAC AGGTTCATAG
6701 GCGGAAGGGA CTTGACTTGT CTCAGGTAAG ACTTTGGACT TGGACTTTTG
6751 AGTTAATGCT AGAATGAGTT AAGACTTTTG AGGACTGTTC GGAAGGAATG
6801 ATTGGTTTTG AAAAATGAGG ATATGAGATT TGGGAGGAGC AAGGGGCAGA
6851 ACGATATGGT TGGTTCTGTG TCTCTACCCA AATCTCATCT CAAATTTTAA
6901 TCCCCATGTG TCAAAGGAGG GCCTATGTGG AGGTAATTGG ATCCTGGGGG
6951 CAGATTCCCC CATGCTGTTC TTGTTATAGC GAATTCTTAT GAGATCTGAT
7001 GGTTTTATAA GTGATTGGTA GTTCCTTCTG TGTTCTTTCT CCTTCTTGCT
7051 GCCTAGTGAA GAAGGTGCCT TGCTTTCCCT TTTCCTTCTG CCATGATTGT
7101 AAGTTTCTTG AGGCCTCCCT AGCCGTTTGG AACTGTGAGT CAGTTACACC
7151 TCTTTCTTTT ATAAATTACC CAGTCTTGGG TATTTCTTTA TAGCAATGTG
7201 AAAACGTACT AATACACCTC GTTTCTAAAA ATCAGCTACG CATTGTGGCA
7251 TGTTCCTGTA GTCCCAGCTA CTCAGTAGGC TGAGGTGGGA AGATAGCTTG
7301 AGCCCAGGAG ATTGAGGCTG CAGTGAGCTA TGATTGCACC ACTGCACTCC
7351 AGCCTGGAAA AATAAAATAA AAGTAAATTC ATGAGAGGCA AGGTTGACTT
7401 TCAGAGAGTG TGTGAGGGAA AGGTAAGAAA CAAAATCGGA ATTAGAAAAT
7451 GACTGTTGCC CCTCTCTTTT CATTCTTCAC TGCTTTTCTG AGCACCTCTC
7501 ACCTCCCTTT GAAAAACTGC TCTAAAGTAC TTTTAAAGCA GAAAATAGTA
7551 GCTTGATTGA ATAGATACTG TATTAAATGT ATATTGTGTA CCAGGCTCTG
7601 AGCTAAGAGC TTTACATCTG CTCTCTAAAT TAATCTCCAC CTCTCTCCAT
7651 GAGTAGGTAT TATCAGAAAG ACATCACAAG GTAACACAAA TGTTGAGATT
```

FIGURE 3B

```
7701 TGAACCGAGA TCTGTCTTCC AAAGTCCATG CTACTAATAA TTGTTAGGCC
7751 ACTTGGTGGT AAAAAGCGTC CCCTGTATTA ATTAGCTGTG TAATTTTAAT
7801 CCTTCAACCC AGATTAGGGG TCTATAACTG AATAACCAAA AAGTTATTCA
7851 GTTAGAATAG TTCAGTTAGT TATTAACTAA TCATAGTTAT TTGGTCAAGC
7901 GCAGTGACTC ACGTCTGTAA TTCCAGCACT TGGGGAGGCT GTGGCAGGAG
7951 GATTTCTAAT AATAGTAACT ATTACTAGAG ACCTGATAAT AATTATTAAG
8001 TCTCTTACTG AAGAAGTTTT ACTCTTCCAT TAAGATGCCC TTATTTATAA
8051 GTATTATAAT AAAATACTGA ACTCATATGA ATTAATTACC CATGTAGACT
8101 GAAAGACATA GGTTGTCATA TAATGGTTGT CATATAAAGC ATGAAGGAGG
8151 ATTGTCACTT TGTTTTCTTG TTGCACTGTA ATTGCCTGGG ATATCATGAA
8201 AGTTCTTACT GGTTTAATGA ATATGTAATG CTGTGGGGGA AAGAATGAAA
8251 CTCAGGCCAA CTACTTTGAC TGGTGTCTGG CAAAGTCAAC TTTCATTGCC
8301 ATTTTAATAT GGCGCCGGGC GCGGTGGCTC ACGCCTGTAA TCCCAGCACT
8351 TTGGGAGGCC AAGGCGGGCG GATCATGAGG TCAGGAGATC GAGACCATCC
8401 TGGCTAACAC GGTGAAACCC CATCTCTACT AAAAATACAA AAAATTAGCC
8451 AGGCGAGGTG GTGGGCGCCT GTAGTCCCAG CTACTCAGGA GGCTGAGACA
8501 GGAGAATGGC GTGAACCCTG GGGGGCGGAG CCTGCAGTGA GCCGAGATAG
8551 CGCCACTGCA CTCCAGCCTG GACGACAGAA CGAGACTCCG TCTCACAAAA
8601 AAAAAAAAAA AAAATATGG CTAGAGCAAT ACATGTTCAT TAGAGAAGAA
8651 TCAGAAAATA TCTACCAAAA GAAGGAATAA AACAAAACAC CCCCACAATC
8701 CGATTCATTC CAGAATAACT ACTTTTAACA CCCTGGTTTG TGTGCTTTCA
8751 AACTCTGTTC TCCCATTTCC AAAGGATGTT GAGGAACACG AACTTAAAAT
8801 AGACAGTGTT TGTATAAATA TAAATTCCTT CCTTGCTATT GAAATCTTTT
8851 TTCCTCTGAC CAATCTTAGT TAAATGGAAG GAAATTGTTT TAAAACTAAT
8901 TTTCAGGTCT GGAAAGATAG ATATGAATAT GGAAATGACT TTCTTTGGGG
8951 GAAGGGATGG ACTGAAGATG GTTATTATTT TCTCCTTTTT TCTTATTTAT
9001 GTTTTCTGCA ATGACAAGTA TTTTGTAATA ACAAAAGGAA ACTTTAAAAT
9051 TATTCTTCCT CTAAAGTTTG CAATCTACCT GTAAATGGGT GATTAGAAGA
9101 TAAAGATTAT AATTATGGGG GTTTTATCAT CCAATGTTAC AGTTTTTCAG
9151 GAATATTCTT ACAAGTTTCT TGACATTTTT ATTTTATAGA TACCCTATAT
9201 TAATCTTGTG AAGCATTTAA CATCTGCCTG TCCAAATGTA TGTCGTATAT
9251 CACGGTAAGT TTACAGTCCA TACTGCAACT ACTAAAATTA TCCATTTTTA
9301 AATTTATTAT TGTTTAAAAA ATTTTTTTTG TAGCGATGGG GAGCTCACTG
9351 TGTTGCCCAG GCTGGTCTTG AACTGCTGGC CTCAAGCTAT CCTCCCACCC
9401 TCAGGTTCCC AAAGTGCTGG GATTGCAGAC ATAAGCACCC GGCCTAAAAT
9451 TATTAATTAT ATTGCCTGTA AATTTCTATT CTAAATTGTA GATCTCTGCC
9501 TATTCAAAAA ACAGGAATAT AATAAAGTTT GAGCTCAACC CAGAGCACAA
9551 TGAACATAGT TTAGTTTTTC TTTGATTTTG TGGGTTCTCA AGGCCCTATT
9601 TATAAAAGTG ATCTATTGAT CTGTCATTTA GCAAGAATAG AATTCTGTAT
9651 GTTTTTCCAA ATTATAATGA CCTTTTCAGA TTCATGATTA ATTTCTAGCA
9701 AATATTTGGG CTGAATTTTC CGTATCTGAG TCTACTAAAT ATATATGTAT
9751 ATAAAACTTA CTTGAAAATG AAGTCATGTG CATTTTTGCA TGTCCCAGGT
9801 TTCATCACAC AACCCCAGAC AGTAAAACAC ACAGTGGTGA AAATACACC
9851 GATCCTTTCA AACTCGGTTG GAGAGACTTG AAAGGTCTGT ATGAGGACAT
9901 TAGAAAGGTG AGTTTTTTAT TCTGCTGTGA TGTAATGTTT TAGCTTACCA
9951 AAACTTACTA AAATTTTATT TTATTTTTA TTCTTATAAT TATTTATTATT
10001 TTTTGAGCTG GAGTCTCACT CTGTTGCCCA GGCTGGAGTGCA CAGCGGTGCA
10051 ATCTAAGCTC ACTGCAACCC TTGCCTCCCA GGTTCATGCA ATTCTCCTGC
10101 CTCAGCCTCC TGAGTAGCTG AGATTATAGG CATGCGCCAT CACACCTGGG
10151 TAATTTTTGT ATTTTTAGTG AAGACGGGGT TTTGCTATGT TGGCCAGGCT
10201 GGTCTTGAAC TCCTGACCTC AGGTGACCTA CCCGCCTTGG CCTCCCAAAG
10251 TGCTGGGATT ACAAAAAAAC AGTGCAGGTT TTCAGATCTG TACAATGCAG
10301 TTTGCAATCT TGATTCACGT ATGGTCAAGT TTCAAATGTT TCTTGAGAAG
10351 AATACATATG ACCCAGTGCC AGGCAATATG AAGAATGCAA TATGTATTTA
10401 TGTCCAGAAA GAGGTTATGG CAGGGTTGGG AACCTGAAGG AAAAAAATGG
10451 TCCAGGTGAC TCATGTTTGT CCAATGAGTT ATCCCACCTT TCCTCTTAAA
10501 ACCCACCACC TCCCAGTGAC TCCAGCTGTC TCTTCCTTAT CTAATTCTGA
10551 ATGTCATTGC CAGTGTGCCC CAAATATGGC TTTCTTCATT CAACTCTTTT
10601 TCCTGAAAAC TTTCAGTAGT TCCCAACCTC ACGTGGTTGG GCACCGTGGC
10651 TCGTGCCTGT AATCCCACCA ATTTAGGAGG CCAAAGCAAG AGGACTGCTT
10701 AAGCCCAGGA GTTTGAGGCT GCAGTGAGCC ATGATCCCGC CATTGCACTC
10751 CAGCCTGAGT GAGAGAGCAA GACATTTTTT CTGTCTTTAG AAAAAAATTG
10801 GCTGGGCACG GTGGATCACA CCTATAATCC TAGCACTTTG AGAGGACACC
10851 ACTTCCTGTT TCACAGACAG TAGGGGCTGT GGAGGAAGAA CTCCTTCAGC
10901 TCCTGCTCTG TCGCAATTGG CCAGCTTGCC TGCGCCTTCT CTGGCGATTG
10951 CCTGCTCTCC TCCCACCCGT GGAAGTCATG TCCCTTCCCT CTCTAGGGGC
11001 AGTCCCTTAG CCAACCTCCC TAGTTTCTTA GGAACTCCCC CAGACATGGC
11051 CTCTCCCTCT GTCTGCAAAC TTTCATTGGC ATGGTCTTCC ATATCCATTG
11101 GGTGTTCAGT TTCTTCACCT GCATTTTTAA AAGGCCCATC CACTGACCCA
11151 GTGCTTCACT CCCTCCCTTC CCTCACAGTA TCCCCTGCCC TCTGCCTTCC
11201 TCCAGTGCCT TCATGTTCCC TCCACTATTG CACTGGGGCC CCCTTTCCAG
11251 CCTCTCCTCT GAAGCTGGTT TTGCTTGGGT CACTGATAGC TTCCCTGTGC
11301 TAAATCCAAT GGATGTGTTA CCAGCAGCAA ATTTGTACAG GTCTGCAGCA
11351 ACCTCAATTC TTGCCTCCTC AGAAGAAAGA ATTCGACTGA GGGGCCTAAG
11401 GCAGAAGGAG AGACGGAGGC AAGTTTTAGA GCAGGAGAGA AAGTTTATTA
11451 TTAAGTGTAG AGTAGGAAGG GAAGGAAGTA AAGTACACTT GTAAGAGGGC
11501 CAAGCTGGTG ACCTGAGAGA AAGTGTGGTT TGACCTTGGA ATTTGGGTTT
```

FIGURE 3C

```
11551 TAGATGTTGG CATACTTCCA GGGACTTGCA TCCCATCTCC CCGGTTTCTT
11601 CCCTTGGGGT GGGCTGCCCG CATGCGCAGT GGCCCGCCAG TGTTGGGGAG
11651 GGGAGCATGC TCAGTGTGTT TACCGGAGTT TTGCGCATGC TCACGTGAGG
11701 CATTCTTCCC ATACCAGTCC CAGTTTTCCT AGAAGGACAT ACACCAATTA
11751 AGCTCTGCCA TTTTGCCTCT TAGTGTGCAT GGTTGAGCCG ACTCACCCAA
11801 CTCCCGAGAT CTTATTGGGA AGCTGATCAC CAGTTTCAGG TTTTTGTATC
11851 TATTGAGAGA CTGCCGTCCC TTGGCACCAG CTGTGACCAA TTAGTATTTT
11901 AGCGACACAG TTAACAACTG CTTGACCATC ACGTGATGGT CGCCTTCCTG
11951 TTGTGGGTCG GGGAGCCCTC TCCTGCCCTG CTCATGCCTC ACTAGCTATC
12001 TACTGTAACG GACACTTCCT GGTTTTCTGA CCATTGGGCA CTATTGACTG
12051 TAACCCCTCC TTGAAACATG GTTCCCTTCA CTCTGCACTT TGTTCCCCCT
12101 CCTTATCCTG AGGCTTTTCT TCGGTTCATC ACCTCCAGCT CACTTCCTTT
12151 AATTTTGCCA TTCCCTGGGG TTCCGTGGGC CCCTCCTCT CTCTCTTCCT
12201 TATATATCTG TGTCCATACT TACGTCTCTC AAATAATATC ACTACTCCAG
12251 GTTGAATCAC ATCTCCACA CCCAGGTAGC TAACTACTCA CCGGGAACGC
12301 CATGGGGCGG CCATGACGGT CTCAGGCTTA ACTCAGCTGA GACTCTACTT
12351 TTCCCCCACG AGTTGTTTGT TCTGCTGTTT TCCTGTTCCT TGGGAACCTG
12401 GGAAGAACCC AGGACTTGTC CCTCTCCTTC CCCTCTATGT CCTTCTAGTC
12451 TGCCTCTTGT CAGTCCCCAC TGCCCCAGGC CAGGCAATTC CATGCCCCTG
12501 GTCCTTTCAT TCGTGCTCTT CTCCTCCCTG TCTCAGCTTC CGAGGTGACA
12551 GCTTACCTGG GTGACAGCAC CACACCCATC ACACTGTGTT GTGTCAACGG
12601 CAGTGATCGT TTTACTTCTC CCCATCTAGA CCCTGAGCTC CTTGTAGGCA
12651 AGGCTTGTCT TACTTTACCT TTGTGACCTC TGTGTCTGTT ACAGTGCCTG
12701 GCACTAAGTC GGTAATTTAC TGAATGAACG ATGGGCCCAC TTTGTTGTGT
12751 TCACCTGTGC CGAGCTGAGG TTCATTGACT CCCACTGCAT CCAGGGGATA
12801 AACTCTGACT TAGTCTTGGA GTGGCAGATA CAAGCGACAC ACACCCGTCA
12851 GCTGGAAGGC TCTTGTCCTC TTTGTGAATC AGAACCCTGT TTAGGCTTCT
12901 AATCCCACAT CAAAGCCCAT CTCCTCCATG AAATACTCAG TTTTTCTAGC
12951 CTGCACTGAT CTCTTCCTTC CCTGAACTTT CAATGTATTT AATGTACAGC
13001 ATTGTTCACG CTACCACTGT ATTCGTCATT GATTGTTTCA TATTTGCAAA
13051 ATGTTTCTCT CCCCAGTTCA GTTGTAGGCT CCTTGTAATC CGGCAGCCCA
13101 TGCCTTATAT GGGCTCTATG CGCTTACGTG GGCCTCTATG AACCCTCAAA
13151 ATGTCTTTTG CCAAATAAAG GCCAAGCCAG ATGGACTGAG CCCTGTTTCT
13201 TCTCCTTGGC TGTGGCCTTA CTATCTTCCT GCCCCTCGTA AACAGCTTTG
13251 CCCCTGGGAG TTTGAGGCTG CAGTGAGTTA TGATCGTGCC ACTGCCCTGA
13301 GGCCTGGGTG ACAGAGCAAG ACCTTGTCTC TAAAAAAATT AAAATAAAAA
13351 ATTTAAAAAA ACAACTTTGC CACCCTACCC ATCACACCCC ACCCGCCTGA
13401 CCTGCTTCAC AGGCTCCCGA CGGCCACTGG CTTCCACCTT CCCCATCTTT
13451 CTCTTCCCGC CTCCATCTTT TAAGCTGCGA ACCAGCCCCT GTTCCTTTCA
13501 CTGTCCAGCT GTCAATGAGC CCAGAGTCCC TTAGCCACCT AGTGCTTTCT
13551 TCCCCCTCCT GCTGTCTCTT GGGGTCTTCT GGTGTCTGAT TCTGTCAGCG
13601 GGGCAGGTGG CAGTACCTGT TCTAGCATTC AGGCCACTTG GGGCTGATCC
13651 ACGCATTGTT TATGTTCTAG CCTGCAGGAC AGCCAGGTGG ATGGCCCTGC
13701 AGCGTGGGAG CCTTGCCCAC GGAGTGTTGA ATTTCTTAAT TGAAATGAAT
13751 ACACTTAAAT TAAACCAAAG TTTTGTAGAA GAAATCCTGG CCAGGCACGG
13801 TGGCTCACGC CTGTAATCCC AACACTTTGG GAGGCCGAGG CGGGTGGATC
13851 ACCTGATGTC AGGAGTTTAA GACCAGCCTG GCCAACGTGG TGAAATCCCG
13901 TCTCTACTAA AAATACAAAA AATTAGCCAG GCATTGTGGT GGGTGCTTGT
13951 AATCCCAGCT GCTTGCGGGG CTGAGGCAGG AGAATCGCAT GAACCCGGGA
14001 GGCGGAGGTT ACAATGAGCT GAGATCGTTC CATTGCACTC CAGTCTGGGC
14051 AACAAGAGCG AAACTCCGTC TCAAAAAAAA AAAGAAATCC TGTTGGCTTT
14101 CTGTGCAGTT TTTTGATGCC ATTGTGACAC AGAGAAACTT TATTTCAGGA
14151 ACTGCTTATA TCAACATCAG AACTTGGA AATGTCTGAG TACTACTTTG
14201 ATGGGAAAGG GAAAGCCTTT CGACCAATTA TTGTGGCGCT AATGGCCCGA
14251 GCATGCAATA TTCATCATAA CAACTCCCGG TGAGCTCTTT TTTTCATTCC
14301 TTTCTTGTTT TTATATTTGG CAAGTCTTTC TTCCCGGGGT TACTTACTGT
14351 TTCATTTCCC ATTTAAGAAT TAGCATATAC CGGCTGGGCA TGGTGGCTCA
14401 TGCCTATAAT CCCAGCATTC TGGGAGCCTG AGGCGGGTGG ATCGTGAGAT
14451 CAGGAGTTTG AGACCAGCCT GGCCAACATG GTGAGACCCC GTCTCTACTA
14501 AAAATACAAA AAAAATTAGC CGGGCGTGGT GGCAGGTGCC TGTAATCCCA
14551 GCTACTTGGG AGGCTGAGGC AGGAGAATCG TTTGAATCTG GGAGGCGGAG
14601 GTTGCAGTGA GCCGAGATCA CGCCATTGCA TTCCATCCTG GGAACAGAGC
14651 AAGACTCCGT CTCAAAAAAA CCAAACAAAA CAAAAAACAT GGGGGATTTT
14701 TAAAACAAAA CTTTGGAGGG GATTTTAATA AACGATAGAA GGTATATCTT
14751 AAGAAACAGA GCACGAGGGA GAAACTACTA CTTACTGATT TTTATATTTT
14801 CCTTTATTAA GCTTTTCAGT TGTCCCATTA AATGTTCCCT ACTAGATTAC
14851 GGGGAGTTCT TAACTTGAGG TTCACGGGAG TTGTGGGATG TCTGTAAACA
14901 ACTTGACATT GTATGCAAAA TTTTGTGTAT ATTTGGATTT TTTGGGGAAG
14951 GATTTCTATG GCTTACAGTT TATTTCTCAAA GGGAAGTAGG GCCCTAAAAG
15001 CTCAGGACCC CGTGTTTGTT TTCTCTCTGA ATCTTGCTAA CCATGGTGTC
15051 TGGGTAGAGA AAGTAGGAAT CCACACAACA GTAGACTCAG ACTTGACATG
15101 TCCAGAACAC AGAGTTGTGG TGGATCCTGA GACTTGCCCC CAGATCCCCC
15151 GTCAGTGCAC GACTCTGCCC CAGCTGTGT ATCAGGTATG GTTGGTACCT
15201 GTTGGCCTTC ATTTCTTAGC CTCTTCAAGG ATTGCCTTGG CTACAAAGAG
15251 TCCTCTCACC TTAGGCTGTG CCCCTTCGGG AGGCAGCCCA CATCCAGGGA
15301 CTGATAGATG AAGGGCCATT CTACCTGCAC ACCCTAGAGG GTGTTTCAGG
15351 CTGTTGATTC CAGCTCAGCT TCTCCTGCTA CCCAGTCCTG TATCCTCTCC
```

FIGURE 3D

```
15401 CCCTCCCTCA GGTGTCAGTA ATCCCAAGGG ATAATCCCGA ATAAACATCC
15451 TGTCCTTTAA ACTTCATCTC AGAGTCTGCC TCCTGCAGAA CCTAACTTGC
15501 AACAGAGCTC AGCAAAACCC AAGCTCATTT TATTAAAGAA CCCAGATCAA
15551 AAAAGAGCTT TATGGGCTGG GCACAGTGGC TCACGCCTGT AATCCCAGCA
15601 CTTTGGGAGG CCAAGGTGGG TGGATCACAT GAGTTCAGGA GTTTGAGGCT
15651 AGCCTGGCCA ACATGGTGAA ACCCCATCTC TACAAAAAAT ATAAAAATTA
15701 GCCAGTCGTG GTGACACACA CCTATAAATC CCAGCTACTC AGGAGGCTGG
15751 GGCAGGAGAA TCGCTTGAAC CCAGGAGGTG GAGGCTGCAG TGAGCAGAGA
15801 TTGCGCCACT GCACTCCAGC CTAGGGGAGA CTCTGTCTCA AAAAAAAAAA
15851 AAAAGAAAAG AAAAAGAGCT TTATGATAGA TTTCTATAAA ATTGCTTCAC
15901 TCACTGAATG CAGCACAGTT ATAGTGTCTG CATGTTTCTC AGACAAGCCA
15951 AACCTACCTA GCCTGCTCAG CTGCCTCATT GAAGCACTG TTATCACTGG
16001 CACCTGGATC TTGGCACCAT CCATTCCTGT GTGAAACTCT TTTAGTTCTA
16051 AGAAGTGAAT ATCATTGCCA GCAATCAGGA TAACAGACTA CCCAAATTGT
16101 GCTGTACAGA GATCTGTTGA TATCAATTTT GCAAATAGCC AATGGCATTG
16151 GATTACATTA GTCCAGTTTT CAAAGCTGAA CTAGATGTTT AGGGGGTCAA
16201 ATTATTAGAC ACAGTTTTCA CAGTAGATAA CAGGTTGAGA GTCCAGGTGT
16251 GATAACAATC CTGTATTCAG AGGAGGTAAC TTTTATAGCA CTATAAAAAA
16301 CTAAGGAAAT TACCAAAGCC TATCCCTGAA AAGACTGTAA CAAAACAGCC
16351 ATTTAGCACT GACTGGCTCC AGTGATTCCA AAGGTCAGGC CACTAACAAC
16401 TGTAGAGCCA TTCCTGGTTT CTGTGTGTTC TGTGTCACTG AGCCAGCCAC
16451 TGCTGCTGCT GTTTATGGGA TAGGCAAGAA GGTTGCTACC AAAGGAAATG
16501 GTTTTGTCTT TCACCTAGGA GATGGTTCTG TGGATATGTC CATAGTCACT
16551 GTTAAAACGG ATCTTTGAAG TACATTCTAC AGTAAGGGAC ACCCATTAAG
16601 CTGGAGATTT TGATGAGCAG ATGGTCATCA TTTCATGCAT GAGTGCAAGG
16651 TCAAGCATAA GAACCTCAGT GAGAGCAAGA GGGCTGCAGG GCTTGTGACC
16701 GTGGTGTGTG CACCTTGTTC AGCACCCTCC ATGCCAGGAT GAGGCTGATT
16751 CTGTCTGCAA AGGAATCAAC TCCTATACTT TTTTTTTTTT TTTTGTCTTG
16801 CTCTGTCACC CAGGCTGGAG TGCAGTGGCA CAATCTCAGC TCATTTCAAC
16851 CTCTGCCTCC CAGGTTCAAG CGATTCTTCT GCCTCAGCCT CCCAAGTAGC
16901 TGGGATTACA GGCACACACC ATCACGCCCA GCTAATGTTT GTATTTTTAG
16951 TAGAGACGGG GTTTCATCAT GTTGGCCAGG CTAGTCTTAA ACTCCTGACC
17001 TCAAGTGATC CGCCTGTCTC CCCCTCCCAA AGTGCTGAGA TTAAAGGCAT
17051 GAGCCACCGC GCCTGGGCAC TCCTACACTT TCCTTACCCA TCCCCAATTT
17101 GAAAGAACTG AATGCTGGTT AGTCCATAGT ACCCTGGACC CTATAGAGAA
17151 AGCTCTGCAC AGAGCAACCT GGATAAGTTG TAGATCCAGG TATCATCATA
17201 GGGGTCTCTC TCCACATATC CCAAGATTCA GAAGCTCTTG TAATTTCTTC
17251 TTCAGTGGCA AGCAAATAAG CAATAGTGTG AACCCTGCAT CATTTATGAT
17301 GCAACTTTGC AGACATCCAT TATATCCACA GCTAAATCTG AAAATATTCA
17351 GGGGTTGCTG CTTTTAGATA CCAATTATTT TCTCTTGACA TTAAAATGCT
17401 AACAAATCTA TGACTGTTAG GATCAAGTTA AAAAAATTCC CACTGAAGAG
17451 AGACAGACTT TATTCTGAGC CTTACGTGTT TCTTTAGGTT TAGAAGGTGA
17501 ATGAGCAGTG GCTGGGGAGG ATGGCCTAGA AGTTGGAGCT CACAGGCTTC
17551 CTCCCTGCAC TCTGCCATTC CTTAGATTGG AGGCGCCCTT GATACAGATC
17601 CCTCCCTACA CACTGGGGGT TTACTTGCAA TTTAAGACTT CACATTTTAT
17651 ATTAGTATGA ACAGGGAAAA TATATTTTGT AAAACCACAT GTAAACCTCG
17701 TAAAGGATTC ACTGGTAGGG TCATTATATT ATTCTGTCTA TTTTTAGGTA
17751 TGTTTGAAAC TCTTCATTAT TAAAAAAATT TTTTTGGCCG GGTGCGGTGG
17801 CTCACGTAAT CTCAGCACTC TGGGAGGCCA AGGCAGGTGG ATCATGTGAG
17851 GTCATGAGTT TGAGACCAGC CTTGCCAACA TGGCAAAACC CCATCTCTAC
17901 TAAAAATACA AAAATTATCT GGGCGTGGTG GCACATGCCT GTAGTCTCAG
17951 CTACCTGGGA GGCTCAGGCA GAAGAATCAC TAAAACAAGG AGGCGAAGGT
18001 TGCAGTGAGT CAAGATTGCG CCCCTGCACT CTAGCCTGGG TGAAAGAGCA
18051 AGACTCCATC TCAAAAAAAA AAAAGATAAT TTTTTAAATC TAATGAAGGA
18101 GGAAAGAAAA GTCTTGACAG GCATGCTGAA TCATAGCATA CTCTTGCAGG
18151 TGTGAAGTAC AGAGGACGTA GCCAACTCTC AAGACCAAGG GCTTCATTTT
18201 CCATGCTACC TTGCCTGTCA CCTCTCCCAG ATCCTGGGAA AATGTGATCC
18251 ACTATTTCAC AGTAGGAAAT AGAAATGGTG CCCAGTTTTT TGAAGGCTTG
18301 ATTCAGTTTG GCATTTTGGA GATGTCATCT TAAGGACAGT GTGAGGTTTT
18351 TCTGTAATCT GTGCATTTTG GTCATCTGTC CCACCCTCAT GTTATGGATA
18401 AGCAGTGGCA GCATTTCCCA GATGTAAGCT GACACACACT AAAGCTGAAC
18451 TGGATAAAAA ATACATCAGG TAAAACTATG GAACATCTGA AATATGATGT
18501 ATATTCTACG TAGAAGCTGT GTTACAGTAC CAAATAACAT TTCAGTTTCA
18551 TCCTGATTTC ATCAGTCAAC AATTTAGCCA TGCAAAATGA CATTTTTTAT
18601 TCTATTTATT TATTTATTCG GAGACAGAGT CTCGCTCTAC CCCCCAGGCT
18651 GGAGTACAGT GGTGCAAGTC TCAGCTCACT GCAACCTCCA CCTCCCAGGT
18701 TCAAGCGATT CTCCTGCCTC AGCCTCCCAA GTAGCTGGGA TTACAGGCAC
18751 CCACTACCAT GCCTGGCTAG TTTTTGTATT TTTAGTGGAG ACGTGGTTTC
18801 GTCATGTTGG CCAGGCTGGT CTCGAACTCC TGACCTCAGG TGATCCTCCT
18851 GCCTCGGCGT CCCAAAGCGC TGGGATTATG GGCATGAGCC ACTGCGCCAG
18901 GCGCAAAATG ACATTTTTAG ATGGATATAT AGTCTATGAA ATTTCAAAAT
18951 ATTTTAAGAA ATCTTTGTTG TAATAATAGC TTCAGATTAC CAAAACAACT
19001 CTAGTATCTT GGTGAGTGCT GCCAATTTCA TTGCAACTTC TCAGCAGGAG
19051 CCCCGTCTGC TGATGTAATT TATCATAATG GAAGTGGTGC CCAACTTCTG
19101 AATGCATGAG AAAGGCTAGA CCTTACCTGT TGTTTTAAGG TAAGGTCTAC
19151 TGCTAACTAG TAGGAGGTGT CTAATTTATT AGACTGAAAT TCACTTGCAA
19201 AAATATTCTA AAAGCCTTAT ATTAAAAAAA AACTGTAAAA GTTTATATCT
```

FIGURE 3E

```
19251 TTTCCTGTGC ATTCAACTCA AAGAAGATAG GGCCTAGTAA ATTTACCTGA
19301 AAAATATTTA AGTATTCTAA TATAAAAACT GAATCTCACT GAGGGATTCA
19351 GGTGGCTTAA AACTCACCTG AACCCTGAAC CTCTATTTTC TCATTTACTG
19401 AAGTTTATTG GGGTTTTTGT TTTTTTGTGT GTTTTTTTGA AATGAAGTCT
19451 CTGTCACCCA GGCTGGAGTG CAGTGGCATA ATCTCGGCTC ACTGCAACCT
19501 CCACTTCCCG GCTCAAGTGA TTCTCCTGCA TCAGCCTCTC AAGTAGCTGG
19551 GATTACAGAT GCACACCACC ATGCCCGACT AATCTTTGTA TTTTAAGTAG
19601 AGTTGGAGTT TCACCCTGTT GTCCAGGCTG GTCTCGAACT CCTGACCTCA
19651 AGTGATCCGC CCGCCTCAGC CTTCCAGAGT GCTGGGATTA CAGGCAGGAA
19701 CCTGTAACTG TGCCTAGACT ACAGAAGTGG TTTTTATATG CTAATTTGTC
19751 CCTACCCTCC ACTGCTTTTG TTTTAATACT CCCCCCTTAG AAGAATTTGT
19801 TGTGATCTAG ACATATTAAG AAGTTGTAAC TGAAATATTA ATAAAGAATG
19851 AGGCCAGGCG TGGTGGCTCA CACCTGTAAT CCCAGCACTT TGGGAAGCTG
19901 AGGTGGGTGG ATCACCTGAA GTCAGGAATT CAAGACCAGC CTGGTCAACA
19951 TGGTGAAACC CCATCTCTAC TAAAAATACA AACATTAGCT GGATGTGGTG
20001 GTGTGCACAT GTAATCCAAG CTACTTGGGA GGCTAAGGCA GGAGAATGGC
20051 TTGAACCCGG GAGGCAGAGG TTGTAGTGAG CCGAGATCAC ACCATTGCAC
20101 TCCAGCCTGG GCAATAAGAG TGAAATTCCA TCTCAAAAAA AAAAAAAAAA
20151 AAAAGGAATG AGTAGCACTG TAGACATGAT TTCCAGGCTG AGAGCAGTTG
20201 AAAGGGTCTA GGGTTTAGTT CTAAGGCTGC TGGTAAGAGG AGCCAGCGTG
20251 ACATCATATT TTAAAATTAT ATGTAAAGCA AGATCAAAAG CTTTCCTCAT
20301 GCTGATTATT TGTCGATAGT TAAATTACAG CACCTTTTAT GTAGTTATAC
20351 TTCATTTTTC ATTGCTTTCT GCCGGGTCTG AGGAATTGGA ATGAGCATTA
20401 CCTTGTGCAG ATGTTCAGAT TCGATTTTTA AAGAAAAAGT CATATTTCAG
20451 AATCCCTCTC CCTTTTTTCC CCTCTAAGAT ACAACCTGAT GGTATTTGAA
20501 AATAAGCATT TGGAATAAGT GCAACATTTG GTTAGTGTGT GTTTAAATGA
20551 GGATATGTTT TAGGTTCCAA ATGGTTATTT CGCCAGTTTG ATTTTCTTGA
20601 AATTTAGTTT TTAAAAATTG CCATAGATGA TGGTGGTAAT AATGATTAAA
20651 ATGAAATGGG GGACATTCCC TCTGAACTGT AAAATTTATA TCTGTGTCCT
20701 GTCTTCTTGA GCCTACTTAT CCTATAGTTT GTGTTAAACT TGGGAAATAA
20751 AAGTTTAAAT TTCTAATGAG AAGGTTAAAT GTGAGTTGGA AGAAAGTTTT
20801 ACAAACATCT TCTGTTGGTT ACTGAGGTTG TCATACTAAA CGTTTAATTT
20851 AAGACATTAC TACGCGGGGT GCGGTGGCTT ACGCCTGTAA TCCACACTTT
20901 GGGAGGCCAA GGCAGGCGGA TCACTTGAGG TCAGGAGTTC GAGACCAACC
20951 TAGCCAACAT GGTGAAACCC CATCTCTACT AAAAATATAA AATTTAGCTG
21001 GGTGTGGTGG TGTATGCCTG TAGTCCCAGC TACTCATGGA GGCTGAAGTG
21051 GGAGAATCAC TTGAACCTGG GAGGCGAAGG TTGTGAGCCA ATATTGCACC
21101 ACTGCACTCC AGCCTGGGTG ACAGAGCGAG ACCCTGTCTC AAAAACAAGA
21151 AAAGACAGTA TTAAAAGCCT TGAACATTGA GACAGTTGAG TCTTTAAAAT
21201 ACTTTTAAAA AATGCTTCTC ACCTATCTTC CCTATCCACC CCAAAATTTA
21251 ATTGTAAACT TATAAACTTA AACACCTGAC CAAGAACACT GTTATAAAGA
21301 TGATTCTTCA GCCCAATAAG ATCAGCCAGA CTTCTGATCG TTTACTGTTT
21351 TTTTGGCTAA TGGTACAATT TCTACTTCTT CAATGGGGAA TTCATAAAAT
21401 GTAGTTGTGG CAGGGTTTCT CATACATTTG TAAATGTATA GAAATGGCTG
21451 TGTGGTGAAG CCAGAGTTTT TATACCGTTT CTCTTAGAGA AATAACATTC
21501 TTTATCCTAG ATCCGATGTC CAGTTTTCAC AAGCTGATTG CTGAGAAGGT
21551 TCTAGGCGGC GTCTGTTAAA AAGCATTGCT TTCTGTTAAT TAGACATGTG
21601 CAAGCCAGCC AGCGCGCCAT AGCCTTAATT GCAGAAATGA TCCACACTGC
21651 TAGTCTGGTT CACGATGACG TTATTGACGA TGCAAGTTCT CGAAGAGGAA
21701 AACACACAGT TAATAAGATC TGGGGTGAAA AGAAGGTATG GTTTTTTGGT
21751 TTTTTTAAAA TCTCTCTTAC TGAATCACAC GCTTTTCGGA CCGCATTTGT
21801 TTCTCAGATT TGTCTCATTA AAAATATGCT TGCTCAAATG TAATGTGGTC
21851 TTCTGAATTT CAAAAAAGTA TTCATGTCTT GTCCAAATAC AGATATTTGA
21901 TAAATAAATA ATAAAAAATA CCATGGAAAA ATAAACTTAG TATTTCTAAT
21951 AGAATTCCTT TGGTTATAAG GAAAGGGATT TTCATGGGTG TCCAAAAAAT
22001 GTATTTCATG AGGAATCATA CGTTTTACTT TTGGGCTTAG ATTACCCAGA
22051 TTCAGTTTAA TTTTTTAAAC ATTTGTATAA TTGAGTGCTG CATATAAATG
22101 CCAAAGCAAA CAAATAAAAC TAATAAAAGA AAAAAGAAAC CTCAGAGAGA
22151 TACTGTTCTG CCATGAAAAT TCTGTCTTTT GAAATAGAAG TTCTGTAATT
22201 GGGTTTGGTT CATATATGTA TATATTAAAG CATATTTCTA TATTATTAGC
22251 ATTGGGAATA TGGGAAACAG GGACTTGGTT TGAGGATGCA TAGATCCTGG
22301 GTTGAAGGAT GAGAATAAAG TTGAACAGAT GAGAATGAAA ATGCACAGGC
22351 ATCCATCGCC ATCACCACAC ACGTGCTCTA CAAACAAAAA GTTTGTGCAG
22401 GCCAGGCGCA GTGGCTCATG CCTGTAATCC CAGCACTTTG GGAGGCTGAG
22451 GTGGGTGGAT CACCTGAGGT CAGGAGTTCG AGACCAGCCT GGCCAACAAG
22501 GCAAAACCCT GTCACTACTA AAAAAACACA AAATTAGCC AGTGTACACC
22551 TGTAATCTCA GCTACTCAGG AGGCTTAGGC AGGAGAATCG CTTGAACCTG
22601 GGAGAGGGAG GTTGCAGTGA GCCAATATCA CACTACTGCA CTCCAGCCTG
22651 GGCAACAGAG TGAGACTCCA TTTCAAAAAA AAAAAAAAAG TTTGTGCAAA
22701 CAACTACCCC ACCCTCACCT CCTTTTCTCT CATAGATTTA TAGTATTCCT
22751 GGTTCATTCC TATTTAATTC TCCTTATTAA AAGAAGAGAT ATATGTATAT
22801 ACACACACAC ACACACACAC ACACATACAT ACACATACAT ATATATATGT
22851 TTATTGTTAT CTTCACATGC TGGTTTTATT TGAACATAAA TGACTGTTTT
22901 GAAATCGAGT CTTGCAATTT CATTTATATG CCTTTTATTT CAAATTTTAG
22951 ATTAAAAGGT TTTACGTCCT GTTGACTAAA TTCTGTACAT CAGAATGTTG
23001 GCCAAAAAGC AGATGGCGTT TAGATTTGGA GAGGATGTGG GTAACTCTAT
23051 GACCCATCCC TGCCGTCAGC TGTATCTGTT TTCAGGCATA GCCAGTCCTA
```

FIGURE 3F

```
23101 AAGCCTTATG TGGAGCCTTG GGCGGGGGAA GAGGATCAAG AGAACAAATG
23151 ATGGTCTCCG CCTTGGCTAG CCCCTGTGTG TCTGCCTCTG CCACTGGGGA
23201 CCTCTTTCTG AGGGCAGGTC AAGGACACAT GTGCGCCTT CACCTGCCTC
23251 TTTCAGTTCT GACAGCCATC TGCTTAGCAC AGGGCTACTT GCCAGTTCCT
23301 ACCTGTTTCT GCCTCTGACC CACAACTGCT ATGTTACCGG TACAAAACCC
23351 CCCACACACA GTGCCCCCTC GGTGAGCCCT TGTTAGGCCT GGCCTGGGCT
23401 TCCTAGCACT TCTTTCCTTT AACTCCCACC CCTGGCCGTC ACAGTCCTGT
23451 GGCTTCCATG TCATATGCTG GACCTTTGGT CTCTAGGATC TCCCCGGCCA
23501 GGTGAAGAAG GAACTAAAGG CCAAAGGATC CCGAGCCTTG AGCTGCTAAT
23551 GATGTAGGGG CTGGGTCAGG GAATGTAAGT GGGTACCTAT ATATCATAAT
23601 TTGTAAAATG ACTTTATAGG CATATACTTA CATCAGGATG TCTTACATAA
23651 TATGTATATT ATATAAAGTG GTGATTAATT GGTAAACACA ATGAACATCA
23701 CTGTTTAGAT ACTGAAGAAC CTAAGACAAT AAGTACCTAA ATAGTTATGT
23751 TGAAAATTCT GTGAACTCTA GCCTTTATAA CTAATTACTA CAGAATGTAA
23801 CACTTACGGC CGGGTGTGGT GGCTCACGCC TGTAATCCTA GCACTTTGGG
23851 AGGCCGAGGC AGTTGGATCA CTTGGGGCCA GGAGTTCGAG ACCAGCCTGG
23901 CCAACATGGT GAAACCCCAT CTCTAGTAAA AATACAAAAA TACCTGGGCG
23951 TGGTGGTGTA CGCTTGTAGT CCCAGCTACT CATGAGGCTG AGGTGGGGGG
24001 ATTGCTTGAA CCCAGGAGGA AGAGTCTGCA GTGAGCCGAG GTCATGCCAC
24051 TGTACTCAAG CCTGGGCAAC AGAGCAAGAC TCTTTCTCAA AAAAAAAAAA
24101 AAGAATGTAA TATATATCTT TAAATATGCA AATTAATGTG ATATATAGGG
24151 TGTATTTGGT TATAGCATAT AATTCAACTA TTTATGCAGT AGTTTATAAC
24201 TAGTTGCTAA TACAGTGTAG ACATCCATCA CAGTCTAAAG AAGACTGGAA
24251 ATATGTTGAT TGCTTAGTGT TCAATGGAAA AACTTTTTTT TTTTTTTGTC
24301 TAGGAATGAG GGGCAGTGCC ACATAGTACA AAAAGCATTT CACTTGGAGC
24351 CAAAATTCTT TGGTTTAATT TTTATTGAAA ATAACATGTA TCGTGCCATG
24401 CTCTGGGGTG TGCTCAGTAC TAGCTGAGAT GATTCCTAGT CTGAGCTCCC
24451 ACTCCACTCC ACCCTCCCCA CTGCCCTGGG AGCATAGAGA CTAGAGCATC
24501 ACTGACTGGT ACGCAAGGTG TGATGGTCGC AGCATGCATG GGTGTTGTAC
24551 ACGCACAAAA GGGAGGCATC TGACCAGACT GAGGGATCGG GGGGAACTTC
24601 TTAGAGGTGG CATCTGAACC AATTATGCAA ATAAGTCCAC TCAGTGAAGA
24651 AGGGGGCAGA ACTTTTTGAG CAGAAGGAAC AGTAAGTGGA AAGGCACAAA
24701 GGAAGAATGA ACATCCAGTG TAGTGAAACT GAAGGCAGCT GCATTTTGGT
24751 GGGGCTGGTG AGTGAAGCTG CTCTCCCTCT CCAGGCATTG ATTTCTTCAG
24801 GTGTCAACTG GGGAGATGGA CATGGTCATC TCTGAGAGCC AATACAGTTC
24851 AAGTACTGTC CCAAATCTGT AACCGATTAT TAGAAACTGG GAAGAGTGAC
24901 ATGGTCATCT CTGAGAGCCA GTCCAGTTCA AACACTGTCC CAAATCTGTA
24951 ACTGATTATT ACGAACTGGG AAGTGACATG GTCATCTCTG AGAGCCAGTC
25001 CAGTTCAAAC ACTGTTCCAA ATCTGTAACT GATTGTTACG GACTCCTGTT
25051 GAGGAAGAAG AAGGTAAAAA ACCCTGCATC CAAGATGAGC CCCCACTTCC
25101 ACGAAGCTCC CTTCCAGTCA GTTTCATCAT TGGCTCTACT GCTCTGATGG
25151 ATTTTTCAGA ACGTTCTGTT TTCCCCCTGT CTTTTTCTAG GCTGTTCTTG
25201 CTGGAGATTT AATTCTTTCT GCAGCATCTA TAGCTCTGGC ACGAATTGGA
25251 AATACAACTG TTATATCTAT TTTAACCCAA GTTATTGAAG ATTTGGTGCG
25301 TGGTACGTTG ATTCTGATTT TTCTTCTTTG TTATTCAACC CTGGTGTTTA
25351 GCCAGGCAAT AAAGCCACCT CTCAAATGAC TCCTTTCCTT CTTTATAGGT
25401 GAATTTCTTC AGCTCGGGTC AAAAGAAAAT GAGAATGAAA GATTTGCACA
25451 CTACCTTGAG AAGACATTCA AGAAGACCTG CAGCCTGATA GCCAACAGTT
25501 GTAAAGCAGT ATGTACGTTC TGTCTTTCTT CAAGTTAAAG CCTCATAGCT
25551 CTTTTTTGGG AGCTAATTTT CCTAGAAAAT ATTTCGGTGA AGAATCTTAA
25601 AATAGTACCC AAAAATCCCA AGAGGTTAAT GAGGAAAAGA ATGACATCCC
25651 CAAACAATAG AGGACTTCTG CTGTGTTTTC ATTTTTGCCA TCTTCTTTTG
25701 GTATGCAGGC GTTGACTTTT CATCTTTTCT TCCCAAGAAT TCAATCAAAA
25751 TAAGCTTTCC CGCACCTTCC CCAATCTGAT TGCCAAACTG TATCATTTTG
25801 AACAATTTAT CATAATTTCT CTAATGATTG ATATCACACA CACTCTTTCT
25851 GACACTTCAC CTTTTAGAAA TGAAGTGCTC TGTTCTTTAA TATAATATTT
25901 ACTCAGGAAA AGATATCTGT TAGATTGTAC TAGCATTCTA TGAACTTTTT
25951 TTTGTTTTTT TGTTTTTTGT GTTTTTTTGA GACAGAGTCT TTTGCTGTGT
26001 GGCCCAGGCT ACAAAGCAGT GGTGTGATCT TGGCTCACTA CAACCTCCAC
26051 CTCCCAGGTT CAGGCAATTC TCCTGCCTCA GCTTCCCTAG TAGCTGGGAC
26101 CACAGGTGTG CGCCATCACA CCCAGCTAAT TTTTGTATTT TTCATAGGGA
26151 TGGGGGTTTG CCATGTTGGC TGGGCTGGTC TCAAACTCCT GCCCTCAAGT
26201 GATCCACCCA CCTTGGCCCT GCAAAGTACT GGGATTACAG GCATGAGCCA
26251 TTGCACCTGG CCAATACATT GCACCTGGCC AATCCTTCTA ATATTTTTAC
26301 ATGAAATATA AACAAGTCCT ATTTCTTCAG AGTACAAATT GAGTATAAGC
26351 CATAACTGTT TTTCCCCTTG CTTTCTCCCT CCCTCCGCTG TGCATACACA
26401 TGTATACATT TTTTTTTTAA TGAGTAATAC CTTTAATCCG TAGACAAATG
26451 TGTGGTATTC ATCGTTAGTC CAAGAATGAA AAGCAGTCTC TCCATAGAAT
26501 TGTTTATCTG CCCATCTCTA AGCCTGACAG ATACACAGAG ACAAAACCTG
26551 GACAAATGAC ATTCCCATGT AATTACAGCC ACAAAATAAG GAAGACCTGT
26601 AAGGGTCGCA TGTCAATTGC TGTCATGATA GACTCCTAAC ATAATTAACA
26651 GGTAAAGAGA GCTTTTGCTC AGACCTCTCA GATGAAAAAG TCTCTTGCTG
26701 TTAGTGTCTC TGTTTTGAAA AGTGTCAAGA AATGTATAAT TGCAAGGCAG
26751 AAAAGAATGA GGACAATCTT TTCTTCCTAA AAAGACCTAA TAGAAACTTT
26801 AAGGAATGTG AATTATGTAG AACATGCTAG CCACAGTCTC GACCACTTTT
26851 GTCTTTTTAT TAAAAGGGCT ATTATGTTTT TATTTCCAAG AAATTATGTG
26901 GGTTTTTTTT TTAAAGTGAG ATGGAAGAAA GTATAGACAC GAGATGCTAA
```

FIGURE 3G

```
26951 ATAAGAGAAT AGCCTATTTT AAGTGGGTGC TCTAACACTT TTACAGTAAT
27001 CCTTTACATA TTATCATGCC CTTGATGGCC CAACTCTCCC TGAAGGTCAG
27051 GATCCATCCT CTTAACACAT TAGGGTGCCT TAATATTACT TACTAATATT
27101 TATCCTTAAG AGGATGTGTT AAGTGAGGCT CATTGATAAT TTCACAATTT
27151 GAGACTGCAA ACTTAGAAGC ATTAGCATGG TCAGGCAAGG TGGCTCACAC
27201 CTGTAATCCC AGCATTTAGG GAGACTGAGG CGGAAGGTTT GCTTGTGACC
27251 AGAAGTTCAA GACCAACCTA GGCAACATAG CAAGATCCCC ATCTCTACTT
27301 AAAAATAATG TTTAAAAAAT AAAGTCTTAG AAGCATTAGT AGTAGTGAGA
27351 CTATTGGAAT TGGAAACACC AAGACTTACT GTCTGCACCA TGCAGACATC
27401 CTGCAGGCAC GGGGTGGGGC GGCACCAAAT TGGAGCTAGC ACAGAAATTC
27451 ACTCAGTGAT GGAAGCTTAC AAAGGGTCCA AAGAAATGGA CCTGAGTCAT
27501 GATAGAGAGG TTTCCTTGTG GTCACTGTTT TCTGTTTAAG AAGCCAAAGA
27551 TAATGCACAG GAATTCTTTT ATAAAGATAT GCACCTCATT CTTCAAAGAT
27601 TAGCAGCTGA ACGAACAGTG AACATGTTAA CGTGGCTGGA CCCTTAATAA
27651 AAATGAAATG TTTCATGCTG CCCACTAGGG GGCATGCTGG CATCGTCCCA
27701 GCACTACCTC CTTTTCATGT GGTTTATTCC TAAACTCCAC AGCTCTTAGA
27751 ATAATAAAGC AAAATGATAG TGTGAGCTAT TTGAATAAAA GTTTCTATAT
27801 TTAAGTGCCT ATGGGTGGAA ATATTCCAGA GGTGTTATGG ATTCAAAATG
27851 GCTATTTTTA CGTACTCTTG GTATTTAAAA TGCAAAGCCA TGCGAGCTCC
27901 AAATAAATGC ATGCAAAGCA AATTAGACAC ACCAAAAAGA GGGGAGGAGG
27951 AGAACTGAAA GAGCAGAATT ATTACAGAAG AAGAACTAAT GGGATTGCAA
28001 AATGTATTGA GAATTGGAGG GAAACTTACA AGCTGCATTC TACTAAGGAT
28051 ACCATTTCTT CATCTCCCTT CCTTTTTTA GTGAAAATAA TATTAAAATC
28101 TAAGAGAGGG CTGTCTAGGG GGATTGTTTT GTGATTGACT GATATTAAAA
28151 TAGAATCCAT TTTAGGCCGG GCACGGTGGC TCACACCTGT AATCCTAACA
28201 CTTTAGGAGG CCGAGGTGAG TGGATCACTT TAGTCCAGGA TTTCAAGACC
28251 AGCCTGGCCA ACATGGCAAA ACCCCGTCTG TACTAAAAAT ACAAAAATTA
28301 GCCGGGCGTG GTGGTGCACG CCTGTAATGC CAGCTACTTG GGAAGCTGAG
28351 GCAGGAGAAC CGCTTGAACC CGGGAGGTGG AGGTTGCAGT GAGCCAAGAT
28401 CACTCCACTG CATTCCAGCC TGGGCAATAG AGCGAGAGTC TCTCAAAAAA
28451 AAAAAAACAA ACCAGAATTC ATGTTATTAT CAAAAGATGA CTTATTTATT
28501 TACATACTTA CTCACTTGCA AAATACATTT TGTACTCATG CAAAATACAT
28551 TTTGTAGCTT ACTAATAAAG ACAGTGGCTT GTTTCCCAGG AAATCTGGTG
28601 GAAATGAGAC CTGAGAGGTC AGAGGGCCTG TCCAGTTGTT GTTAAGCCAG
28651 ACAGTAGCTG AGTTGAGACT TGAACCCAGA GCTGGGTATG GTAATCCTGC
28701 CTTGTTTCTC TCTCTCTCTC TCTCTTTTTT TTTTTTTTC TGAATTTCTA
28751 TTTTCTCCAG GGCTGCTTGT GGCCTGGAAT TAATGGGCTC TCTTCCTATT
28801 ACTTGATTTT CAAAGCCTCA GAGTACCACT ACAGAATTGC ATATTGTGGG
28851 TCACATTAGC AGAACACTCT TTTTTTTTTT TTTTAATTCA TTTTTTTGAG
28901 ATGGAGTCTC GCTCTGTTGC CCAGGCTGGA GCGCAGTGGC ATGATCTCAG
28951 CTCACTGCAA CCTCCACCTC CCAGGTTCAA GTGATTCTCC CACCTCAGCC
29001 TCCCGAGTAG CTGGGATTAC AGGTGCACAC CACCACATGC CACACCTGGC
29051 CTCTTTTTTT TTTACAATAT TCATATCTAT CTATAGGCCT CATTCAGATC
29101 TTGCCAGTTG TGAACTGTTA TAACGAAAGG GAAAACATAT TTTTCTGTTC
29151 CAGCATCCAG TCCAGGATTT CACGTTGCAT TTTGCTGTCA TGACTCTGTA
29201 GTCTCTTGTC ATCTAGAACA GTCTTTCTTT GCCTCTCATT ACCTTGGTAT
29251 TTGGAAGAGT GCAGGCCAGT TATGTTGTTG AGCCTCTCAG TCGGGCTTCT
29301 CTGATACTTC TCAAGATTCG ATCCAGGTTA TGAATATTTG GCAGGAATAC
29351 CACAAGAGCG GTGCTGTCCT CAGCTCCTCA TACCAGGAGG CGCGTGCTGT
29401 CTTGTCTGTC CCGTTACTGG TGATGCATGC CTGGATCGCT TGATTAGGAT
29451 ACTGTCGGGC CGGGCACAGT GGCTCACGCC TGTAATCCCA GCACTTTGGA
29501 AGGCCGAGGT GGGCAGATTA CCTGAGGTCA AGAGTTCAAG ACCAGCCTGG
29551 CCAACATGGT AAAACCCCAT CTCTACTAAA ATTATAAAAA ATTAGCTGGG
29601 CATGGTGGCG GGCACCTGTA ATCTCAGCAC TTTGGGAGGC CGAGGCGGGT
29651 AGATCACCTG AGGTCAAGAG TTTGACAAGC GTGGCCAACA TAGTGAAACC
29701 ATGTCTCTAC TAAAAATACA AAAATTAGCC GGGCGTAGTG GCAGGCGCCT
29751 ATAATCCCAG CTACTCTGGA GGCTGATACA GGAGAATTGC TTGAATCCGG
29801 GAGGCGGAGG TTGCAGTGAG CCGAGATTGC ACCATTGCAC TCAAGCCTGG
29851 GCAACAAGAG TGCAACTCCA TCTCAAAAAA AAAAGATACT GTCTGCCAGG
29901 TTTCTTCAAT CTAAAATTAC TATTTTAACC TATTTTGGGC AAAGTATTTT
29951 CAGATTATGT AAATATTATT CTGATGGTTG TCAAATGGCT GTTTTTCTAT
30001 TTTCATCATT TCTTCTATAT CACTCTTCTA CAAGAAAGTT GGTATCCTAT
30051 TTTTTTTGTT ATTATTATTT CATTCTCAAA AGAGCTGAAG AGTTGGTATT
30101 CCATTGTAAG GAAGCTCTTA ACTGTATGGG CTCTTGGATT CTTATTTTAT
30151 TCTGTATCTT TTTTTTTTTT TTTTTTTTT GAGCCAGGGT ATCACTCTGT
30201 CACCCACGCT GGAGTGCAGT GGTGCAATCT CAGCTCACTG CAACCTCCAC
30251 CTCCCGGGCT CAGGTGATCC TCCCACCTCA GCCTCCTGAG TAGCTGGGAT
30301 TACATGCGGC TGCCACCATA CCCGGATGAC TTTTTTGTAT TTTTAGTAGA
30351 GACGGGGTTT TGCCATTTTG CCCAGGCTGG TCTCAAACTC CTGGCCTCAA
30401 GTGATCGCCC ACCTCGGCCT CCCAAAGTGC TGGGATTATA GGCGTGAGTC
30451 ACCGTGCCCA GCCATCTTAT TTTATTCTGT AGATTATAAC ACTGTCATTA
30501 TTTTAATACT CAATTATCCA ACGTATGGCC AGTAGGGGAG GCCCTTTAAC
30551 CTGGCTCTGT GTCCTCCATC ATTTTTTCAG CACCCCATTT CTGGCAGGAG
30601 ATATTCAGCC CTGTTATTCA CTGTTCTCCA AGGAGCCCAC ATTCCTTTTG
30651 GTGGAAAATG GTGTTAAGAA ACCAGAATTT GAGTACTGGG TGTCATCGTT
30701 TCTAGACCCA CTCAATGGAC AGAGCTAGGA AATACATGTA TGTATTATAT
30751 GTAATGTAGG TAGATACGTG TATATCTTTC TGTACCCATC CATACTTATT
```

FIGURE 3H

```
30801 CAAAACCACG AGGTATCAAA CAGATAGTTC CAAATCCATC TAACACCACA
30851 GGATTTGTGG TTTATTCCAG GATTCCATCT TTCCATATTT GTAACCCCCT
30901 TCCCAAACAG TGAGAGACCT GGCTCCTCTT CTCCGCGGTG TATTTATTTG
30951 CACAATCTGA GAATATACCA TAGGAGTTTA CAAATTCATG ACTCATATCT
31001 CTGTGAAAAA CAAACCCAGT AGCTAGAATT CAGTATTTAT CATTCCTTTT
31051 GTCTTGGGCC TGAGGATAAT AGAATCAAAG CACTGTTCAA AAGTTACCTT
31101 TCTCTACGTA TCAGTGTGGT TGTGTTATTA TTTGGAATAT ATTAACCCAT
31151 TTATGCCTAG TGTTCCATTA TTGGAATGCT AAGCTTGTGG AGTTATTTCT
31201 ATCCTACTGC TCAAGGTCAT TACCAAGGTC TGATTTTTCA CAAAACAAAT
31251 TTGCAACCTC CAGCATAAAT GGGTTAATAG TTGGTTCCTT TTTTTTTTTT
31301 TTTTTTTTTT TGAGACGGAG TCTTGCTCTT TCGCCCAGGC CGGAGTGCAG
31351 TGGCACTATC TCAGCTCACT GCAAGCTCTG CCTCCCGGGT TCACGCCATT
31401 CTCCTGCCTC AGCCTCCCGA GTAGCTGGGA CTACAGGTGC CCGCTACCAC
31451 GCCCGGCTAA TTTTTTGTAT TTTTAGTAGA GATGGGGTTT CATGGTGTTA
31501 GCCAGGATGG TCTCGATCTC CTGACCTCGT GATCCGCCCG CCTCGGCCTC
31551 CCAAAGTGCT GGGATTACAG GTGTGAGCCA CCGCGCCCAG CCTAGTTGGA
31601 TTCATTTTTA TTCCACTTTA GGGATTCCCT CTCATTCTTG CTGATTTCGT
31651 GTTTTGGTTT TGAGCGTTTT GTTATTGTTG CTGTTGTTTT GAATGTTTGA
31701 AACAACGTGG CTGGGCACAG TGTCTCATGC CTGTAATCCT AGCACTTTGG
31751 GAGGCCAAGG CAGATGGATT GCTTGAGCCC AGGAGTTTGA GACCAGCCTG
31801 GGCAACATGG CGAAACCTCT GTCTACAAGG AATACAAAAA TTAGCTGGGT
31851 GTGGTAGTGC ACACCTGAAG TCCCAGCTAC CTGGGAGGCT GAGGTGGGAG
31901 GATCACCTGA GCCCTGGGAG GTCGAGGCTG CAGTGAGCTG TGATCACACC
31951 ACTGCACTCC AGCCTGGCAA CAGAGTGAGA CTCTGTCTAA AAAAATAATA
32001 ATAATAAAAA AAATAAAAGA CATTAATGTA GCTCCAAAAG TCAGAACTAT
32051 ACAATACAGT AACTCTCCCT TTTGCCCTGT TTTCTTCCCC TACCCCCTTG
32101 TAGGTAAGCA GTCTCGTTCA CTTCTGGTTC CTCCTTCCTG GGTTTCGTTT
32151 AGCACAAACA GGCAGACACA AGTATGCTAT CTTCCCTTCT TTCTCACAGC
32201 AAGAAGTAGT ACCCTAGACT ACTCTGCTTT CCTTTTGCAT TTCTTCAGTT
32251 AACAATTTAT TAGGAAAATG ATTCCACATT GGTTTGTAGG ATCTTCCTCA
32301 TTTTTAAAAC CACTGTATCA GGGCTGGGCT TGTAATCCCA GCACTTTGGG
32351 AGGCTGAGGC GGCCGAATCA CGAGGTCAGG AGTTCGAGAC CAGCCTGGCC
32401 AACATGGTGA AACCCCTTCT CCACTAAAAA TACAAAAATT AGCTGGGCGT
32451 GGTGGCACAC ACCTGTAATC CCAGCACTTT GGGAGGCCAA AGCAGGCGGA
32501 TCACTTGAGA CCAGAGTTCA AGGCCAGGCC GGCAACATG GTGAACCCC
32551 ATCTCTACTA AAAGTACAAA AATTAGCCAG GTATGGTGGT GGGTGCCTGT
32601 AATCCCAGCT ACTCGGGAGG CTGAGGCACA AGAATAGCTT GAACCCGGGA
32651 GGTGGAGGTT GTAGTGAGCC AAGATCACGT CACTGCACTC CAGCATGGGC
32701 GACAAAGTGA GACTCCATCT CAAAAAAATT AATAAATAAA TAATTTAAAA
32751 ATTTTTTTAA AAGCCTCTGT ATCAGATCCC ATTATGTGGA CATAGCATGG
32801 TTTATTCAGC CAATCTTCTA TACATGGGCA TTTAGGTTTC CAGTTTTACA
32851 ATTACAAACA CTACTGCAAG GGCTGATCGT GCATAAACCT ATTTTTGTGT
32901 TGTGAGAGGA GTGCCTGCAG GGTGAATTTA GGGGTAATTG CACATGTGGT
32951 TTTGTTAGGC ACCACCAGAT TTCCCTCTGT TGGGTCTGTA CCAGTATGTG
33001 TTTCCACCAG CAGCTTTTCA GAACCTCTTT TCCCACAGCC TTACTAACTA
33051 AATGTGCCAT TACACGCTTG AGTTTTTGCC AGTCCAGTAG AGGAGAATGT
33101 ATTGCAGTGG AGTTTTAATT TACATCTCTC CTTTCTGAGT GAGGTGGAAC
33151 ATTTTTCAGA TGCTTAAGGG CCATTTATTT ATTTGTTTAT TTATCGGAGT
33201 CTCACTCTGT CACCCAGGCT GGAGTGCAGT GGCACGATCT CGGCTCACTG
33251 CAACCTCCGC CTCCCAGGTT CAAGCAATTC TCCTGCCTCA GCCTCCCAAG
33301 TAGCTGGGAT TACAGGCGTG AGCCACTGCG CCCAGCCCTT CCCAGTCTCG
33351 TTGAGACGTG GCTTGTAAGG ATGTGATGCA AGGTGTGAAC CTTCCCCAGA
33401 AAGAAGTGCA TACGCACAGC ACAGCCTGGC TGCAGCATCT GCTTCAAACA
33451 AAACAGTTAG CCGAGCTCCA CTTTCTTTGA CTTAATCATT CTTCATGCTC
33501 CACCCATTTC CGGAAAGATG TGAGGCATCC CTCTGATGCT GAGCGCAAGT
33551 CTGTGCACCT CTTTGCCTTT TTGTATGTTG TGCTATGTTG CGTCCAATTT
33601 GTGGCAGTTG TTTTCTGTTT TCCTGCTACA GATCTAGGCA GTACTGACCT
33651 GGGATGGGGA AGCAGGACTC TCTGGCATGG TCTTTATGCT ACCCCAGGGA
33701 AATCTGGGAT AGTTGAAATC TGAGCAGTAA TGTCCCTTCG CCATGTGTCA
33751 GGCAGAAGCT TGGGACTAAA TAAGCTCTGT TCAGCATGTG TGGGCACAGA
33801 GGGGACAGTG CAGACAGACT GCAGCTTTAT GCTTACTTGG ACACATTCCT
33851 TGACCTCTTG GAGGTTCTAT TTTGTTGCCC AGCATAGAAG CAGCACTCCT
33901 GTGTTGAAGT GATGAAGAGA ACAGTGTCTG GAGCCAGACC ATGTGGATGA
33951 AATTCAGGTT CCAGCGTGTT GGAGCCATGT AATGCCTGGT ACCGTCTGTG
34001 TCTCAGTTTC TCGAACTTCA TAAGTGACTT AAGATGTGAG AACTCTCAGA
34051 ACAGTGCCTA GCACATAGTG GACGCTCAGA AATTGTTAGC TTTTATCATC
34101 ACCAACCACA TAATCCATAT TTGTGGGATA TTGTGAGGTT TAACTCAAAT
34151 CATACAAAGT GTTCATCATA TGTGCTCCAA ACATTTTAAT CCATTAAAAT
34201 GTTCACTAAC AGATTTTTAG GCCGGGCACG GTGGCTCACG CCTGTAATCC
34251 CAGCACTTTG GGAGGCTGAG GCAGGCGGAT CACCTGAGGT CAGGAGTTCG
34301 AGACCAGCCT GAAACCCCGT CTCTACTAAA AATACAAAAA TTAGCTGGGC
34351 GTGGTGGCAT ACGGAGGTTG AGGCAGGAGA ATCGCTTGAA CTTGGGAGGT
34401 GGAGATTACA GTGAGCCCAG ATCGTGCCGC TGCACTCTAG CCTGGGTGAC
34451 AGAGAGACTC CGTCTCCAAA AAAAGAAATA GATTTTTAGA AAATCTTTCA
34501 CTTTTCAGGA AGAAAGCTTA TAGTCTCTGT GGCTCTGTGT TGAGGAAACA
34551 GCATTAATCT CACTACAGGA GACTGCTTCA CTATCAGTTA TTTCTACGTG
34601 GAAATATCTT GATTCCCAGT ATCATTCTGT CCTGAGCCCA GCACATCCCA
```

FIGURE 31

```
34651 GGCTGCCCAA ATCTTGCCAT GCTCTCCTTT GAGCCAAGCT GATCTTAGCT
34701 TCTCTCGAAA GTTTCTGAAT TGTCCCCCAT ATGGTCTCCC AGACTCTTCA
34751 GTTGAAAAAA GGAGCCCTCC CTGACAGCCC AGGGGTCGGT GCCTGCTCAT
34801 GGGAAGGTGG TTGCTGTTGA AAGCAGTTAT GAGCTTACTG TTCACTCAAC
34851 TCAGTGGCCA CCTGACCCTT TATGGTGCAT GCAATTTTAC CATGTACTTA
34901 TGGCCAAGCA CTACATAGTC AACAGACCTC ATTAAGTTGT CAAAAAGCAT
34951 TCTCAGGCTG AGGACGTTAG GCAACCTGGC TTTAGTTGGC AGAGGTGCGT
35001 GGACACTGCC AAGGCTCCTA TTTCTGGTTC CAGTGGATGA GGTGGAGGAG
35051 GATTATTTGT AATAATAGCA AACAGCCAGG TGCGGTGGCT CACACCTGAT
35101 AATCTCAACG CTTTGGGAGG TGGAGGTGGG AGGATCACGA GCCCAGGAGT
35151 TTGAGGCCAG CCTAGACAAC ATGGTGAGAC TCCATCTCTA TGAAAAAATT
35201 AAAAATCAGC TGGGTGTGGT TGCGCGTGCC TGTAGTCCCA GCTACTCAGG
35251 AGACTGAGGC GGAAGGAACC CTTGAGCCCA GGAGTTCAAG GTTACAGTGA
35301 GCTATGATCG CACCACTGTA CCCCAGCCTG GGCAACAGAG TGAGACCCTA
35351 TTTCTAAAAA GAGATAATAA TAGCAAACAC ACATTGAGTT CTAACCAGGT
35401 GCCAGGCAGT ATACTGAGGG CTTAAATGCA GCATCATGTC TGTTTCTCAC
35451 AGCAACCCTA CAAGGTAAGT GCTTGTGATT TCTACATTGT ACAGATGAGC
35501 AAGAGAGATT CAGTAACATG CCGAGGTCTT GTAGAGGGCA CAAATGCAGC
35551 CCCACAGTCT CACAGCAGAG CCCGCAGCAC TGCACCACAC TGACGCCTGA
35601 GCAAAGTTCA CTCCCTGACT GGAGAGCCAC AGAGGCACGA CCGAAGGTCA
35651 GGGGACAGGG TTTCCTAGCA TCCGCGAGCC TTACAGAAAG GCAACTGTGC
35701 AGTGCTCCAG CTGGCTTTCT CATGGAGAGT CAACAGAGAC ATTTCCCCTC
35751 CAGTAGAACA CAGACCGTCT CTCCCCTCCC CCTTGTTGGT TTTACCCAGG
35801 CTTTGTTTTC TGAAAATGTG GCTGGGCCTG CTTAACATGC TTAGCAGGGC
35851 ACTGGGAAAT GCACTTCAGT GGCCGGTGCC AGCTAGCTTT TTGGAGTTTT
35901 AAAAAGACTT TCAGAAGTCT TATTTCTCCC CCATTGAAAG GAGGGAAAAG
35951 GGTTTTTATA CAGTTACTTC TTTTGAGAGA AATGTGGAAA CAGTGGGACC
36001 AGTGAAGTTC CTTCCGATAA TGAAAGAGCG ATATCTGTGT CTGAAGCAGG
36051 AGGCTTGAGA TGATTTTTAT GGACACACCA AGAAATAACT GCATTCAGAA
36101 ACAGGTGAAA TTCCCAACGA TGATGAAAAG AAAGGACTAC AGATGGGAAA
36151 ATTGTGTGTG ATTACATTAG TATCTCTTCC TGAAATGAGG GATACATTGA
36201 TAGAGATGAT TAAAGCCAAC AGTAATCGGG CTAGCTTGCC GAGTGCTAGA
36251 AGTCAGTATT TCACAGATGG GGGTCCGTTT CTTTTGCATG TCAAGAAGGT
36301 TTACTTAGCA TGTTACCAGC AGAACTAGTC CAGTTGTAGC TCAGTTTTTC
36351 CTAAGCAGTG GGAAAGGCTG CTTATCCTGT CTGAAAGCAG GGGTTGGAGA
36401 AGGAGAATTT TCTTAGAATT TAACAACACA ATCTGAGACT GAAATTCTTG
36451 ACTGGAAATG CGGTTTTGTA CATGCTTGGT GTCCCTCTGA TGTCAGCATC
36501 TCCTGAGTGT GTATAATCTA GCCCCGCTGC CTCCTATTTT AAGGAATTCC
36551 TTCAGCCAGG GGTCAGCTGC TTTGTTGCTG CCTGGAAGCA GCTTATCTCA
36601 GAATGCTCTT TCTGTTTCAG GTCTCTGTTC TAGGATGTCC CGACCCAGTG
36651 GTGCATGAGA TCGCCTATCA GTACGGAAAA AATGTAGGAA TAGCTTTTCA
36701 GGTTAGTATG CTTTTTATTT GTAAGAATGG TGGCGTAGTG ATACAGTCAG
36751 CATTCTCCCC TAGTGTGTAA TCGTCAAAAT AGTAAGAACG ATGCAGCAG
36801 TGTTGGCATG GCGGTGCTCC TTACATCCCA TTTTTCCTTT TGCCAGCTAA
36851 TAGATGATGT ATTGGACTTC ACCTCGTGTT CTGACCAGAT GGGCAAACCA
36901 ACATCAGCTG ATCTGAAGCT CGGGTTAGCC ACTGGTCCTG TCCTGTTTGC
36951 CTGTCAGCAG GTAGGTTTTA CAAACTCCCT TTGACACATC ACTGCATAGC
37001 CCCACAGAAC TGATGTCCCG CGGCACAGCT GATGGGAAGA TTGCATAAAG
37051 GAATAGATGG GAAGGCATTC AGATAAGAGA TCACAGGTCT GCATTTGATC
37101 CTGGCTGAGT GAGATGTTGG GGCTGGTCAT TTCACCTTGC TAAGACTGTT
37151 TCCTTATCTG TAAAATTGAG AAGATCACCT TTCTCCCAGG GTGGTTGTGA
37201 GGATTAGCTA AGATCCTATT TGAGATCTTT GTGTCTTGTG GTGTGCCATA
37251 GGCATTTGAG GTAGCATCGT GATTATTTCC ATATATTTTG GCCACTGGCA
37301 AAGTGAACGG TTTCTAAGTC TTGATTATAG GACTGGACTT TGGTGGTCCT
37351 CAGAGCCCCT TAAAAGGCAT AGGAAGCATC AAGGGCCTCC AAGCATAAGA
37401 AATTCTCCGG TTCTAGAAGT TTAATGAGAC TCTGCTGCTC TGAGAGAGGC
37451 TTTAGAACCT CGGCCATTGC CTCAAAATGT CAGGAAGTCA GTGGAGTGCA
37501 GTAGACCCAC ATAGTTCCTT CTTTCTCCGG ATTGAGGGAC TGAGTCCCCC
37551 TTAATGTGAA TGAAAGGCTT AGGAAGCTTC AAAATGTTC CCTCGACTGA
37601 CAAAGCAGAC ATTCTCACAG CCTCCTCCAG ACCCTGCCAC ATGGCTTGTG
37651 GCTGTACTGA ATGTTACTTG AAATAAGTGA GACATTAGCT GGTGTTGGAA
37701 CATCTCGTTA ATAGATTTTC ATCTTAGTAG TATTTAATTT GTTATGTTGC
37751 AAAGCAGTAA GATGTTCATC ACCGTGCCAT GAAATTCAAC ATTAGCTCTT
37801 TGGTGTAAAA TTATAGTAAC TTTTGGTCTT TCAGAGATTT TGCCTCTATT
37851 CTGTCTTCAC GTTTACAAAG GTCAGTCATG TCCTCCATAA AATTCAGTGA
37901 TTCCACTGTG ATACAGAAAC CACGGCCCTT GCTTTTGGTG GGTTTCTGAT
37951 TGGAGAGAGG AAAGTCATC TTTCACCCAC TATCTAGCAT AGCCATTGGC
38001 AGCATGATTC TTCCCAGGGG AGGCTGACGT TCTGGGTGGC TGGACCAGGC
38051 TACTTTGGCA GCTTGCTAAG GCTATGAATG GAGATGTTGG GGTACTCGGT
38101 AGGAACACCC GCCCTCATTA TTACAAGGCT TCCATCCTCT CAAACTTTGG
38151 AGGCTGAGGT AAGAAGTGAA AGGTATGCTG TAAATAGGTC CTCTCTCCCA
38201 ATGAGGCTTA CTTGCCAGCC CAAAATCAAA GAGTATAATA CATGTGCCCA
38251 GTTTTGACAA AAATTTATAA AACCTCCTTT TGTACATTAA GGCAAGAGTG
38301 AGGAACATTT GAGCCATGTA GGTGTTATGC TGGGGATTAG AAAAATGAGG
38351 CACTGGCTAC CAGTAACCTA TATAACTGCG AACATTACTT CTCAGATACT
38401 TGTTAGTAAA CATGAGTGAA GGAAAGCAGA ATGGACTGAG TGTGCTGAAA
38451 TCCAGCTAGC TTGGTAAAGA TTCCTTTACC TAGGCTCAGA TTATCAGGAT
```

FIGURE 3J

```
38501 AAAAGGAAAA AGCCTTTTTC CCTGGAGAAG TCTATGAGAA AGTTTTGGTT
38551 GCTCTATTTG TAAAAATCTT CAAATTGTTA AGTACTTGTT ATGAACCCCA
38601 GGATACTAAG TTACCGGTTG AGTCCTACTT AAACCTTAAG GTGACTGGGT
38651 GAGAGGAGGC TGGCCTCTTC GGACTGTGTT TCACTCTGAA TATATTTCAG
38701 AAGAAACTAA CTTACTTTCC CCTACACACA CAAAGGAGTA ATGGCTATCT
38751 CTGCTTTCAT ATATAGTGGG GGAAAGGGGA AATGGACCTC TGCATAGTAT
38801 CTGTCAGTAA TCTACAAGAG ACTGAAAAAT GCTGGTTAGG CGGTGGCTCA
38851 TGCCTGTAAT CCCAGCACTT TGGGAGGCTG AGGCAGTTGG ATTATGAGGT
38901 CAGGAGTTCA AGACCAGCCT GACCAATATG GTGGAAACCC CGTCTCTACT
38951 AAAAATACAA AAATTAGCCG GGCCTGGTGG TGCATGCCTG TAATCCCAGC
39001 TACTCGGGAG GCCAAGGAAG GAGAATCCTT GAACCTGGGA GGCAGAGGTT
39051 GCAGTGAGCC GAGACTGCAC TCCAGCCTGG GTGACAGAGT GAGACTCCGT
39101 CTCAAAAAAA AAAAAAAAGG CTGGTTAAAA AAAGCAAGCA AAAGGAAAAA
39151 AAAAGATTAC TGTACCCGAA GCCATGGTTT TATGTGTGCT TTGCTGGGAA
39201 ATCCCAGTCA TGAGGCACCT ACTCATGCTC ACCAGACAGC AGTGTTCTCA
39251 TCTGCCCATA AGGCAGTGAG TTGAAAAGGC ACATTGCAGC CTCAGAAAAG
39301 GGAACACAGA ATGGAGTCCA AGCAGGAAGT GACTCTGGAC AGGACTCATT
39351 TCAAAAGTAG ACTGATGTTT CTGTCTTGTG GCACATGGGC CAGAAGTTAG
39401 CCAAGTATGT ATTTATAAGT TGCCTTCTAA TAAAACAGCA AGGTTAGGCT
39451 CTTTTGTGGA ATACACTGTA AAACAAGAGA TTCTTAGCAA GAAATGTGTC
39501 AAAAGATATA TGGGACTAAG ATTAATTCAG GTAAAAACAA GTTCCAAAAA
39551 TAACGTAAGA ATATGCAATA TCTCCACTTA ATGAAAATGT GTTTTTAGTT
39601 TACAAAGGAT TCTTTCATAC ATTATCTCTA ATCTCACAAC TCCTCTTTGT
39651 GGTAGATATT ATGGTGTTTA TTCTGCAAGT AAGAAACTGA TGCCCAAACC
39701 TCGCCAAAAT TAAACATCTG GTAAATGGCA CAGCAGGGAA CTGAACAAGT
39751 CTAAGACCAG TATTCATTTT ATTACATCAT ACATAGTGTT ATTGCCACTG
39801 GTAATGCTGA GAAGTTAGTA GCTATGATAC CACACAGGCC TTCCCACAGA
39851 GCAGGTAACT AACCCACCTG GGCACTGACG ATACTCAAAG AATCATCTCT
39901 GTGTCATGTC TTTGCTATTG TAAACAACAT ACCTACTTGG TGGAGTAGTT
39951 CTAAGACGTC TGTAATCCTT TCCCTTTGGT AG
(SEQ ID NO: 3)
```

FEATURES:
Start: 2201
Exon: 2201-2367
Intron: 2368-3951
Exon: 3952-3952
Intron: 3953-6692
Exon: 6693-6725
Intron: 6726-9189
Exon: 9190-9254
Intron: 9255-9798
Exon: 9799-9907
Intron: 9908-14148
Exon: 14149-14279
Intron: 14280-21593
Exon: 21594-21735
Intron: 21736-25190
Exon: 25191-25302
Intron: 25303-25398
Exon: 25399-25516
Intron: 25517-28760
Exon: 28761-28768
Intron: 28769-36633
Exon: 36634-36701
Intron: 36702-36846
Exon: 36847-36981
Stop: 36982

SNPs:

| DNA Position | Major | Minor | Domain | Protein Position | Major | Minor |
|---|---|---|---|---|---|---|
| 2658 | G | C | Intron | | | |
| 3300 | G | A | Intron | | | |
| 4697 | - | T | Intron | | | |
| 4703 | - | T | Intron | | | |
| 4985 | A | G | Intron | | | |
| 7837 | T | C | Intron | | | |
| 7874 | - | T | Intron | | | |
| 8299 | C | T | Intron | | | |
| 8916 | A | G | Intron | | | |
| 8938 | A | G | Intron | | | |
| 8974 | A | T | Intron | | | |
| 9182 | T | - | Intron | | | |
| 9309 | G | A | Intron | | | |

FIGURE 3K

| | | | |
|---|---|---|---|
| 9312 | G | A | Intron |
| 9321 | A | T | Intron |
| 9539 | C | A | Intron |
| 9545 | A | G | Intron |
| 9734 | A | C | Intron |
| 9929 | G | A | Intron |
| 9996 | C | T | Intron |
| 10234 | G | A | Intron |
| 10316 | C | G | Intron |
| 10565 | G | C | Intron |
| 10622 | C | T | Intron |
| 10839 | T | C | Intron |
| 11006 | C | T | Intron |
| 12853 | T | C | Intron |
| 13471 | C | T | Intron |
| 13500 | A | G | Intron |
| 13507 | A | G | Intron |
| 13554 | C | A | Intron |
| 13737 | T | C | Intron |
| 13940 | T | C | Intron |
| 15427 | A | G | Intron |
| 15486 | C | G | Intron |
| 15648 | G | A | Intron |
| 15650 | T | C | Intron |
| 15840 | - | A | Intron |
| 17726 | A | G | Intron |
| 17736 | G | A | Intron |
| 18850 | T | C | Intron |
| 19419 | - | G | Intron |
| 19429 | G | - | Intron |
| 19431 | G | - | Intron |
| 22516 | T | C | Intron |
| 22543 | T | C | Intron |
| 23568 | A | G | Intron |
| 23779 | A | G | Intron |
| 23808 | A | G | Intron |
| 23979 | C | T | Intron |
| 24319 | C | T | Intron |
| 27647 | A | T | Intron |
| 29477 | C | T | Intron |
| 34277 | A | G | Intron |
| 35207 | C | T | Intron |
| 37162 | G | A | Beyond ORF(3') |
| 38111 | G | A | Beyond ORF(3') |

Context:

DNA
Position

2658 CCGCGCGCAGGTGAGGTTGGGAGGCGCGCGCCCGGCGGGGCTCAGAGGTCACGGCTCCAA
TGACAGCAGTGGGCGGAATGAATGGGAGCGGGGAGCACGTGCGTCGCGACGCGGGGGCGC
GCGGGGTAGCTCCGGGGTAGCTCCGGGGTGGGACTCCGGAGCTGAGGGGTGCTCGCGGTG
GGACGGAGCCGCGCGTTGGACTGAAGTAGGGGCGCCCTACACGGGGTTGCAGAAAGCGGT
GTCCTGGGGACCCCGGGAGCGTTTTGGGGGGTGGAGAAAGCGGTGGGATCCGTGTCCTGG
[G,C]
GGAAGCGCAGGAGCGATCAGATTGACCGCTGCTATATGGACAAGGTTAATTAAGCCTGGA
GAGCGACTGCAGCTATTTACTTTGGAGTTAGAGGAAGACAGATCTTGCCTGAAATTTTAG
AGCCAAAGTGCTCAGAGCTCTCTCCGAGAAACGGAGGATCGAATCGGCCTCGGAATAGTC
CGAAAAGGTCTTGTGGAGAATGCAGGGCTGGTGCTAGGGTGGACCGGACCTTAGTTGTCC
AGCAGTGGCTTCGGGAGGAGAGCACACCTGGATGGGGCTGGAATGACACTGGAAGGAGAA

3300 TAAAGTCAGAATCTCAGTGATAGCCCATTCTTTCAGGGTCTCCTCTGCTGCCTTTGGGTT
CCGATCTCCTTTTTCTCCCTTTCTGGTCAGTTTAGCCCCTGTAAATGGACACTGTGAGCC
CTTCTGCACTTTGTAATGATTCTCAGTGTGCCATGGGGTAGGCCCATGCTATTAGCATAA
CCGTGCAAAATCTATGGACTCACTGTTACTTAAGTTTATTTGAATTTAGTACTCTTTTAA
TTCAGATTTGGTATACTTTATGTGTCCGTGTTCTCATCAAACATCATTTCCCAGTATGAA
[G,A]
TATATAACACTTATAAATATCTACTTTGTACCAAAGTAGATGCGTATCACAAATTATCCA
AAACAAGGCTTGGGCCAGGCACAGTGGCTCACACCTGTAATCCCAGCACTTTGGGAGGCT
GAGGTGGGAGAATCGGTTGAGGCCAGGAGTTTGGGACCAGCCTAGGCAACATAGCAAGAC
TCTGTCTCTATAAAAAAATAGAAAAAATTCACCAGGTGGGGTGGTGCATGCCTGTAGTTCT
ACCTACTCAGGAGCCTGAGGGAGGAGGATTGTTCGATCCCAGGAGTTCAAGATTACAGTG

4697 GATGCCTTTCACTATACGTTAATATGTTAGCATTCTGGTGTCTGCCTCAGGCATGTGTAT
TTTGGTTACTTCAAGTCTCTTAGGGCCTGATAGTCCTTGGGGACACAGAACTACAATAAC

FIGURE 3L

```
           TAAGCCACAGGGACAAAGAGCGGCAATAATTAAGCCACGTCTTGCTCTCCACCAGAGCTC
           TACTACCTCCTAATGGTTGTACATTCTTCTGACTTCACTAGTAGTGTGAACAAATATTGT
           AATACAATAAAAACCAGTGTGCATGTGATCGTGCCAAATCACTTCTCAATATATCTTTGA
           [-,T]
           TTTTTTTTTTAATTTATTTTTTTAGAGACGGGGACTTTTTGTGTTGGCCAGGTTGGTCTT
           GAACTCTTGGACTCAAGCCATTCCCCCCTCCCCCCCACCCCGCTTGAGGATTGGCACACG
           GCCATGTATTTGATTCTTACCCAGCACTTTCTCTTTAGCTGAGCGTGGTGGCTCACGCCT
           GTAATCCCAACAGTTTGGGAGGCCGAGGCAGGAGAATCCCTTTAGCTCAGGAGTTCGAGA
           CCAGCCTGGGCCACTTAGTGAGACCTCCTGATACGGTTTGGCTCTGTATGCCCACCCACA
4703       TTTCACTATACGTTAATATGTTAGCATTCTGGTGTCTGCCTCAGGCATGTGTATTTTGGT
           TACTTCAAGTCTCTTAGGGCCTGATAGTCCTTGGGGACACAGAACTACAATAACTAAGCC
           ACAGGGACAAAGAGCGGCAATAATTAAGCCACGTCTTGCTCTCCACCAGAGCTCTACTAC
           CTCCTAATGGTTGTACATTCTTCTGACTTCACTAGTAGTGTGAACAAATATTGTAATACA
           ATAAAAACCAGTGTGCATGTGATCGTGCCAAATCACTTCTCAATATATCTTTGATTTTTT
           [-,T]
           TTTTAATTTATTTTTTTAGAGACGGGGACTTTTTGTGTTGGCCAGGTTGGTCTTGAACTC
           TTGGACTCAAGCCATTCCCCCCTCCCCCCCACCCCGCTTGAGGATTGGCACACGGCCATG
           TATTTGATTCTTACCCAGCACTTTCTCTTTAGCTGAGCGTGGTGGCTCACGCCTGTAATC
           CCAACAGTTTGGGAGGCCGAGGCAGGAGAATCCCTTTAGCTCAGGAGTTCGAGACCAGCC
           TGGGCCACTTAGTGAGACCTCCTGATACGGTTTGGCTCTGTATGCCCACCCACATCTATC
4985       ATATATCTTTGATTTTTTTTTTTAATTTATTTTTTTAGAGACGGGGACTTTTTGTGTTGG
           CCAGGTTGGTCTTGAACTCTTGGACTCAAGCCATTCCCCCCTCCCCCCCACCCCGCTTGA
           GGATTGGCACACGGCCATGTATTTGATTCTTACCCAGCACTTTCTCTTTAGCTGAGCGTG
           GTGGCTCACGCCTGTAATCCCAACAGTTTGGGAGGCCGAGGCAGGAGAATCCCTTTAGCT
           CAGGAGTTCGAGACCAGCCTGGGCCACTTAGTGAGACCTCCTGATACGGTTTGGCTCTGT
           [A,G]
           TGCCCACCCACATCTATCTCGAACTGTAATCCCCAATTACATTTGGGGACCAGGGAGGGT
           CAAGGGAGGGACCAGGTGGAGGTAATTGGATCATGGGGGTGGATTCCCCCATGCTGTTCT
           CATGATAGGGAGTTCTCACAAGATCTGCTGGTTTTATAAGTGTTTGGTAGTTCCTCCTGT
           GTTCATTCTGTCTCCTGCCGCCTTGTGAAGAAGGTGCTTGTTTCTCCTTCTCCTTCTTCC
           ACCATGATTCTAAGTTTCTGAGGCCTCCCCAGCCATTCAGAACTGTGAGTCAATTAAACC
7837       AGCAGAAAATAGTAGCTTGATTGAATAGATACTGTATTAAATGTATATTGTGTACCAGGC
           TCTGAGCTAAGAGCTTTACATCTGCTCTCTAAATTAATCTCCACCTCTCTCCATGAGTAG
           GTATTATCAGAAAGACATCACAAGGTAACACAAATGTTGAGATTTGAACCGAGATCTGTC
           TTCCAAAGTCCATGCTACTAATAATTGTTAGGCCACTTGGTGGTAAAAAGCGTCCCCTGT
           ATTAATTAGCTGTGTAATTTTAATCCTTCAACCCAGATTAGGGGTCTATAACTGAATAAC
           [T,C]
           AAAAAGTTATTCAGTTAGAATAGTTCAGTTAGTTATTAACTAATCATAGTTATTTGGTCA
           AGCGCAGTGACTCACGTCTGTAATTCCAGCACTTGGGGAGGCTGTGGCAGGAGGATTTCT
           AATAATAGTAACTATTACTAGAGACCTGATAATAATTATTAAGTCTCTTACTGAAGAAGT
           TTTACTCTTCCATTAAGATGCCCTTATTTATAAGTATTATAATAAAATACTGAACTCATA
           TGAATTAATTACCCATGTAGACTGAAAGACATAGGTTGTCATATAATGGTTGTCATATAA
7874       TAAATGTATATTGTGTACCAGGCTCTGAGCTAAGAGCTTTACATCTGCTCTCTAAATTAA
           TCTCCACCTCTCTCCATGAGTAGGTATTATCAGAAAGACATCACAAGGTAACACAAATGT
           TGAGATTTGAACCGAGATCTGTCTTCCAAAGTCCATGCTACTAATAATTGTTAGGCCACT
           TGGTGGTAAAAAGCGTCCCCTGTATTAATTAGCTGTGTAATTTTAATCCTTCAACCCAGA
           TTAGGGGTCTATAACTGAATAACCAAAAAGTTATTCAGTTAGAATAGTTCAGTTAGTTAT
           [-,T]
           AACTAATCATAGTTATTTGGTCAAGCGCAGTGACTCACGTCTGTAATTCCAGCACTTGGG
           GAGGCTGTGGCAGGAGGATTTCTAATAATAGTAACTATTACTAGAGACCTGATAATAATT
           ATTAAGTCTCTTACTGAAGAAGTTTTTACTCTTCCATTAAGATGCCCTTATTTATAAGTAT
           TATAATAAAATACTGAACTCATATGAATTAATTACCCATGTAGACTGAAAGACATAGGTT
           GTCATATAATGGTTGTCATATAAAGCATGAAGGAGGATTGTCACTTTGTTTTCTTGTTGC
8299       AGTCTCTTACTGAAGAAGTTTTACTCTTCCATTAAGATGCCCTTATTTATAAGTATTATA
           ATAAAATACTGAACTCATATGAATTAATTACCCATGTAGACTGAAAGACATAGGTTGTCA
           TATAATGGTTGTCATATAAAGCATGAAGGAGGATTGTCACTTTGTTTTCTTGTTGCACTG
           TAATTGCCTGGGATATCATGAAAGTTCTTACTGGTTTAATGAATATGTAATGCTGTGGGG
           GAAAGAATGAAACTCAGGCCAACTACTTTGACTGGTGTCTGGCAAAGTCAACTTTCATTG
           [C,T]
           CATTTTAATATGGCGCCGGGCGCGGTGGCTCACGCCTGTAATCCCAGCACTTTGGGAGGC
           CAAGGCGGGCGGATCATGAGGTCAGGAGATCGAGACCATCCTGGCTAACACGGTGAAACC
           CCATCTCTACTAAAAATACAAAAAATTAGCCAGGCGAGGTGGTGGGCGCCTGTAGTCCCA
           GCTACTCAGGAGGCTGAGACAGGAGAATGGCGTGAACCCTGGGGGGCGGAGCCTGCAGTG
           AGCCGAGATAGCGCCACTGCACTCCAGCCTGGACGACAGAACGAGACTCCGTCTCACAAA
8916       TATGGCTAGAGCAATACATGTTCATTAGAGAAGAATCAGAAAATATCTACCAAAAGAAGG
           AATAAAACAAAACACCCCCACAATCCGATTCATTCCAGAATAACTACTTTTAACACCCTG
           GTTTGTGTGCTTTCAAACTCTGTTCTCCCATTTCCAAAGGATGTTGAGGAACACGAACTT
           AAAATAGACAGTGTTTGTATAAATATAAATTCCTTCCTTGCTATTGAAATCTTTTTTTCCT
           CTGACCAATCTTAGTTAAATGGAAGGAAATTGTTTTAAAACTAATTTTCAGGTCTGGAAA
           [A,G]
           ATAGATATGAATATGGAAATGACTTTCTTTGGGGGAAGGGATGGACTGAAGATGGTTATT
```

FIGURE 3M

```
      ATTTTCTCCTTTTTTCTTATTTATGTTTTCTGCAATGACAAGTATTTTGTAATAACAAAA
      GGAAACTTTAAAATTATTCTTCCTCTAAAGTTTGCAATCTACCTGTAAATGGGTGATTAG
      AAGATAAAGATTATAATTATGGGGGTTTTATCATCCAATGTTACAGTTTTTCAGGAATAT
      TCTTACAAGTTTCTTGACATTTTTATTTTATAGATACCCTATATTAATCTTGTGAAGCAT
```

8938
```
      CATTAGAGAAGAATCAGAAAATATCTACCAAAAGAAGGAATAAAACAAAACACCCCCACA
      ATCCGATTCATTCCAGAATAACTACTTTTAACACCCTGGTTTGTGTGCTTTCAAACTCTG
      TTCTCCCATTTCCAAAGGATGTTGAGGAACACGAACTTAAAATAGACAGTGTTTGTATAA
      ATATAAATTCCTTCCTTGCTATTGAAATCTTTTTTCCTCTGACCAATCTTAGTTAAATGG
      AAGGAAATTGTTTTAAAACTAATTTTCAGGTCTGGAAAGATAGATATGAATATGGAAATG
      [A,G]
      CTTTCTTTGGGGGAAGGGATGGACTGAAGATGGTTATTATTTTCTCCTTTTTTCTTATTT
      ATGTTTTCTGCAATGACAAGTATTTTGTAATAACAAAAGGAAACTTTAAAATTATTCTTC
      CTCTAAAGTTTGCAATCTACCTGTAAATGGGTGATTAGAAGATAAAGATTATAATTATGG
      GGGTTTTATCATCCAATGTTACAGTTTTTCAGGAATATTCTTACAAGTTTCTTGACATTT
      TTATTTTATAGATACCCTATATTAATCTTGTGAAGCATTTAACATCTGCCTGTCCAAATG
```

8974
```
      GGAATAAAACAAAACACCCCCACAATCCGATTCATTCCAGAATAACTACTTTTAACACCC
      TGGTTTGTGTGCTTTCAAACTCTGTTCTCCCATTTCCAAAGGATGTTGAGGAACACGAAC
      TTAAAATAGACAGTGTTTGTATAAATATAAATTCCTTCCTTGCTATTGAAATCTTTTTTC
      CTCTGACCAATCTTAGTTAAATGGAAGGAAATTGTTTTAAAACTAATTTTCAGGTCTGGA
      AAGATAGATATGAATATGGAAATGACTTTCTTTGGGGGAAGGGATGGACTGAAGATGGTT
      [A,T]
      TTATTTTCTCCTTTTTTTCTTATTTATGTTTTCTGCAATGACAAGTATTTTGTAATAACAA
      AAGGAAACTTTAAAATTATTCTTCCTCTAAAGTTTGCAATCTACCTGTAAATGGGTGATT
      AGAAGATAAAGATTATAATTATGGGGGTTTTATCATCCAATGTTACAGTTTTTCAGGAAT
      ATTCTTACAAGTTTCTTGACATTTTTATTTTATAGATACCCTATATTAATCTTGTGAAGC
      ATTTAACATCTGCCTGTCCAAATGTATGTCGTATATCACGGTAAGTTTACAGTCCATACT
```

9182
```
      AAATTGTTTTAAAACTAATTTTCAGGTCTGGAAAGATAGATATGAATATGGAAATGACTT
      TCTTTGGGGGAAGGGATGGACTGAAGATGGTTATTATTTTCTCCTTTTTTCTTATTTATG
      TTTTCTGCAATGACAAGTATTTTGTAATAACAAAAGGAAACTTTAAAATTATTCTTCCTC
      TAAAGTTTGCAATCTACCTGTAAATGGGTGATTAGAAGATAAAGATTATAATTATGGGGG
      TTTTATCATCCAATGTTACAGTTTTTCAGGAATATTCTTACAAGTTTCTTGACATTTTTA
      [T,-]
      TTTATAGATACCCTATATTAATCTTGTGAAGCATTTAACATCTGCCTGTCCAAATGTATG
      TCGTATATCACGGTAAGTTTACAGTCCATACTGCAACTACTAAAATTATCCATTTTTAAA
      TTTATTATTGTTTAAAAAATTTTTTTTGTAGCGATGGGGAGCTCACTGTGTTGCCCAGGC
      TGGTCTTGAACTGCTGGCCTCAAGCTATCCTCCCACCCTCAGGTTCCCAAAGTGCTGGGA
      TTGCAGACATAAGCACCCGGCCTAAAATTATTAATTATATTGCCTGTAAATTTCTATTCT
```

9309
```
      CAATGACAAGTATTTTGTAATAACAAAAGGAAACTTTAAAATTATTCTTCCTCTAAAGTT
      TGCAATCTACCTGTAAATGGGTGATTAGAAGATAAAGATTATAATTATGGGGGTTTTATC
      ATCCAATGTTACAGTTTTTCAGGAATATTCTTACAAGTTTCTTGACATTTTTATTTTATA
      GATACCCTATATTAATCTTGTGAAGCATTTAACATCTGCCTGTCCAAATGTATGTCGTAT
      ATCACGGTAAGTTTACAGTCCATACTGCAACTACTAAAATTATCCATTTTTAAATTTATT
      [G,A]
      TTGTTTAAAAAATTTTTTTTGTAGCGATGGGGAGCTCACTGTGTTGCCCAGGCTGGTCTT
      GAACTGCTGGCCTCAAGCTATCCTCCCACCCTCAGGTTCCCAAAGTGCTGGGATTGCAGA
      CATAAGCACCCGGCCTAAAATTATTAATTATATTGCCTGTAAATTTCTATTCTAAATTGT
      AGATCTCTGCCTATTCAAAAAACAGGAATATAATAAAGTTTGAGCTCAACCCAGAGCACA
      ATGAACATAGTTTAGTTTTTCTTTGATTTTGTGGGTTCTCAAGGCCCTATTTATAAAAGT
```

9312
```
      TGACAAGTATTTTGTAATAACAAAAGGAAACTTTAAAATTATTCTTCCTCTAAAGTTTGC
      AATCTACCTGTAAATGGGTGATTAGAAGATAAAGATTATAATTATGGGGGTTTTATCATC
      CAATGTTACAGTTTTTCAGGAATATTCTTACAAGTTTCTTGACATTTTTATTTTATAGAT
      ACCCTATATTAATCTTGTGAAGCATTTAACATCTGCCTGTCCAAATGTATGTCGTATATC
      ACGGTAAGTTTACAGTCCATACTGCAACTACTAAAATTATCCATTTTTAAATTTATTATT
      [G,A]
      TTTAAAAAATTTTTTTTGTAGCGATGGGGAGCTCACTGTGTTGCCCAGGCTGGTCTTGAA
      CTGCTGGCCTCAAGCTATCCTCCCACCCTCAGGTTCCCAAAGTGCTGGGATTGCAGACAT
      AAGCACCCGGCCTAAAATTATTAATTATATTGCCTGTAAATTTCTATTCTAAATTGTAGA
      TCTCTGCCTATTCAAAAAACAGGAATATAATAAAGTTTGAGCTCAACCCAGAGCACAATG
      AACATAGTTTAGTTTTTCTTTGATTTTGTGGGTTCTCAAGGCCCTATTTATAAAAGTGAT
```

9321
```
      TTTTGTAATAACAAAAGGAAACTTTAAAATTATTCTTCCTCTAAAGTTTGCAATCTACCT
      GTAAATGGGTGATTAGAAGATAAAGATTATAATTATGGGGGTTTTATCATCCAATGTTAC
      AGTTTTTCAGGAATATTCTTACAAGTTTCTTGACATTTTTATTTTATAGATACCCTATAT
      TAATCTTGTGAAGCATTTAACATCTGCCTGTCCAAATGTATGTCGTATATCACGGTAAGT
      TTACAGTCCATACTGCAACTACTAAAATTATCCATTTTTAAATTTATTATTGTTTAAAAA
      [A,T]
      TTTTTTTTGTAGCGATGGGGAGCTCACTGTGTTGCCCAGGCTGGTCTTGAACTGCTGGCC
      TCAAGCTATCCTCCCACCCTCAGGTTCCCAAAGTGCTGGGATTGCAGACATAAGCACCCG
      GCCTAAAATTATTAATTATATTGCCTGTAAATTTCTATTCTAAATTGTAGATCTCTGCCT
      ATTCAAAAAACAGGAATATAATAAAGTTTGAGCTCAACCCAGAGCACAATGAACATAGTT
      TAGTTTTTCTTTGATTTTGTGGGTTCTCAAGGCCCTATTTATAAAAGTGATCTATTGATC
```

FIGURE 3N

9539
TATGTCGTATATCACGGTAAGTTTACAGTCCATACTGCAACTACTAAAATTATCCATTTT
TAAATTTATTATTGTTTAAAAAAATTTTTTTTGTAGCGATGGGGAGCTCACTGTGTTGCCC
AGGCTGGTCTTGAACTGCTGGCCTCAAGCTATCCTCCCACCCTCAGGTTCCCAAAGTGCT
GGGATTGCAGACATAAGCACCCGGCCTAAAATTATTAATTATATTGCCTGTAAATTTCTA
TTCTAAATTGTAGATCTCTGCCTATTCAAAAAACAGGAATATAATAAAGTTTGAGCTCAA
[C,A]
CCAGAGCACAATGAACATAGTTTAGTTTTTTCTTTGATTTTGTGGGTTCTCAAGGCCCTAT
TTATAAAAGTGATCTATTGATCTGTCATTTAGCAAGAATAGAATTCTGTATGTTTTTCCA
AATTATAATGACCTTTTCAGATTCATGATTAATTTCTAGCAAATATTTGGGCTGAATTTT
CCGTATCTGAGTCTACTAAATATATATGTATATAAAACTTACTTGAAAATGAAGTCATGT
GCATTTTTGCATGTCCCAGGTTTCATCACACAACCCCAGACAGTAAAACACACAGTGGTG

9545
GTATATCACGGTAAGTTTACAGTCCATACTGCAACTACTAAAATTATCCATTTTTAAATT
TATTATTGTTTAAAAAAATTTTTTTTGTAGCGATGGGGAGCTCACTGTGTTGCCCAGGCTG
GTCTTGAACTGCTGGCCTCAAGCTATCCTCCCACCCTCAGGTTCCCAAAGTGCTGGGATT
GCAGACATAAGCACCCGGCCTAAAATTATTAATTATATTGCCTGTAAATTTCTATTCTAA
ATTGTAGATCTCTGCCTATTCAAAAAACAGGAATATAATAAAGTTTGAGCTCAACCCAGA
[A,G]
CACAATGAACATAGTTTAGTTTTTCTTTGATTTTGTGGGTTCTCAAGGCCCTATTTATAA
AAGTGATCTATTGATCTGTCATTTAGCAAGAATAGAATTCTGTATGTTTTTCCAAATTAT
AATGACCTTTTCAGATTCATGATTAATTTCTAGCAAATATTTGGGCTGAATTTTCCGTAT
CTGAGTCTACTAAATATATATGTATATAAAACTTACTTGAAAATGAAGTCATGTGCATTT
TTGCATGTCCCAGGTTTCATCACACAACCCCAGACAGTAAAACACACAGTGGTGAAAAAT

9734
AGCACCCGGCCTAAAATTATTAATTATATTGCCTGTAAATTTCTATTCTAAATTGTAGAT
CTCTGCCTATTCAAAAAACAGGAATATAATAAAGTTTGAGCTCAACCCAGAGCACAATGA
ACATAGTTTAGTTTTTTCTTTGATTTTGTGGGTTCTCAAGGCCCTATTTATAAAAGTGATC
TATTGATCTGTCATTTAGCAAGAATAGAATTCTGTATGTTTTTCCAAATTATAATGACCT
TTTCAGATTCATGATTAATTTCTAGCAAATATTTGGGCTGAATTTTCCGTATCTGAGTCT
[A,C]
CTAAATATATATGTATATAAAACTTACTTGAAAATGAAGTCATGTGCATTTTTGCATGTC
CCAGGTTTCATCACACAACCCCAGACAGTAAAACACACAGTGGTGAAAAATACACCGATC
CTTTCAAACTCGGTTGGAGAGACTTGAAAGGTCTGTATGAGGACATTAGAAAGGTGAGTT
TTTTATTCTGCTGTGATGTAATGTTTTAGCTTACCAAAACTTACTAAAATTTTATTTTAT
TTTTTATTCTTATAATTATTATTATTTTTTGAGCTGGAGTCTCACTCTGTTGCCCAGGCT

9929
TAGCAAGAATAGAATTCTGTATGTTTTTCCAAATTATAATGACCTTTTCAGATTCATGAT
TAATTTCTAGCAAATATTTGGGCTGAATTTTCCGTATCTGAGTCTACTAAATATATATGT
ATATAAAACTTACTTGAAAATGAAGTCATGTGCATTTTTGCATGTCCCAGGTTTCATCAC
ACAACCCCAGACAGTAAAACACACAGTGGTGAAAAATACACCGATCCTTTCAAACTCGGT
TGGAGAGACTTGAAAGGTCTGTATGAGGACATTAGAAAGGTGAGTTTTTTATTCTGCTGT
[G,A]
ATGTAATGTTTTAGCTTACCAAAACTTACTAAAATTTTATTTTATTTTTTATTCTTATAA
TTATTATTATTTTTTGAGCTGGAGTCTCACTCTGTTGCCCAGGCTTGAGTGCAGCGGTGC
AATCTAAGCTCACTGCAACCCTTGCCTCCCAGGTTCATGCAATTCTCCTGCCTCAGCCTC
CTGAGTAGCTGAGATTATAGGCATGCGCCATCACACCTGGGTAATTTTTGTATTTTTAGT
GAAGACGGGGTTTTGCTATGTTGGCCAGGCTGGTCTTGAACTCCTGACCTCAGGTGACCT

9996
TAGCAAATATTTGGGCTGAATTTTCCGTATCTGAGTCTACTAAATATATATGTATATAAA
ACTTACTTGAAAATGAAGTCATGTGCATTTTTGCATGTCCCAGGTTTCATCACACAACCC
CAGACAGTAAAACACACAGTGGTGAAAAATACACCGATCCTTTCAAACTCGGTTGGAGAG
ACTTGAAAGGTCTGTATGAGGACATTAGAAAGGTGAGTTTTTTATTCTGCTGTGATGTAA
TGTTTTAGCTTACCAAAACTTACTAAAATTTTATTTTATTTTTTATTCTTATAATTATTA
[C,T]
TATTTTTTGAGCTGGAGTCTCACTCTGTTGCCCAGGCTTGAGTGCAGCGGTGCAATCTAA
GCTCACTGCAACCCTTGCCTCCCAGGTTCATGCAATTCTCCTGCCTCAGCCTCCTGAGTA
GCTGAGATTATAGGCATGCGCCATCACACCTGGGTAATTTTTGTATTTTTAGTGAAGACG
GGGTTTTGCTATGTTGGCCAGGCTGGTCTTGAACTCCTGACCTCAGGTGACCTACCCGCC
TTGGCCTCCCAAAGTGCTGGGATTACAAAAAAACAGTGCAGGTTTTCAGATCTGTACAAT

10234
AATGTTTTAGCTTACCAAAACTTACTAAAATTTTATTTTATTTTTTATTCTTATAATTAT
TATTATTTTTTGAGCTGGAGTCTCACTCTGTTGCCCAGGCTTGAGTGCAGCGGTGCAATC
TAAGCTCACTGCAACCCTTGCCTCCCAGGTTCATGCAATTCTCCTGCCTCAGCCTCCTGA
GTAGCTGAGATTATAGGCATGCGCCATCACACCTGGGTAATTTTTGTATTTTTAGTGAAG
ACGGGGTTTTGCTATGTTGGCCAGGCTGGTCTTGAACTCCTGACCTCAGGTGACCTACCC
[G,A]
CCTTGGCCTCCCAAAGTGCTGGGATTACAAAAAAACAGTGCAGGTTTTCAGATCTGTACA
ATGCAGTTTGCAATCTTGATTCACGTATGGTCAAGTTTCAAATGTTTCTTGAGAAGAATA
CATATGACCCAGTGCCAGGCAATATGAAGAATGCAATATGTATTTATGTCCAGAAAGAGG
TTATGGCAGGGTTGGGAACCTGAAGGAAAAAAATGGTCCAGGTAGCTCATGCTTGTCCAA
TGAGTTATCCCACCTTTCCTCTTAAAACCCACCACCTCCCAGTGACTCCAGCTGTCTCTT

10316
TCACTCTGTTGCCCAGGCTTGAGTGCAGCGGTGCAATCTAAGCTCACTGCAACCCTTGCC
TCCCAGGTTCATGCAATTCTCCTGCCTCAGCCTCCTGAGTAGCTGAGATTATAGGCATGC
GCCATCACACCTGGGTAATTTTTGTATTTTTAGTGAAGACGGGGTTTTGCTATGTTGGCC
AGGCTGGTCTTGAACTCCTGACCTCAGGTGACCTACCCGCCTTGGCCTCCCAAAGTGCTG
GGATTACAAAAAAACAGTGCAGGTTTTCAGATCTGTACAATGCAGTTTGCAATCTTGATT

FIGURE 30

```
       [C,G]
       ACGTATGGTCAAGTTTCAAATGTTTCTTGAGAAGAATACATATGACCCAGTGCCAGGCAA
       TATGAAGAATGCAATATGTATTTATGTCCAGAAAGAGGTTATGGCAGGGTTGGGAACCTG
       AAGGAAAAAAATGGTCCAGGTAGCTCATGCTTGTCCAATGAGTTATCCCACCTTTCCTCT
       TAAAACCCACCACCTCCCAGTGACTCCAGCTGTCTCTTCCTTATCTAATTCTGAATGTCA
       TTGCCAGTGTGCCCCAAATATGGCTTTCTTCATTCAACTCTTTTTCCTGAAAACTTTCAG

10565  AAAAACAGTGCAGGTTTTCAGATCTGTACAATGCAGTTTGCAATCTTGATTCACGTATGG
       TCAAGTTTCAAATGTTTCTTGAGAAGAATACATATGACCCAGTGCCAGGCAATATGAAGA
       ATGCAATATGTATTTATGTCCAGAAAGAGGTTATGGCAGGGTTGGGAACCTGAAGGAAAA
       AAATGGTCCAGGTAGCTCATGCTTGTCCAATGAGTTATCCCACCTTTCCTCTTAAAACCC
       ACCACCTCCCAGTGACTCCAGCTGTCTCTTCCTTATCTAATTCTGAATGTCATTGCCAGT
       [G,C]
       TGCCCCAAATATGGCTTTCTTCATTCAACTCTTTTTCCTGAAAACTTTCAGTAGTTCCCA
       ACCTCACGTGGTTGGGCACCGTGGCTCGTGCCTGTAATCCCACCAATTTAGGAGGCCAAA
       GCAAGAGGACTGCTTAAGCCCAGGAGTTTGAGGCTGCAGTGAGCCATGATCCCGCCATTG
       CACTCCAGCCTGAGTGAGAGAGCAAGACATTTTTTCTGTCTTTAGAAAAAAAATTGGCTGG
       GCACGGTGGATCACACCTATAATCCTAGCACTTTGAGAGGACACCACTTCCTGTTTCACA

10622  TGGTCAAGTTTCAAATGTTTCTTGAGAAGAATACATATGACCCAGTGCCAGGCAATATGA
       AGAATGCAATATGTATTTATGTCCAGAAAGAGGTTATGGCAGGGTTGGGAACCTGAAGGA
       AAAAAATGGTCCAGGTAGCTCATGCTTGTCCAATGAGTTATCCCACCTTTCCTCTTAAAA
       CCCACCACCTCCCAGTGACTCCAGCTGTCTCTTCCTTATCTAATTCTGAATGTCATTGCC
       AGTGTGCCCCAAATATGGCTTTCTTCATTCAACTCTTTTTCCTGAAAACTTTCAGTAGTT
       [C,T]
       CCAACCTCACGTGGTTGGGCACCGTGGCTCGTGCCTGTAATCCCACCAATTTAGGAGGCC
       AAAGCAAGAGGACTGCTTAAGCCCAGGAGTTTGAGGCTGCAGTGAGCCATGATCCCGCCA
       TTGCACTCCAGCCTGAGTGAGAGAGCAAGACATTTTTTCTGTCTTTAGAAAAAAAATTGGC
       TGGGCACGGTGGATCACACCTATAATCCTAGCACTTTGAGAGGACACCACTTCCTGTTTC
       ACAGACAGTAGGGGCTGTGGAGGAAGAACTCCTTCAGCTCCTGCTCTGTCGCAATTGGCC

10839  ATCTAATTCTGAATGTCATTGCCAGTGTGCCCCAAATATGGCTTTCTTCATTCAACTCTT
       TTTCCTGAAAACTTTCAGTAGTTCCCAACCTCACGTGGTTGGGCACCGTGGCTCGTGCCT
       GTAATCCCACCAATTTAGGAGGCCAAAGCAAGAGGACTGCTTAAGCCCAGGAGTTTGAGG
       CTGCAGTGAGCCATGATCCCGCCATTGCACTCCAGCCTGAGTGAGAGAGCAAGACATTTT
       TTCTGTCTTTAGAAAAAAAATTGGCTGGGCACGGTGGATCACACCTATAATCCTAGCACTT
       [T,C]
       GAGAGGACACCACTTCCTGTTTCACAGACAGTAGGGGCTGTGGAGGAAGAACTCCTTCAG
       CTCCTGCTCTGTCGCAATTGGCCAGCTTGCCTGCGCCTTCTCTGGCGATTGCCTGCTCTC
       CTCCCACCCGTGGAAGTCATGTCCCTTCCCTCTCTAGGGGCAGTCCCTTAGCCAACCTCC
       CTAGTTTCTTAGGAACTCCCCCAGACATGGCCTCTCCCTCTGTCTGCAAACTTTCATTGG
       CATGGTCTTCCATATCCATTGGGTGTTCAGTTTCTTCACCTGCATTTTTAAAAGGCCCAT

11006  CAGGAGTTTGAGGCTGCAGTGAGCCATGATCCCGCCATTGCACTCCAGCCTGAGTGAGAG
       AGCAAGACATTTTTTCTGTCTTTAGAAAAAAAATTGGCTGGGCACGGTGGATCACACCTAT
       AATCCTAGCACTTTGAGAGGACACCACTTCCTGTTTCACAGACAGTAGGGGCTGTGGAGG
       AAGAACTCCTTCAGCTCCTGCTCTGTCGCAATTGGCCAGCTTGCCTGCGCCTTCTCTGGC
       GATTGCCTGCTCTCCTCCCACCCGTGGAAGTCATGTCCCTTCCCTCTCTAGGGGCAGTCC
       [C,T]
       TTAGCCAACCTCCCTAGTTTCTTAGGAACTCCCCCAGACATGGCCTCTCCCTCTGTCTGC
       AAACTTTCATTGGCATGGTCTTCCATATCCATTGGGTGTTCAGTTTCTTCACCTGCATTT
       TTAAAAGGCCCATCCACTGACCCAGTGCTTCACTCCCTCCCTTCCCTCACAGTATCCCCT
       GCCCTCTGCCTTCCTCCAGTGCCTTCATGTTCCCTCCACTATTGCACTGGGGCCCCCTTT
       CCAGCCTCTCCTCTGAAGCTGGTTTTGCTTGGGTCACTGATAGCTTCCCTGTGCTAAATC

12853  TTACCTGGGTGACAGCACCACACCCATCACACTGTGTTGTGTCAACGGCAGTGATCGTTT
       TACTTCTCCCCATCTAGACCCTGAGCTCCTTGTAGGCAAGGCTTGTCTTACTTTACCTTT
       GTGACCTCTGTGTCTGTTACAGTGCCTGGCACTAAGTCGGTAATTTACTGAATGAACGAT
       GGGCCCACTTTGTTGTGTTCACCTGTGCCGAGCTGAGGTTCATTGACTCCCACTGCATCC
       AGGGGATAAACTCTGACTTAGTCTTGGAGTGGCAGATACAAGCGACACACACCCGTCAGC
       [T,C]
       GGAAGGCTCTTGTCCTCTTTGTGAATCAGAACCCTGTTTAGGCTTCTAATCCCACATCAA
       AGCCCATCTCCTCCATGAAATACTCAGTTTTTCTAGCCTGCACTGATCTCTTCCTTCCCT
       GAACTTTCAATGTATTTAATGTACAGCATTGTTCACGCTACCACTGTATTCGTCATTGAT
       TGTTTCATATTTGCAAAATGTTTCTCTCCCCAGTTCAGTTGTAGGCTCCTTGTAATCCGG
       CAGCCCATGCCTTATATGGGCTCTATGCGCTTACGTGGGCCTCTATGAACCCTCAAAATG

13471  GCCAAGCCAGATGGACTGAGCCCTGTTTCTTCTCCTTGGCTGTGGCCTTACTATCTTCCT
       GCCCCTCGTAAACAGCTTTGCCCCTGGGAGTTTGAGGCTGCAGTGAGTTATGATCGTGCC
       ACTGCCCTGAGGCCTGGGTGACAGAGCAAGACCTTGTCTCTAAAAAAATTAAAATAAAAA
       ATTTAAAAAAACAACTTTGCCACCCTACCCATCACACCCCACCCGCCTGACCTGCTTCAC
       AGGCTCCCGACGGCCACTGGCTTCCACCTTCCCCATCTTTCTCTTCCCGCCTCCATCTTT
       [C,T]
       AAGCTGCGAACCAGCCCCTGTTCCTTTCACTGTCCAGCTGTCAATGAGCCCAGAGTCCCT
       TAGCCACCTAGTGCTTTCTTCCCCCTCCTGCTGTCTCTTGGGGTCTTCTGGTGTCTGATT
       CTGTCAGCGGGGCAGGTGGCAGTACCTGTTCTAGCATTCAGGCCACTTGGGGCTGATCCA
       CGCATTGTTTATGTTCTAGCCTGCAGGACAGCCAGGTGGATGGCCCTGCAGCGTGGGAGC
```

FIGURE 3P

```
              CTTGCCCACGGAGTGTTGAATTTCTTAATTGAAATGAATACACTTAAATTAAACCAAAGT
     13500    TTCTCCTTGGCTGTGGCCTTACTATCTTCCTGCCCCTCGTAAACAGCTTTGCCCCTGGGA
              GTTTGAGGCTGCAGTGAGTTATGATCGTGCCACTGCCCTGAGGCCTGGGTGACAGAGCAA
              GACCTTGTCTCTAAAAAAATTAAAATAAAAAATTTAAAAAAACAACTTTGCCACCCTACC
              CATCACACCCCACCCGCCTGACCTGCTTCACAGGCTCCCGACGGCCACTGGCTTCCACCT
              TCCCCATCTTTCTCTTCCCGCCTCCATCTTTTAAGCTGCGAACCAGCCCCTGTTCCTTTC
              [A,G]
              CTGTCCAGCTGTCAATGAGCCCAGAGTCCCTTAGCCACCTAGTGCTTTCTTCCCCCTCCT
              GCTGTCTCTTGGGGTCTTCTGGTGTCTGATTCTGTCAGCGGGGCAGGTGGCAGTACCTGT
              TCTAGCATTCAGGCCACTTGGGGCTGATCCACGCATTGTTTATGTTCTAGCCTGCAGGAC
              AGCCAGGTGGATGGCCCTGCAGCGTGGGAGCCTTGCCCACGGAGTGTTGAATTTCTTAAT
              TGAAATGAATACACTTAAATTAAACCAAAGTTTTGTAGAAGAAATCCTGGCCAGGCACGG
     13507    TGGCTGTGGCCTTACTATCTTCCTGCCCCTCGTAAACAGCTTTGCCCCTGGGAGTTTGAG
              GCTGCAGTGAGTTATGATCGTGCCACTGCCCTGAGGCCTGGGTGACAGAGCAAGACCTTG
              TCTCTAAAAAAATTAAAATAAAAAATTTAAAAAAACAACTTTGCCACCCTACCCATCACA
              CCCCACCCGCCTGACCTGCTTCACAGGCTCCCGACGGCCACTGGCTTCCACCTTCCCCAT
              CTTTCTCTTCCCGCCTCCATCTTTTAAGCTGCGAACCAGCCCCTGTTCCTTTCACTGTCC
              [A,G]
              GCTGTCAATGAGCCCAGAGTCCCTTAGCCACCTAGTGCTTTCTTCCCCCTCCTGCTGTCT
              CTTGGGGTCTTCTGGTGTCTGATTCTGTCAGCGGGGCAGGTGGCAGTACCTGTTCTAGCA
              TTCAGGCCACTTGGGGCTGATCCACGCATTGTTTATGTTCTAGCCTGCAGGACAGCCAGG
              TGGATGGCCCTGCAGCGTGGGAGCCTTGCCCACGGAGTGTTGAATTTCTTAATTGAAATG
              AATACACTTAAATTAAACCAAAGTTTTGTAGAAGAAATCCTGGCCAGGCACGGTGGCTCA
     13554    CTGGGAGTTTGAGGCTGCAGTGAGTTATGATCGTGCCACTGCCCTGAGGCCTGGGTGACA
              GAGCAAGACCTTGTCTCTAAAAAAATTAAAATAAAAAATTTAAAAAAACAACTTTGCCAC
              CCTACCCATCACACCCCACCCGCCTGACCTGCTTCACAGGCTCCCGACGGCCACTGGCTT
              CCACCTTCCCCATCTTTCTCTTCCCGCCTCCATCTTTTAAGCTGCGAACCAGCCCCTGTT
              CCTTTCACTGTCCAGCTGTCAATGAGCCCAGAGTCCCTTAGCCACCTAGTGCTTTCTTCC
              [C,A]
              CCTCCTGCTGTCTCTTGGGGTCTTCTGGTGTCTGATTCTGTCAGCGGGGCAGGTGGCAGT
              ACCTGTTCTAGCATTCAGGCCACTTGGGGCTGATCCACGCATTGTTTATGTTCTAGCCTG
              CAGGACAGCCAGGTGGATGGCCCTGCAGCGTGGGAGCCTTGCCCACGGAGTGTTGAATTT
              CTTAATTGAAATGAATACACTTAAATTAAACCAAAGTTTTGTAGAAGAAATCCTGGCCAG
              GCACGGTGGCTCACGCCTGTAATCCCAACACTTTGGGAGGCCGAGGCGGGTGGATCACCT
     13737    CCTTCCCCATCTTTCTCTTCCCGCCTCCATCTTTTAAGCTGCGAACCAGCCCCTGTTCCT
              TTCACTGTCCAGCTGTCAATGAGCCCAGAGTCCCTTAGCCACCTAGTGCTTTCTTCCCCC
              TCCTGCTGTCTCTTGGGGTCTTCTGGTGTCTGATTCTGTCAGCGGGGCAGGTGGCAGTAC
              CTGTTCTAGCATTCAGGCCACTTGGGGCTGATCCACGCATTGTTTATGTTCTAGCCTGCA
              GGACAGCCAGGTGGATGGCCCTGCAGCGTGGGAGCCTTGCCCACGGAGTGTTGAATTTCT
              [T,C]
              AATTGAAATGAATACACTTAAATTAAACCAAAGTTTTGTAGAAGAAATCCTGGCCAGGCA
              CGGTGGCTCACGCCTGTAATCCCAACACTTTGGGAGGCCGAGGCGGGTGGATCACCTGAT
              GTCAGGAGTTTAAGACCAGCCTGGCCAACGTGGTGAAATCCCGTCTCTACTAAAAATACA
              AAAAATTAGCCAGGCATTGTGGTGGGTGCTTGTAATCCCAGCTGCTTGCGGGGCTGAGGC
              AGGAGAATCGCATGAACCCGGGAGGCGGAGGTTACAATGAGCTGAGATCGTTCCATTGCA
     13940    GGGGCTGATCCACGCATTGTTTATGTTCTAGCCTGCAGGACAGCCAGGTGGATGGCCCTG
              CAGCGTGGGAGCCTTGCCCACGGAGTGTTGAATTTCTTAATTGAAATGAATACACTTAAA
              TTAAACCAAAGTTTTGTAGAAGAAATCCTGGCCAGGCACGGTGGCTCACGCCTGTAATCC
              CAACACTTTGGGAGGCCGAGGCGGGTGGATCACCTGATGTCAGGAGTTTAAGACCAGCCT
              GGCCAACGTGGTGAAATCCCGTCTCTACTAAAAATACAAAAAATTAGCCAGGCATTGTGG
              [T,C]
              GGGTGCTTGTAATCCCAGCTGCTTGCGGGGCTGAGGCAGGAGAATCGCATGAACCCGGGA
              GGCGGAGGTTACAATGAGCTGAGATCGTTCCATTGCACTCCAGTCTGGGCAACAAGAGCG
              AAACTCCGTCTCAAAAAAAAAAAGAAATCCTGTTGGCTTTCTGTGCAGTTTTTTGATGCC
              ATTGTGACACAGAGAAACTTTATTTCAGGAACTGCTTATATCAACATCAGAACTTAAGGA
              AATGTCTGAGTACTACTTTGATGGGAAAGGGAAAGCCTTTCGACCAATTATTGTGGCGCT
     15427    CTGAGACTTGCCCCCAGATCCCCCGTCAGTGCACGACTCTGCCCCAGCTGCTGTATCAGG
              TATGGTTGGTACCTGTTGGCCTTCATTTCTTAGCCTCTTCAAGGATTGCCTTGGCTACAA
              AGAGTCCTCTCACCTTAGGCTGTGCCCCTTCGGGAGGCAGCCCACATCCAGGGACTGATA
              GATGAAGGGCCATTCTACCTGCACACCCTAGAGGGTGTTTCAGGCTGTTGATTCCAGCTC
              AGCTTCTCCTGCTACCCAGTCCTGTATCCTCTCCCCCTCCCTCAGGTGTCAGTAATCCCA
              [A,G]
              GGGATAATCCCGAATAAACATCCTGTCCTTTAAACTTCATCTCAGAGTCTGCCTCCTGCA
              GAACCTAACTTGCAACAGAGCTCAGCAAAACCCAAGCTCATTTTATTAAAGAACCCAGAT
              CAAAAAAGAGCTTTATGGGCTGGGCACAGTGGCTCACGCCTGTAATCCCAGCACTTTGGG
              AGGCCAAGGTGGGTGGATCACATGAGTTCAGGAGTTTGAGGCTAGCCTGGCCAACATGGT
              GAAACCCCATCTCTACAAAAAATATAAAAATTAGCCAGTCGTGGTGACACACACCTATAA
     15486    GTATGGTTGGTACCTGTTGGCCTTCATTTCTTAGCCTCTTCAAGGATTGCCTTGGCTACA
              AAGAGTCCTCTCACCTTAGGCTGTGCCCCTTCGGGAGGCAGCCCACATCCAGGGACTGAT
              AGATGAAGGGCCATTCTACCTGCACACCCTAGAGGGTGTTTCAGGCTGTTGATTCCAGCT
```

FIGURE 3Q

```
        CAGCTTCTCCTGCTACCCAGTCCTGTATCCTCTCCCCCTCCCTCAGGTGTCAGTAATCCC
        AAGGGATAATCCCGAATAAACATCCTGTCCTTTAAACTTCATCTCAGAGTCTGCCTCCTG
        [C,G]
        AGAACCTAACTTGCAACAGAGCTCAGCAAAACCCAAGCTCATTTTATTAAAGAACCCAGA
        TCAAAAAAGAGCTTTATGGGCTGGGCACAGTGGCTCACGCCTGTAATCCCAGCACTTTGG
        GAGGCCAAGGTGGGTGGATCACATGAGTTCAGGAGTTTGAGGCTAGCCTGGCCAACATGG
        TGAAACCCCATCTCTACAAAAAATATAAAAATTAGCCAGTCGTGGTGACACACACCTATA
        AATCCCAGCTACTCAGGAGGCTGGGGCAGGAGAATCGCTTGAACCCAGGAGGTGGAGGCT

15648   AGGCTGTTGATTCCAGCTCAGCTTCTCCTGCTACCCAGTCCTGTATCCTCTCCCCCTCCC
        TCAGGTGTCAGTAATCCCAAGGGATAATCCCGAATAAACATCCTGTCCTTTAAACTTCAT
        CTCAGAGTCTGCCTCCTGCAGAACCTAACTTGCAACAGAGCTCAGCAAAACCCAAGCTCA
        TTTTATTAAAGAACCCAGATCAAAAAAGAGCTTTATGGGCTGGGCACAGTGGCTCACGCC
        TGTAATCCCAGCACTTTGGGAGGCCAAGGTGGGTGGATCACATGAGTTCAGGAGTTTGAG
        [G,A]
        CTAGCCTGGCCAACATGGTGAAACCCCATCTCTACAAAAAATATAAAAATTAGCCAGTCG
        TGGTGACACACACCTATAAATCCCAGCTACTCAGGAGGCTGGGGCAGGAGAATCGCTTGA
        ACCCAGGAGGTGGAGGCTGCAGTGAGCAGAGATTGCGCCACTGCACTCCAGCCTAGGGGA
        GACTCTGTCTCAAAAAAAAAAAAAAAGAAAAGAAAAAGAGCTTTATGATAGATTTCTATA
        AAATTGCTTCACTCACTGAATGCAGCACAGTTATAGTGTCTGCATGTTTCTCAGACAAGC

15650   GCTGTTGATTCCAGCTCAGCTTCTCCTGCTACCCAGTCCTGTATCCTCTCCCCCTCCCTC
        AGGTGTCAGTAATCCCAAGGGATAATCCCGAATAAACATCCTGTCCTTTAAACTTCATCT
        CAGAGTCTGCCTCCTGCAGAACCTAACTTGCAACAGAGCTCAGCAAAACCCAAGCTCATT
        TTATTAAAGAACCCAGATCAAAAAAGAGCTTTATGGGCTGGGCACAGTGGCTCACGCCTG
        TAATCCCAGCACTTTGGGAGGCCAAGGTGGGTGGATCACATGAGTTCAGGAGTTTGAGGC
        [T,C]
        AGCCTGGCCAACATGGTGAAACCCCATCTCTACAAAAAATATAAAAATTAGCCAGTCGTG
        GTGACACACACCTATAAATCCCAGCTACTCAGGAGGCTGGGGCAGGAGAATCGCTTGAAC
        CCAGGAGGTGGAGGCTGCAGTGAGCAGAGATTGCGCCACTGCACTCCAGCCTAGGGGAGA
        CTCTGTCTCAAAAAAAAAAAAAAAGAAAAGAAAAAGAGCTTTATGATAGATTTCTATAAA
        ATTGCTTCACTCACTGAATGCAGCACAGTTATAGTGTCTGCATGTTTCTCAGACAAGCCA

15840   ACCCAGATCAAAAAAGAGCTTTATGGGCTGGGCACAGTGGCTCACGCCTGTAATCCCAGC
        ACTTTGGGAGGCCAAGGTGGGTGGATCACATGAGTTCAGGAGTTTGAGGCTAGCCTGGCC
        AACATGGTGAAACCCCATCTCTACAAAAAATATAAAAATTAGCCAGTCGTGGTGACACAC
        ACCTATAAATCCCAGCTACTCAGGAGGCTGGGGCAGGAGAATCGCTTGAACCCAGGAGGT
        GGAGGCTGCAGTGAGCAGAGATTGCGCCACTGCACTCCAGCCTAGGGGAGACTCTGTCTC
        [-,A]
        AAAAAAAAAAAAAAGAAAAGAAAAAGAGCTTTATGATAGATTTCTATAAAATTGCTTCAC
        TCACTGAATGCAGCACAGTTATAGTGTCTGCATGTTTCTCAGACAAGCCAAACCTACCTA
        GCCTGCTCAGCTGCCTCATTGAAGACACTGTTATCACTGGCACCTGGATCTTGGCACCAT
        CCATTCCTGTGTGAAACTCTTTTAGTTCTAAGAAGTGAATATCATTGCCAGCAATCAGGA
        TAACAGACTACCCAAATTGTGCTGTACAGAGATCTGTTGATATCAATTTTTGCAAATAGCC

17726   AGTTAAAAAAATTCCCACTGAAGAGAGACAGACTTTATTCTGAGCCTTACGTGTTTCTTT
        AGGTTTAGAAGGTGAATGAGCAGTGGCTGGGGAGGATGGCCTAGAAGTTGGAGCTCACAG
        GCTTCCTCCCTGCACTCTGCCATTCCTTAGATTGGAGGCGCCCTTGATACAGATCCCTCC
        CTACACACTGGGGGTTTACTTGCAATTTAAGACTTCACATTTTATATTAGTATGAACAGG
        GAAAATATATTTTGTAAAACCACATGTAAACCTCGTAAAGGATTCACTGGTAGGGTCATT
        [A,G]
        TATTATTCTGTCTATTTTTAGGTATGTTTGAAACTCTTCATTATTAAAAAAATTTTTTTG
        GCCGGGTGCGGTGGCTCACGTAATCTCAGCACTCTGGGAGGCCAAGGCAGGTGGATCATG
        TGAGGTCATGAGTTTGAGACCAGCCTTGCCAACATGGCAAAACCCCATCTCTACTAAAAA
        TACAAAAATTATCTGGGCGTGGTGGCACATGCCTGTAGTCTCAGCTACCTGGGAGGCTCA
        GGCAGAAGAATCACTAAAACAAGGAGGCGAAGGTTGCAGTGAGTCAAGATTGCGCCCCTG

17736   ATTCCCACTGAAGAGAGACAGACTTTATTCTGAGCCTTACGTGTTTCTTTAGGTTTAGAA
        GGTGAATGAGCAGTGGCTGGGGAGGATGGCCTAGAAGTTGGAGCTCACAGGCTTCCTCCC
        TGCACTCTGCCATTCCTTAGATTGGAGGCGCCCTTGATACAGATCCCTCCCTACACACTG
        GGGGTTTACTTGCAATTTAAGACTTCACATTTTATATTAGTATGAACAGGGAAAATATAT
        TTTGTAAAACCACATGTAAACCTCGTAAAGGATTCACTGGTAGGGTCATTATATTATTCT
        [G,A]
        TCTATTTTTAGGTATGTTTGAAACTCTTCATTATTAAAAAAATTTTTTTGGCCGGGTGCG
        GTGGCTCACGTAATCTCAGCACTCTGGGAGGCCAAGGCAGGTGGATCATGTGAGGTCATG
        AGTTTGAGACCAGCCTTGCCAACATGGCAAAACCCCATCTCTACTAAAAATACAAAAATT
        ATCTGGGCGTGGTGGCACATGCCTGTAGTCTCAGCTACCTGGGAGGCTCAGGCAGAAGAA
        TCACTAAAACAAGGAGGCGAAGGTTGCAGTGAGTCAAGATTGCGCCCCTGCACTCTAGCC

18850   ATCCTGATTTCATCAGTCAACAATTTAGCCATGCAAAATGACATTTTTTATTCTATTTAT
        TTATTTATTCGGAGACAGAGTCTCGCTCTACCCCCCAGGCTGGAGTACAGTGGTGCAAGT
        CTCAGCTCACTGCAACCTCCACCTCCCAGGTTCAAGCGATTCTCCTGCCTCAGCCTCCCA
        AGTAGCTGGGATTACAGGCACCCACTACCATGCCTGGCTAGTTTTTTGTATTTTTAGTGGA
        GACGTGGTTTCGTCATGTTGGCCAGGCTGGTCTCGAACTCCTGACCTCAGGTGATCCTCC
        [T,C]
        GCCTCGGCGTCCCAAAGCGCTGGGATTATGGGCATGAGCCACTGCGCCAGGCGCAAAATG
        ACATTTTTAGATGGATATATAGTCTATGAAATTTCAAAATATTTTAAGAAATCTTTGTTG
```

FIGURE 3R

```
         TAATAATAGCTTCAGATTACCAAAACAACTCTAGTATCTTGGTGAGTGCTGCCAATTTCA
         TTGCAACTTCTCAGCAGGAGCCCCGTCTGCTGATGTAATTTATCATAATGGAAGTGGTGC
         CCAACTTCTGAATGCATGAGAAAGGCTAGACCTTACCTGTTGTTTTAAGGTAAGGTCTAC
19419    GACCTTACCTGTTGTTTTAAGGTAAGGTCTACTGCTAACTAGTAGGAGGTGTCTAATTTA
         TTAGACTGAAATTCACTTGCAAAAATATTCTAAAAGCCTTATATTAAAAAAAAACTGTAA
         AAGTTTATATCTTTTCCTGTGCATTCAACTCAAAGAAGATAGGGCCTAGTAAATTTACCT
         GAAAAATATTTAAGTATTCTAATATAAAAACTGAATCTCACTGAGGGATTCAGGTGGCTT
         AAAACTCACCTGAACCCTGAACCTCTATTTTCTCATTTACTGAAGTTTATTGGGGTTTTT
         [-,G]
         TTTTTTTGTGTGTTTTTTTGAAATGAAGTCTCTGTCACCCAGGCTGGAGTGCAGTGGCAT
         AATCTCGGCTCACTGCAACCTCCACTTCCCGGCTCAAGTGATTCTCCTGCATCAGCCTCT
         CAAGTAGCTGGGATTACAGATGCACACCACCATGCCCGACTAATCTTTGTATTTTAAGTA
         GAGTTGGAGTTTCACCCTGTTGTCCAGGCTGGTCTCGAACTCCTGACCTCAAGTGATCCG
         CCCGCCTCAGCCTTCCAGAGTGCTGGGATTACAGGCAGGAACCTGTAACTGTGCCTAGAC
19429    GTTGTTTTAAGGTAAGGTCTACTGCTAACTAGTAGGAGGTGTCTAATTTATTAGACTGAA
         ATTCACTTGCAAAAATATTCTAAAAGCCTTATATTAAAAAAAAACTGTAAAAGTTTATAT
         CTTTTCCTGTGCATTCAACTCAAAGAAGATAGGGCCTAGTAAATTTACCTGAAAAATATT
         TAAGTATTCTAATATAAAAACTGAATCTCACTGAGGGATTCAGGTGGCTTAAAACTCACC
         TGAACCCTGAACCTCTATTTTCTCATTTACTGAAGTTTATTGGGGTTTTTGTTTTTTTGT
         [G,-]
         TGTTTTTTTGAAATGAAGTCTCTGTCACCCAGGCTGGAGTGCAGTGGCATAATCTCGGCT
         CACTGCAACCTCCACTTCCCGGCTCAAGTGATTCTCCTGCATCAGCCTCTCAAGTAGCTG
         GGATTACAGATGCACACCACCATGCCCGACTAATCTTTGTATTTTAAGTAGAGTTGGAGT
         TTCACCCTGTTGTCCAGGCTGGTCTCGAACTCCTGACCTCAAGTGATCCGCCCGCCTCAG
         CCTTCCAGAGTGCTGGGATTACAGGCAGGAACCTGTAACTGTGCCTAGACTACAGAAGTG
19431    TGTTTTAAGGTAAGGTCTACTGCTAACTAGTAGGAGGTGTCTAATTTATTAGACTGAAAT
         TCACTTGCAAAAATATTCTAAAAGCCTTATATTAAAAAAAAACTGTAAAAGTTTATATCT
         TTTCCTGTGCATTCAACTCAAAGAAGATAGGGCCTAGTAAATTTACCTGAAAAATATTTA
         AGTATTCTAATATAAAAACTGAATCTCACTGAGGGATTCAGGTGGCTTAAAACTCACCTG
         AACCCTGAACCTCTATTTTCTCATTTACTGAAGTTTATTGGGGTTTTTGTTTTTTTGTGT
         [G,-]
         TTTTTTTGAAATGAAGTCTCTGTCACCCAGGCTGGAGTGCAGTGGCATAATCTCGGCTCA
         CTGCAACCTCCACTTCCCGGCTCAAGTGATTCTCCTGCATCAGCCTCTCAAGTAGCTGGG
         ATTACAGATGCACACCACCATGCCCGACTAATCTTTGTATTTTAAGTAGAGTTGGAGTTT
         CACCCTGTTGTCCAGGCTGGTCTCGAACTCCTGACCTCAAGTGATCCGCCCGCCTCAGCC
         TTCCAGAGTGCTGGGATTACAGGCAGGAACCTGTAACTGTGCCTAGACTACAGAAGTGGT
22516    ATGTATATATTAAAGCATATTTCTATATTATTAGCATTGGGAATATGGGAAACAGGGACT
         TGGTTTGAGGATGCATAGATCCTGGGTTGAAGGATGAGAATAAAGTTGAACAGATGAGAA
         TGAAAATGCACAGGCATCCATCGCCATCACCACACACGTGCTCTACAAACAAAAAGTTTG
         TGCAGGCCAGGCGCAGTGGCTCATGCCTGTAATCCCAGCACTTTGGGAGGCTGAGGTGGG
         TGGATCACCTGAGGTCAGGAGTTCGAGACCAGCCTGGCCAACAAGGCAAAACCCTGTCAC
         [T,C]
         ACTAAAAAAAACACAAAAATTAGCCAGTGTACACCTGTAATCTCAGCTACTCAGGAGGCTT
         AGGCAGGAGAATCGCTTGAACCTGGGAGAGGGAGGTTGCAGTGAGCCAATATCACACTAC
         TGCACTCCAGCCTGGGCAACAGAGTGAGACTCCATTTCAAAAAAAAAAAAAAAGTTTGTG
         CAAACAACTACCCCACCCTCACCTCCTTTTCTCTCATAGATTTATAGTATTCCTGGTTCA
         TTCCTATTTAATTCTCCTTATTAAAAGAAGAGATATATGTATATACACACACACACACAC
22543    TTATTAGCATTGGGAATATGGGAAACAGGGACTTGGTTTGAGGATGCATAGATCCTGGGT
         TGAAGGATGAGAATAAAGTTGAACAGATGAGAATGAAAATGCACAGGCATCCATCGCCAT
         CACCACACACGTGCTCTACAAACAAAAAGTTTGTGCAGGCCAGGCGCAGTGGCTCATGCC
         TGTAATCCCAGCACTTTGGGAGGCTGAGGTGGGTGGATCACCTGAGGTCAGGAGTTCGAG
         ACCAGCCTGGCCAACAAGGCAAAACCCTGTCACTACTAAAAAAAACACAAAAATTAGCCAG
         [T,C]
         GTACACCTGTAATCTCAGCTACTCAGGAGGCTTAGGCAGGAGAATCGCTTGAACCTGGGA
         GAGGGAGGTTGCAGTGAGCCAATATCACACTACTGCACTCCAGCCTGGGCAACAGAGTGA
         GACTCCATTTCAAAAAAAAAAAAAAGTTTGTGCAAACAACTACCCCACCCTCACCTCCT
         TTTCTCTCATAGATTTATAGTATTCCTGGTTCATTCCTATTTAATTCTCCTTATTAAAAG
         AAGAGATATATGTATATACACACACACACACACACACACACACACATACATATA
23568    ATCTGCTTAGCACAGGGCTACTTGCCAGTTCCTACCTGTTTCTGCCTCTGACCCACAACT
         GCTATGTTACCGGTACAAAACCCCCCACACACGTGCCCCCTCGGTGAGCCCTTGTTAGG
         CCTGGCCTGGGCTTCCTAGCACTTCTTTCCTTTAACTCCCACCCCTGGCCGTCACAGTCC
         TGTGGCTTCCATGTCATATGCTGGACCTTTGGTCTCTAGGATCTCCCCGGCCAGGTGAAG
         AAGGAACTAAAGGCCAAAGGATCCCGAGCCTTGAGCTGCTAATGATGTAGGGGCTGGGTC
         [A,G]
         GGGAATGTAAGTGGGTACCTATATATCATAATTTGTAAAATGACTTTATAGGCATATACT
         TACATCAGGATGTCTTACATAATATGTATATTATATAAAGTGGTGATTAATTGGTAAACA
         CAATGAACATCACTGTTTAGATACTGAAGAACCTAAGACAATAAGTACCTAAATAGTTAT
         GTTGAAAATTCTGTGAACCTAGCCTTTATAACTAATTACTACAGAATGTAACACTTACG
         GCCGGGTGTGGTGGCTCACGCCTGTAATCCCAGCACTTTGGGAGGCCGAGGCAGTTGGAT
23779    GTCTCTAGGATCTCCCCGGCCAGGTGAAGAAGGAACTAAAGGCCAAAGGATCCCGAGCCT
```

FIGURE 3S

```
       TGAGCTGCTAATGATGTAGGGGCTGGGTCAGGGAATGTAAGTGGGTACCTATATATCATA
       ATTTGTAAAATGACTTTATAGGCATATACTTACATCAGGATGTCTTACATAATATGTATA
       TTATATAAAGTGGTGATTAATTGGTAAACACAATGAACATCACTGTTTAGATACTGAAGA
       ACCTAAGACAATAAGTACCTAAATAGTTATGTTGAAAATTCTGTGAACTCTAGCCTTTAT
       [A,G]
       ACTAATTACTACAGAATGTAACACTTACGGCCGGGTGTGGTGGCTCACGCCTGTAATCCT
       AGCACTTTGGGAGGCCGAGGCAGTTGGATCACTTGGGGCCAGGAGTTCGAGACCAGCCTG
       GCCAACATGGTGAAACCCCATCTCTAGTAAAAATACAAAAATACCTGGGCGTGGTGGTGT
       ACGCTTGTAGTCCCAGCTACTCATGAGGCTGAGGTGGGGGGATTGCTTGAACCCAGGAGG
       AAGAGTCTGCAGTGAGCCGAGGTCATGCCACTGTACTCAAGCCTGGGCAACAGAGCAAGA

23808  AAGGAACTAAAGGCCAAAGGATCCCGAGCCTTGAGCTGCTAATGATGTAGGGGCTGGGTC
       AGGGAATGTAAGTGGGTACCTATATATCATAATTTGTAAAATGACTTTATAGGCATATAC
       TTACATCAGGATGTCTTACATAATATGTATATTATATAAAGTGGTGATTAATTGGTAAAC
       ACAATGAACATCACTGTTTAGATACTGAAGAACCTAAGACAATAAGTACCTAAATAGTTA
       TGTTGAAAATTCTGTGAACTCTAGCCTTTATAACTAATTACTACAGAATGTAACACTTAC
       [A,G]
       GCCGGGTGTGGTGGCTCACGCCTGTAATCCTAGCACTTTGGGAGGCCGAGGCAGTTGGAT
       CACTTGGGGCCAGGAGTTCGAGACCAGCCTGGCCAACATGGTGAAACCCCATCTCTAGTA
       AAAATACAAAAATACCTGGGCGTGGTGGTGTACGCTTGTAGTCCCAGCTACTCATGAGGC
       TGAGGTGGGGGGATTGCTTGAACCCAGGAGGAAGAGTCTGCAGTGAGCCGAGGTCATGCC
       ACTGTACTCAAGCCTGGGCAACAGAGCAAGACTCTTTCTCAAAAAAAAAAAAAAGAATGT

23979  TTGGTAAACACAATGAACATCACTGTTTAGATACTGAAGAACCTAAGACAATAAGTACCT
       AAATAGTTATGTTGAAAATTCTGTGAACTCTAGCCTTTATAACTAATTACTACAGAATGT
       AACACTTACGGCCGGGTGTGGTGGCTCACGCCTGTAATCCTAGCACTTTGGGAGGCCGAG
       GCAGTTGGATCACTTGGGGCCAGGAGTTCGAGACCAGCCTGGCCAACATGGTGAAACCCC
       ATCTCTAGTAAAAATACAAAAATACCTGGGCGTGGTGGTGTACGCTTGTAGTCCCAGCTA
       [C,T]
       TCATGAGGCTGAGGTGGGGGGATTGCTTGAACCCAGGAGGAAGAGTCTGCAGTGAGCCGA
       GGTCATGCCACTGTACTCAAGCCTGGGCAACAGAGCAAGACTCTTTCTCAAAAAAAAAAA
       AAAGAATGTAATATATATCTTTAAATATGCAAATTAATGTGATATATAGGGTGTATTTGG
       TTATAGCATATAATTCAACTATTTATGCAGTAGTTTATAACTAGTTGCTAATACAGTGTA
       GACATCCATCACAGTCTAAAGAAGACTGGAAATATGTTGATTGCTTAGTGTTCAATGGAA

24319  GAAGAGTCTGCAGTGAGCCGAGGTCATGCCACTGTACTCAAGCCTGGGCAACAGAGCAAG
       ACTCTTTCTCAAAAAAAAAAAAAAGAATGTAATATATATCTTTAAATATGCAAATTAATG
       TGATATATAGGGTGTATTTGGTTATAGCATATAATTCAACTATTTATGCAGTAGTTTATA
       ACTAGTTGCTAATACAGTGTAGACATCCATCACAGTCTAAAGAAGACTGGAAATATGTTG
       ATTGCTTAGTGTTCAATGGAAAAACTTTTTTTTTTTTTTGTCTAGGAATGAGGGGCAGTG
       [C,T]
       CACATAGTACAAAAAGCATTTCACTTGGAGCCAAAATTCTTTGGTTTAATTTTTATTGAA
       AATAACATGTATCGTGCCATGCTCTGGGGTGTGCTCAGTACTAGCTGAGATGATTCCTAG
       TCTGAGCTCCCACTCCACTCCACCCTCCCCACTGCCCTGGGAGCATAGAGACTAGAGCAT
       CACTGACTGGTACGCAAGGTGTGATGGTCGCAGCATGCATGGGTGTTGTACACGCACAAA
       AGGGAGGCATCTGACCAGACTGAGGGATCGGGGGGAACTTCTTAGAGGTGGCATCTGAAC

27647  GAGACTATTGGAATTGGAAACACCAAGACTTACTGTCTGCACCATGCAGACATCCTGCAG
       GCACGGGGTGGGGCGGCACCAAATTGGAGCTAGCACAGAAATTCACTCAGTGATGGAAGC
       TTACAAAGGGTCCAAAGAAATGGACCTGAGTCATGATAGAGAGGTTTCCTTGTGGTCACT
       GTTTTCTGTTTAAGAAGCCAAAGATAATGCACAGGAATTCTTTTATAAAGATATGCACCT
       CATTCTTCAAAGATTAGCAGCTGAACGAACAGTGAACATGTTAACGTGGCTGGACCCTTA
       [A,T]
       TAAAAATGAAATGTTTCATGCTGCCCACTAGGGGGCATGCTGGCATCGTCCCAGCACTAC
       CTCCTTTTCATGTGGTTTATTCCTAAACTCCACAGCTCTTAGAATAATAAAGCAAAATGA
       TAGTGTGAGCTATTTGAATAAAAGTTTCTATATTTAAGTGCCTATGGGTGGAAATATTCC
       AGAGGTGTTTATGGATTCAAAATGGCTATTTTTACGTACTCTTGGTATTTAAAATGCAAAG
       CCATGCGAGCTCCAAATAAATGCATGCAAAGCAAATTAGACACACCAAAAAGAGGGGAGG

29477  GCATTTTGCTGTCATGACTCTGTAGTCTCTTGTCATCTAGAACAGTCTTTCTTTGCCTCT
       CATTACCTTGGTATTTGGAAGAGTGCAGGCCAGTTATGTTGTTGAGCCTCTCAGTCGGGC
       TTCTCTGATACTTCTCAAGATTCGATCCAGGTTATGAATATTTGGCAGGAATACCACAAG
       AGCGGTGCTGTCCTCAGCTCCTCATACCAGGAGGCGCGTGCTGTCTTGTCTGTCCCGTTA
       CTGGTGATGCATGCCTGGATCGCTTGATTAGGATACTGTCGGGCCGGGCACAGTGGCTCA
       [C,T]
       GCCTGTAATCCCAGCACTTTGGAAGGCCGAGGTGGGCAGATTACCTGAGGTCAAGAGTTC
       AAGACCAGCCTGGCCAACATGGTAAAACCCCATCTCTACTAAAATTATAAAAAATTAGCT
       GGGCATGGTGGCGGGCACCTGTAATCTCAGCACTTTGGGAGGCCGAGGCGGGTAGATCAC
       CTGAGGTCAAGAGTTTGACAAGCGTGGCCAACATAGTGAAACCATGTCTCTACTAAAAAT
       ACAAAAATTAGCCGGGCGTAGTGGCAGGCGCCTATAATCCCAGCTACTCTGGAGGCTGAT

34277  ATGTAATGCCTGGTACCGTCTGTGTCTCAGTTTCTCGAACTTCATAAGTGACTTAAGATG
       TGAGAACTCTCAGAACAGTGCCTAGCACATAGTGGACGCTCAGAAATTGTTAGCTTTTAT
       CATCACCAACCACATAATCCATATTTGTGGGATATTGTGAGGTTTAACTCAAATCATACA
       AAGTGTTCATCATATGTGCTCCACACATTTTAATCCATTAAAATGTTCACTAACAGATTT
       TTAGGCCGGGCACGGTGGCTCACGCCTGTAATCCCAGCACTTTGGGAGGCTGAGGCAGGC
       [A,G]
```

FIGURE 3T

```
         GATCACCTGAGGTCAGGAGTTCGAGACCAGCCTGAAACCCCGTCTCTACTAAAAATACAA
         AAATTAGCTGGGCGTGGTGGCATACGGAGGTTGAGGCAGGAGAATCGCTTGAACTTGGGA
         GGTGGAGATTACAGTGAGCCCAGATCGTGCCGCTGCACTCTAGCCTGGGTGACAGAGAGA
         CTCCGTCTCCAAAAAAAGAAATAGATTTTTAGAAAATCTTTCACTTTTCAGGAAGAAAGC
         TTATAGTCTCTGTGGCTCTGTGTTGAGGAAACAGCATTAATCTCACTACAGGAGACTGCT
35207    AGCACTACATAGTCAACAGACCTCATTAAGTTGTCAAAAAGCATTCTCAGGCTGAGGACG
         TTAGGCAACCTGGCTTTAGTTGGCAGAGGTGCGTGGACACTGCCAAGGCTCCTATTTCTG
         GTTCCAGTGGATGAGGTGGAGGAGGATTATTTGTAATAATAGCAAACAGCCAGGTGCGGT
         GGCTCACACCTGATAATCTCAACGCTTTGGGAGGTGGAGGTGGGAGGATCACGAGCCCAG
         GAGTTTGAGGCCAGCCTAGACAACATGGTGAGACTCCATCTCTATGAAAAAATTAAAAAT
         [C,T]
         AGCTGGGTGTGGTTGCGCGTGCCTGTAGTCCCAGCTACTCAGGAGACTGAGGCGGAAGGA
         ACCCTTGAGCCCAGGAGTTCAAGGTTACAGTGAGCTATGATCGCACCACTGTACCCCAGC
         CTGGGCAACAGAGTGAGACCCTATTTCTAAAAAGAGATAATAATAGCAAACACACATTGA
         GTTCTAACCAGGTGCCAGGCAGTATACTGAGGGCTTAAATGCAGCATCATGTCTGTTTCT
         CACAGCAACCCTACAAGGTAAGTGCTTGTGATTTCTACATTGTACAGATGAGCAAGAGAG
37162    TTGGACTTCACCTCGTGTTCTGACCAGATGGGCAAACCAACATCAGCTGATCTGAAGCTC
         GGGTTAGCCACTGGTCCTGTCCTGTTTGCCTGTCAGCAGGTAGGTTTTACAAACTCCCTT
         TGACACATCACTGCATAGCCCCACAGAACTGATGTCCCGCGGCACAGCTGATGGGAAGAT
         TGCATAAAGGAATAGATGGGAAGGCATTCAGATAAGAGATCACAGGTCTGCATTTGATCC
         TGGCTGAGTGAGATGTTGGGGCTGGTCATTTCACCTTGCTAAGACTGTTTCCTTATCTGT
         [G,A]
         AAATTGAGAAGATCACCTTTCTCCCAGGGTGGTTGTGAGGATTAGCTAAGATCCTATTTG
         AGATCTTTGTGTCTTGTGGTGTGCCATAGGCATTTGAGGTAGCATCGTGATTATTTCCAT
         ATATTTTGGCCACTGGCAAAGTGAACGGTTTCTAAGTCTTGATTATAGGACTGGACTTTG
         GTGGTCCTCAGAGCCCCTTAAAAGGCATAGGAAGCATCAAGGGCCTCCAAGCATAAGAAA
         TTCTCCGGTTCTAGAAGTTTAATGAGACTCTGCTGCTCTGAGAGAGGCTTTAGAACCTCG
38111    TTATAGTAACTTTTGGTCTTTCAGAGATTTTGCCTCTATTCTGTCTTCACGTTTACAAAG
         GTCAGTCATGTCCTCCATAAAATTCAGTGATTCCACTGTGATACAGAAACCACGGCCCTT
         GCTTTTGGTGGGTTTCTGATTGGAGAGAGGAAAGGTCATCTTTCACCCACTATCTAGCAT
         AGCCATTGGCAGCATGATTCTTCCCAGGGGAGGCTGACGTTCTGGGTGGCTGGACCAGGC
         TACTTTGGCAGCTTGCTAAGGCTATGAATGGAGATGTTGGGGTACTCGGTAGGAACACCC
         [G,A]
         CCCTCATTATTACAAGGCTTCCATCCTCTCAAACTTTGGAGGCTGAGGTAAGAAGTGAAA
         GGTATGCTGTAAATAGGTCCTCTCTCCCAATGAGGCTTACTTGCCAGCCCAAAATCAAAG
         AGTATAATACATGTGCCCAGTTTTGACAAAAATTTATAAAACCTCCTTTTGTACATTAAG
         GCAAGAGTGAGGAACATTTGAGCCATGTAGGTGTTATGCTGGGGATTAGAAAAATGAGGC
         ACTGGCTACCAGTAACCTATATAACTGCGAACATTACTTCTCAGATACTTGTTAGTAAAC
Chromosome map:
Chromosome :10
```

FIGURE 3U

SEQUENCE LISTING

<160> NUMBER OF SEQ ID NOS: 4

<210> SEQ ID NO 1
<211> LENGTH: 3433
<212> TYPE: DNA
<213> ORGANISM: Homo sapiens

<400> SEQUENCE: 1

```
ctccgcacgc ccctgccccg tcgcctcccg ggagcggctg cagtccccgt tggctgcaga      60
cgggcagaca cccgaagtgt ccgcgccggc agccggaccg caagcgatga atatcgaacc     120
gcgctcccgg gcctggccga agcgcttcct gtgccaggtt tccggctccg ggtcccggga     180
ggaggatcgc gggccattat gcggagccgc cgccctgccg cgactttcag actccgacca     240
tggcctcgcg ctggtggcgg aggcggcgcg gctgctcctg gaagccggcg gcgcggagcc     300
ccgggcccgg ctcccccggc cgtgcgggac cgttggggcc gatcgccgct gccgatattc     360
cgcgcgcagg ttcataggcg gaagggactt gacttgtctc agatacccta tattaatctt     420
gtgaagcatt taacatctgc ctgtccaaat gtatgtcgta tatcacggtt tcatcacaca     480
accccagaca gtaaaacaca cagtggtgaa aaatacaccg atcctttcaa actcggttgg     540
agagacttga aaggtctgta tgaggacatt agaaaggaac tgcttatatc aacatcagaa     600
```

-continued

```
cttaaggaaa tgtctgagta ctactttgat gggaaaggga aagcctttcg accaattatt      660
gtggcgctaa tggcccgagc atgcaatatt catcataaca actcccgaca tgtgcaagcc      720
agccagcgcg ccatagcctt aattgcagaa atgatccaca ctgctagtct ggttcacgat      780
gacgttattg acgatgcaag ttctcgaaga ggaaaacaca cagttaataa gatctggggt      840
gaaaagaagg ctgttcttgc tggagattta attctttctg cagcatctat agctctggca      900
cgaattggaa atacaactgt tatatctatt ttaacccaag ttattgaaga tttggtgcgt      960
ggtgaatttc ttcagctcgg gtcaaaagaa aatgagaatg aaagatttgc acactacctt     1020
gagaagacat tcaagaagac cgccagcctg atagccaaca gttgtaaagc agtctctgtt     1080
ctaggatgtc ccgacccagt ggtgcatgag atcgcctatc agtacggaaa aaatgtagga     1140
atagcttttc agctaataga tgatgtattg gacttcacct cgtgttctga ccagatgggc     1200
aaaccaacat cagctgatct gaagctcggg ttagccactg gtcctgtcct gtttgcctgt     1260
cagcaggtag gttttacaaa ctccctttga cacatcactg catagcccca cagaactgat     1320
gtcccgcggc acagctgatg ggaagattgc ataaggaat agatgggaag gcattcagat      1380
aagagatcac aggtctgcat ttgatcctgg ctgagtgaga tgttggggct ggtcatttca     1440
ccttgctaag actgtttcct tatctgtaaa attgagaaga tcacctttct cccagggtgg     1500
ttgtgaggat tagctaagat cctatttgag atctttgtgt cttgtggtgt gccataggca     1560
tttgaggtag catcgtgatt atttccatat attttggcca ctggcaaagt gaacggtttc     1620
taagtcttga ttataggact ggactttggt ggtcctcaga gccccttaaa aggcatagga     1680
agcatcaagg gcctccaagc ataagaaatt ctccggttct agaagtttaa tgagactctg     1740
ctgctctgag agaggcttta gaacctcggc cattgcctca aaatgtcagg aagtcagtgg     1800
agtgcagtag acccacatag ttccttcttt ctccggattg agggactgag tcccccttaa     1860
tgtgaatgaa aggcttagga agcttcaaag atgttccctc gactgacaaa gcagacattc     1920
tcacagcctc ctccagaccc tgccacatgg cttgtggctg tactgaatgt tacttgaaat     1980
aagtgagaca ttagctggtg ttggaacatc tcgttaatag attttcatct tagtagtatt     2040
taatttgtta tgttgcaaag cagtaagatg ttcatcaccg tgccatgaaa ttcaacatta     2100
gctctttggt gtaaaattat agtaactttt ggtctttcag agattttgcc tctattctgt     2160
cttcacgttt acaaaggtca gtcatgtcct ccataaaatt cagtgattcc actgtgatac     2220
agaaaccacg gcccttgctt ttggtgggtt tctgattgga gagaggaaag gtcatctttc     2280
acccactatc tagcatagcc attggcagca tgattcttcc caggggaggc tgacgttctg     2340
ggtggctgga ccaggctact ttggcagctt gctaaggcta tgaatggaga tgttggggta     2400
ctcggtagga acacccgccc tcattattac aaggcttcca tcctctcaaa ctttggaggc     2460
tgaggtaaga agtgaaaggt atgctgtaaa taggtcctct ctcccaatga ggcttacttg     2520
ccagcccaaa atcaaagagt ataatacatg tgcccagttt tgacaaaaat ttataaaacc     2580
tccttttgta cattaaggca agagtgagga acatttgagc catgtaggtg ttatgctggg     2640
gattagaaaa atgaggcact ggctaccagt aacctatata actgcgaaca ttacttctca     2700
gatacttgtt agtaaacatg agtgaaggaa agcaagatgg actgagtgtg ctgaaatcca     2760
gctagcttgg taaagattcc tttacctagg ctcagattat caggataaaa ggaaaaagcc     2820 ttttccctg gagaagtcta tgagaaagtt ttggttgctc tatttgtaaa aatcttcaaa      2880
ttgttaagta cttgttatga accccaggat actaagttac cggttgagtc ctactttaaac    2940 cttaaggtga ctgggtgaga ggaggctggc ctcttcggac tgtgtttcac tctgaatata    3000
```

```
tttcagaaga aactaactta ctttccccta cacacacaaa ggagtaatgg ctatctctgc    3060
tttcatatat agtgggggaa aggggaaatg gacctctgca tagtatctgt cagtaatcta    3120
caagagactg aaaatgctg gttaggcggt ggctcatgcc tgtaatccca gcactttggg     3180
aggctgaggc agttggatta tgaggtcagg agttcaagac cagcctgacc aatatggtgg    3240 aaacccgtc tctactaaaa atacaaaaat tagccgggcc tggtggtgca tgcctgtaat     3300
cccagctact cgggaggcca aggaaggaga atccttgaac ctgggaggca gaggttgcag    3360
tgagccgaga ctgcactcca gcctgggtga cagagtgaga ctccgtctca aaaaaaaaa     3420 aaaaaaaaaa aaa                                                       3433
```

<210> SEQ ID NO 2
<211> LENGTH: 363
<212> TYPE: PRT
<213> ORGANISM: Homo sapiens

<400> SEQUENCE: 2

```
Met Arg Ser Arg Arg Pro Ala Ala Thr Phe Arg Leu Arg Pro Trp Pro
1               5                   10                  15

Arg Ala Gly Gly Gly Gly Ala Ala Ala Pro Gly Ser Arg Arg Arg
            20                  25                  30

Gly Ala Pro Gly Pro Ala Pro Ala Val Arg Asp Arg Trp Gly Arg
        35                  40                  45

Ser Pro Leu Pro Ile Phe Arg Ala Gln Val His Arg Lys Gly Leu
    50                  55                  60

Asp Leu Ser Gln Ile Pro Tyr Ile Asn Leu Val Lys His Leu Thr Ser
65                  70                  75                  80

Ala Cys Pro Asn Val Cys Arg Ile Ser Arg Phe His Thr Thr Pro
                85                  90                  95

Asp Ser Lys Thr His Ser Gly Glu Lys Tyr Thr Asp Pro Phe Lys Leu
            100                 105                 110

Gly Trp Arg Asp Leu Lys Gly Leu Tyr Glu Asp Ile Arg Lys Glu Leu
        115                 120                 125

Leu Ile Ser Thr Ser Glu Leu Lys Glu Met Ser Glu Tyr Tyr Phe Asp
130                 135                 140

Gly Lys Gly Lys Ala Phe Arg Pro Ile Ile Val Ala Leu Met Ala Arg
145                 150                 155                 160

Ala Cys Asn Ile His His Asn Asn Ser Arg His Val Gln Ala Ser Gln
                165                 170                 175

Arg Ala Ile Ala Leu Ile Ala Glu Met Ile His Thr Ala Ser Leu Val
            180                 185                 190

His Asp Asp Val Ile Asp Asp Ala Ser Ser Arg Arg Gly Lys His Thr
        195                 200                 205

Val Asn Lys Ile Trp Gly Glu Lys Lys Ala Val Leu Ala Gly Asp Leu
    210                 215                 220

Ile Leu Ser Ala Ala Ser Ile Ala Leu Ala Arg Ile Gly Asn Thr Thr
225                 230                 235                 240

Val Ile Ser Ile Leu Thr Gln Val Ile Glu Asp Leu Val Arg Gly Glu
                245                 250                 255

Phe Leu Gln Leu Gly Ser Lys Glu Asn Glu Asn Glu Arg Phe Ala His
            260                 265                 270

Tyr Leu Glu Lys Thr Phe Lys Lys Thr Ala Ser Leu Ile Ala Asn Ser
        275                 280                 285
```

```
Cys Lys Ala Val Ser Val Leu Gly Cys Pro Asp Pro Val His Glu
        290                 295                 300
Ile Ala Tyr Gln Tyr Gly Lys Asn Val Gly Ile Ala Phe Gln Leu Ile
305                 310                 315                 320
Asp Asp Val Leu Asp Phe Thr Ser Cys Ser Asp Gln Met Gly Lys Pro
                325                 330                 335
Thr Ser Ala Asp Leu Lys Leu Gly Leu Ala Thr Gly Pro Val Leu Phe
                340                 345                 350
Ala Cys Gln Gln Val Gly Phe Thr Asn Ser Leu
            355                 360

<210> SEQ ID NO 3
<211> LENGTH: 39982
<212> TYPE: DNA
<213> ORGANISM: Homo sapiens

<400> SEQUENCE: 3
catcaatatg gcaagaaaat gtcttggagg gtacctaaca ctccaacctc aaaacgacaa      60
ccttgatcgc tttcagttac acataggcca ttttgatcca tctgtactgg ctcttttcat     120
ttgtctaagg gcagcaaaat agactaaagt tgttttcaga ctgcacaaga gaagtctgtt    180
ctttagcact tacctgcata actcagatag tgttttaac ttcctcaact catgcttggc     240
ctagttgggt caaaagaact acttgtgaat tccgtatgtc caattggtag gttactgttt    300
tttctcaaga gtttagctat acagtaatgt tggaagtctt gaggaacttc agctgctgtc    360
cctacttagc cttgcaatac tacggcatct tttcttcttt ttctttttt taaagacgga    420 gtctcacttt gtcacctagg ccgaagtgca gtggcacaat ctcggctcac tgcaacctct    480
gcctcccagg ttcaagtgat tctcttgcct cagcctccta gtagttggg attacagaac     540 atgcaccacc atgcccaact aattttaaa tatttagtag agacgggttt caccatgttg     600
gccaggctgg tctcaaactc ctgacctcaa gtgatccacc tgcctcggcc tcccacagtg    660
ctgggattac aggctgagcc actgtgcccc gacctacag catcttttta agagcaatgt     720
tttctgtttt aatgtggcca agcaatctct aaacgaacat ggtctgacaa aattgtgtag    780
tgacatactt gacaactggg tgagcttgag tgtgatactt atttgaccat acggtatttc    840
ctctatatgt ttccttatct ttatatacaa aaaagggcaa atgataatgt cttagtcata    900
ggatcaagta caacccaagt gcttactgct acactctact tggcaaattc cacttatga    960 atgtttctta atatataaac ctaatctaaa ccaagataag ctacaggtgc atattaacaa   1020
tctttactca taaagttttg catatttta catactattc ttcaagatgg aaaaaacacc    1080
atcaaactgg cttattttca tagatgtctt tatatagtct atgatgtctt cattccataa    1140
aaaatccaca cgattaaata tgaaattaat gtacccagct atgaggctac cgcattcttt   1200
aacccaagaa caagaaaata catgaatcag agaactgcaa ttacctactt gctggtctat   1260
ttcctcatta gagtgaattt tttgaggact aaattgcatt tctctatctc taatgcttac   1320
cccctatctc actggctctg tgtgtttgag tgcatgcgct gaatgtttat atcacttaat   1380
ttctgttcgg aacacgctgt ctcttagcac cagtagatct ggccttagag ctaaggaaag   1440
aaggcctttc taacccataa ggggtactaa tcctgtacag actccaatat ctcccgggct   1500
gggtacacgc aggttcacac ccaggtgtga gcaagattgc caaactatac ctataaggcg   1560
tttggaggag agagtccaaa agtcacgaga cccggctaat ttagctacta tttcacaaca   1620
accctgatcg tggtcggact tgtttctagg aagatgcgat gggctggaac ttccttcaag   1680
```

-continued

| | | | | | |
|---|---|---|---|---|---|
| aacagattgc | aaaaggcagc | cgaccagggc | gtgtcaggtc | actgccaagg | gaagcagcag | 1740 |
| cggaaaccgt | cgcctccggc | ttaggctgcg | agcgggaaac | cccattctct | gagttatgtt | 1800 |
| tctgcctaaa | cacgcagaac | aaaagagttc | gtggctgcaa | gggtggcgcg | cggtagtatt | 1860 |
| tcttgctaat | aaaaggtccc | cacagggaca | tttttgctat | gactgcaggc | gtggccagtg | 1920 |
| cccctgcaca | gcttccggga | agaggtgggg | ataggaggct | cgccccgggg | aaggtcacgc | 1980 |
| tcgggtccc | cagaccaggt | ctccgcacgc | ccctgccccg | tcgcctcccg | ggagcggctg | 2040 |
| cagtccccgt | tggctgcaga | cgggcagaca | cccgaagtgt | ccgcgccggc | agccggaccg | 2100 |
| caagcgagga | agagcgaacc | gcgctcccgg | gcctggccga | agcgcttcct | gtgccaggtt | 2160 |
| tccggctccg | ggtcccggga | ggaggatcgc | gggccagagg | cggagccgcc | gccctgccgc | 2220 |
| gactttcaga | ctccgaccat | ggcctcgcgc | tggtggcggt | ggcggcgcgg | ctgctcctgg | 2280 |
| aagccggcgg | cgcggagccc | cgggcccggc | tccccggcc | gtgcgggacc | gttggggccg | 2340 |
| agcgccgctg | ccgaagtccg | cgcgcaggtg | aggttgggag | gcgcgcgccc | ggcggggctc | 2400 |
| agaggtcacg | gctccaatga | cagcagtggg | cggaatgaat | gggagcgggg | agcacgtgcg | 2460 |
| tcgcgacgcg | gggcgcgcg | gggtagctcc | gggtagctc | cggggtggga | ctccggagct | 2520 |
| gagggtgct | cgcggtggga | cggagccgcg | cgttggactg | aagtaggggc | gccctacacg | 2580 |
| gggttgcaga | aagcggtgtc | ctggggaccc | cgggagcgtt | ttgggggtg | gagaaagcgg | 2640 |
| tgggatccgt | gtcctggggg | aagcgcagga | gcgatcagat | tgaccgctgc | tatatggaca | 2700 |
| aggttaatta | agcctggaga | gcgactgcag | ctatttactt | tggagttaga | ggaagacaga | 2760 |
| tcttgcctga | aattttagag | ccaaagtgct | cagagctctc | tccgagaaac | ggaggatcga | 2820 |
| atcggcctcg | gaatagtccg | aaaaggtctt | gtggagaatg | cagggctggt | gctagggtgg | 2880 |
| accggacctt | agttgtccag | cagtggcttc | gggaggagag | cacacctgga | tggggctgga | 2940 |
| atgacactgg | aaggagaaag | gcccgaggcc | gtcaggagga | gagaaaccct | ggagtcatct | 3000 |
| aaagtcagaa | tctcagtgat | agcccattct | ttcagggtct | cctctgctgc | ctttgggttc | 3060 |
| cgatctcctt | tttctccctt | tctggtcagt | ttagcccctg | taaatggaca | ctgtgagccc | 3120 |
| ttctgcactt | tgtaatgatt | ctcagtgtgc | catggggtag | gcccatgcta | ttagcataac | 3180 |
| cgtgcaaaat | ctatggactc | actgttactt | aagtttattt | gaatttagta | ctcttttaat | 3240 |
| tcagatttgg | tatactttat | gtgtccgtgt | tctcatcaaa | catcatttcc | cagtatgaaa | 3300 |
| tatataacac | ttataaatat | ctactttgta | ccaaagtaga | tgcgtatcac | aaattatcca | 3360 |
| aaacaaggct | tgggccaggc | acagtggctc | acacctgtaa | tcccagcact | ttgggaggct | 3420 |
| gaggtgggag | aatcggttga | ggccaggagt | ttgggaccag | cctaggcaac | atagcaagac | 3480 |
| tctgtctcta | taaaaaatag | aaaaaattca | ccaggtgggg | tggtgcatgc | ctgtagttct | 3540 |
| acctactcag | gagcctgagg | gaggaggatt | gttcgatccc | aggagttcaa | gattacagtg | 3600 |
| agctgtttat | tgtgatagtg | ccagtgcact | ccagcctggg | caacagtgtg | agaccctatc | 3660 |
| tctaaaaaat | ctaaagcaaa | aaagacgttt | ggagaccaag | tggcagctgg | gcaactagac | 3720 |
| aatgctagag | agtaaagaga | acagaatatg | ggggtgagg | ggcacgtggg | agaagaggct | 3780 |
| tagaggagga | aggtaggctt | tgctgtgatc | catttcagga | ctgttctctc | cagacttcag | 3840 |
| atatttctag | ttccacagaa | gaagccagta | tttgaagaga | tgggtgcatc | caccctctta | 3900 |
| tgccactaca | tgcttcttct | tcttcttctt | tttttttttt | ttttgacaca | gagtctcact | 3960 |
| ctgtcgccca | ggctggagtg | cagtggcgga | atctcggctc | actgcaaact | ccacctccca | 4020 |
| ggttcaagcg | attctcctgc | tgcagactcc | caagtagctg | ggattacagg | cgtacaccac | 4080 |

```
gacccccagc taattttttgt attttttagta gagacagcat ttcaccatgt tgcccaggct    4140
ggtctggaac tcctgacctc aagtgatcca cccctcctc ggcctcccaa agtgcgggga      4200
ttacaggtgt gagccaccac gcctggcctg acacttcttt ttaaaaaagt ttcttgccca     4260
ccaagcaacc ttagccaggg aaagtgtgct tttctggaga gaatatgctt tatggcctcc    4320
ccgtctgcat gacgacaagg aggaattctg tggactcatg atgccaagat catgtatttc    4380
tgatgtgtgt gtcagtgatg cctttcacta tacgttaata tgttagcatt ctggtgtctg   4440
cctcaggcat gtgtattttg gttacttcaa gtctcttagg gcctgatagt ccttggggac   4500
acagaactac aataactaag ccacagggac aaagagcggc aataattaag ccacgtcttg   4560
ctctccacca gagctctact acctcctaat ggttgtacat tcttctgact tcactagtag   4620
tgtgaacaaa tattgtaata caataaaaac cagtgtgcat gtgatcgtgc caaatcactt   4680
ctcaatatat ctttgatttt ttttttttaat ttattttttt agagacgggg acttttttgtg  4740
ttggccaggt tggtcttgaa ctcttggact caagccattc ccccctcccc cccacccccgc  4800
ttgaggattg gcacacggcc atgtatttga ttcttaccca gcactttctc tttagctgag   4860
cgtggtggct cacgcctgta atcccaacag tttgggaggc cgaggcagga gaatcccttt   4920
agctcaggag ttcgagacca gcctgggcca cttagtgaga cctcctgata cggtttggct   4980
ctgtatgccc acccacatct atctcgaact gtaatcccca attacatttg gggaccaggg   5040
agggtcaagg gagggaccag gtggaggtaa ttggatcatg ggggtggatt ccccatgct    5100
gttctcatga tagggagttc tcacaagatc tgctggtttt ataagtgttt ggtagttcct   5160
cctgtgttca ttctgtctcc tgccgccttg tgaagaaggt gcttgtttct ccttctcctt   5220
cttccaccat gattctaagt ttctgaggcc tccccagcca ttcagaactg tgagtcaatt   5280
aaacctcttt cctataatta taaattgccc agtcatgggt aatttcttta tagcagtgtg   5340
agaatggacc aatacagata attggtacca aagtagttgg cattgatata agatacctga   5400
gaatgtggaa attactttgg aactgggtaa caagcagagg ttggaatagt ttggagggct   5460
cagaagaaca aaggaagatg taggaaagtt tggaaattcc tagagtcttg ttgaatggct   5520
ttgaccaaaa tgctgaaagt gatatggatg atgaagtcca ggctgaggtg gtctcagatg   5580
gagatgagga gcttcctggg aactgggcaa aggtcactct tgctatgctt tagcaaagag   5640
actggtggca ttttgcccca ccctagagat ctgtggaact ttgagcctga gagagatgat   5700
ctgaaattgg aacttaaatt taagggggaa gcagagcata aacgtttgga aaatttgcag   5760
cctgaagatg tgatagaaaa gaattttctg gggaggaatt caagctggct gcagacattt   5820
gcataagtaa caaggagccg aatgttaata gccaagagaa tggggaaaat gtctccagag   5880
catgtcagag accttctctg cagcccctcc catcacaggc caggaggcct aggagggaaa   5940
aatggattca tgggctgggc ccagggccct gctgctctgt gcaagagcag ccttgggact   6000
tggtgccctg cttcccagcc gtagctaaaa ggggccaagg tacagcttgg gccattgctt   6060
cagagggtat aagcccccaag ccttggtggc ttccatgtgc tgctgagcct gcaaggtgca  6120
cagaagacaa caatttggga acttctgcct agatttcaga ggatgtatgg aaatgcctca   6180
atgcccaggc agaagtctgc tgaaggggggg agaaccctca tggagaacct ctgttaggac  6240
agtgcagaaa ggaaatgtgg ggttgcagcc cccacacgga gtccctgctg gggcactgcc   6300
taatggagct gtgaaaggag ggccaccgtg ctctagaccc cagaatggta ggtccaccaa   6360
cagcttccac cgtgcacctg gaaaagctgc aggcactcaa tgccagccca tgagaatagc   6420
```

-continued

```
agtgggggtt gaaccctgca aagccacaga ggcagagcca cccaagttct tgggagccca    6480
cccctttgcat cagtgtgacc tagatgtgag acatggagtc aaagatcatt ttggagcttt    6540
aagtaatgac tgccctgctg ggtttggact tgcatgaggc ctgtaagccc cttcgttttg    6600
gccaatttct accatttgga atgggaacat ttaaccaatg cctgtacccc cattgtatct    6660
tggatgtaac taacttgttt ttgattttac aggttcatag gcggaaggga cttgacttgt    6720
ctcaggtaag actttggact tggacttttg agttaatgct agaatgagtt aagacttttg    6780
aggactgttc ggaaggaatg attggttttg aaaaatgagg atatgagatt tgggaggagc    6840
aaggggcaga acgatatggt tggttctgtg tctctaccca aatctcatct caaattttaa    6900
tccccatgtg tcaaaggagg gcctatgtgg aggtaattgg atcctggggg cagattcccc    6960
catgctgttc ttgttatagc gaattcttat gagatctgat ggttttataa gtgattggta    7020
gttccttctg tgttcattct ccttcctgct gcctagtgaa aaggtgcct tgctttccct    7080
tttcttctg ccatgattgt aagtttcttg aggcctccct agccgtttgg aactgtgagt    7140
cagttacacc tcttctttt ataaattacc cagtcttggg tatttcttta tagcaatgtg    7200
aaaacgtact aatacacctc gtttctaaaa atcagctacg cattgtggca tgttcctgta    7260
gtcccagcta ctcagtaggc tgaggtggga agatagcttg agcccaggag attgaggctg    7320
cagtgagcta tgattgcacc actgcactcc agcctggaaa aataaaataa aagtaaattc    7380
atgagaggca aggttgactt tcagagagtg tgtgagggaa aggtaagaaa caaaatcgga    7440
attagaaaat gactgttgcc cctctctttt cattcttcac tgcttttctg agcacctctc    7500
acctcccttt gaaaaactgc tctaaagtac ttttaaagca gaaaatagta gcttgattga    7560
atagatactg tattaaatgt atattgtgta ccaggctctg agctaagagc tttacatctg    7620
ctctctaaat taatctccac ctctctccat gagtaggtat tatcagaaag acatcacaag    7680
gtaacacaaa tgttgagatt tgaaccgaga tctgtcttcc aaagtccatg ctactaataa    7740
ttgttaggcc acttggtggt aaaaagcgtc ccctgtatta attagctgtg taattttaat    7800
ccttcaaccc agattagggg tctataactg aataaccaaa aagttattca gttagaatag    7860
ttcagttagt tattaactaa tcatagttat ttggtcaagc gcagtgactc acgtctgtaa    7920
ttccagcact tggggaggct gtggcaggag gatttctaat aatagtaact attactagag    7980
acctgataat aattattaag tctcttactg aagaagtttt actcttccat taagatgccc    8040
ttatttataa gtattataat aaaatactga actcatatga attaattacc catgtagact    8100
gaaagacata ggttgtcata taatggttgt catataaagc atgaaggagg attgtcactt    8160
tgttttcttg ttgcactgta attgcctggg atatcatgaa agttcttact ggtttaatga    8220
atatgtaatg ctgtggggga aagaatgaaa ctcaggccaa ctactttgac tggtgtctgg    8280
caaagtcaac tttcattgcc attttaatat ggcgccgggc gcggtggctc acgcctgtaa    8340
tcccagcact tgggaggcc aaggcgggcg gatcatgagg tcaggagatc gagaccatcc    8400
tggctaacac ggtgaaaccc catctctact aaaaatacaa aaaattagcc aggcgaggtg    8460
gtgggcgcct gtagtcccag ctactcagga ggctgagaca ggagaatggc gtgaaccctg    8520
gggggcggag cctgcagtga gccgagatag cgccactgca ctccagcctg gacgacagaa    8580
cgagactccg tctcacaaaa aaaaaaaaa aaaatatgg ctagagcaat acatgttcat    8640
tagagaagaa tcagaaaata tctaccaaaa gaaggaataa aacaaaacac ccccacaatc    8700
cgattcattc cagaataact acttttaaca ccctggtttt tgtgctttca aactctgttc    8760
tcccatttcc aaaggatgtt gaggaacacg aacttaaaat agacagtgtt tgtataaata    8820
```

```
taaattcctt ccttgctatt gaaatctttt ttcctctgac caatcttagt taaatggaag    8880
gaaattgttt taaaactaat tttcaggtct ggaaagatag atatgaatat ggaaatgact    8940
ttctttgggg gaagggatgg actgaagatg gttattattt tctccttttt tcttatttat    9000
gttttctgca atgacaagta ttttgtaata acaaaaggaa actttaaaat tattcttcct    9060
ctaaagtttg caatctacct gtaaatgggt gattagaaga taaagattat aattatgggg    9120
gttttatcat ccaatgttac agttttcag gaatattctt acaagtttct tgacatttt    9180
atttttataga taccctatat taatcttgtg aagcatttaa catctgcctg tccaaatgta    9240
tgtcgtatat cacggtaagt ttacagtcca tactgcaact actaaaatta tccattttta    9300
aatttattat tgtttaaaaa attttttttg tagcgatggg gagctcactg tgttgcccag    9360
gctggtcttg aactgctggc tcaagctat cctcccaccc tcaggttccc aaagtgctgg    9420
gattgcagac ataagcaccc ggcctaaaat tattaattat attgcctgta aatttctatt    9480
ctaaattgta gatctctgcc tattcaaaaa acaggaatat aataaagttt gagctcaacc    9540
cagagcacaa tgaacatagt ttagttttc tttgattttg tgggttctca aggccctatt    9600
tataaaagtg atctattgat ctgtcattta gcaagaatag aattctgtat gttttttccaa    9660
attataatga ccttttcaga ttcatgatta atttctagca aatatttggg ctgaattttc    9720
cgtatctgag tctactaaat atatatgtat ataaaactta cttgaaaatg aagtcatgtg    9780
cattttgca tgtcccaggt ttcatcacac aaccccagac agtaaaacac acagtggtga    9840
aaaatacacc gatcctttca aactcggttg gagagactt aaaggtctgt atgaggacat    9900
tagaaaggtg agttttttat tctgctgtga tgtaatgttt tagcttacca aaacttacta    9960
aaatttatt ttattttta ttcttataat tattattatt ttttgagctg gagtctcact   10020
ctgttgccca ggcttgagtg cagcggtgca atctaagctc actgcaaccc ttgcctccca   10080
ggttcatgca attctcctgc ctcagcctcc tgagtagctg agattatagg catgcgccat   10140
cacacctggg taatttttgt attttagtg aagacggggt tttgctatgt tggccaggct   10200
ggtcttgaac tcctgacctc aggtgaccta cccgccttgg cctcccaaag tgctgggatt   10260
acaaaaaaac agtgcaggtt tcagatctg tacaatgcag tttgcaatct tgattcacgt   10320
atggtcaagt ttcaaatgtt tcttgagaag aatacatatg acccagtgcc aggcaatatg   10380
aagaatgcaa tatgtattta tgtccagaaa gaggttatgg cagggttggg aacctgaagg   10440
aaaaaaatgg tccaggtagc tcatgcttgt ccaatgagtt atcccacctt tcctcttaaa   10500
acccaccacc tcccagtgac tccagctgtc tcttccttat ctaattctga atgtcattgc   10560
cagtgtgccc caaatatggc tttcttcatt caactctttt tcctgaaaac tttcagtagt   10620
tcccaacctc acgtggttgg gcaccgtggc tcgtgcctgt aatcccacca atttaggagg   10680
ccaaagcaag aggactgctt aagcccagga gtttgaggct gcagtgagcc atgatcccgc   10740
cattgcactc cagcctgagt gagagagcaa gacatttttt ctgtctttag aaaaaaattg   10800
gctgggcacg gtggatcaca cctataatcc tagcactttg agaggacacc acttcctgtt   10860
tcacagacag taggggctgt ggaggaagaa ctccttcagc tcctgctctg tcgcaattgg   10920
ccagcttgcc tgcgccttct ctggcgattg cctgctctcc tcccacccgt ggaagtcatg   10980
tcccttccct ctctagggc agtcccttag ccaacctccc tagtttctta ggaactcccc   11040
cagacatggc ctctccctct gtctgcaaac tttcattggc atggtcttcc atatccattg   11100
ggtgttcagt ttcttcacct gcattttaa aaggcccatc cactgaccca gtgcttcact   11160
```

```
ccctcccttc cctcacagta tccctgccc tctgccttcc tccagtgcct tcatgttccc    11220
tccactattg cactggggcc cccttccag cctctcctct gaagctggtt ttgcttgggt    11280
cactgatagc ttccctgtgc taaatccaat ggatgtgtta ccagcagcaa atttgtacag    11340
gtctgcagca acctcaattc ttgcctcctc agaagaaaga attcgactga ggggcctaag    11400
gcagaaggag agacggaggc aagttttaga gcaggagaga aagtttatta ttaagtgtag    11460
agtaggaagg gaaggaagta aagtacactt gtaagagggc caagctggtg acctgagaga    11520
aagtgtggtt tgaccttgga atttgggttt tagatgttgg catacttcca gggacttgca    11580
tcccatctcc ccggtttctt cccttggggt gggctgcccg catgcgcagt ggcccgccag    11640
tgttggggag gggagcatgc tcagtgtgtt taccggagtt ttgcgcatgc tcacgtgagg    11700
cattcttccc ataccagtcc cagttttcct agaaggacat acaccaatta agctctgcca    11760
ttttgcctct tagtgtgcat ggttgagccg actcacccaa ctcccgagat cttattggga    11820
agctgatcac cagtttcagg ttttgtatc tattgagaga ctgccgtccc ttggcaccag    11880
ctgtgaccaa ttagtatttt agcgacacag ttaacaactg cttgaccatc acgtgatggt    11940
cgccttcctg ttgtgggtcg gggagccctc tcctgccctg ctcatgcctg actagctatc    12000
tactgtaacg gacacttcct ggttttctga ccattgggca ctattgactg taacccctcc    12060
ttgaaacatg gttcccttca ctctgcactt tgttcccct ccttatcctg aggcttttct    12120
tcggttcatc acctccagct cacttccttt aattttgcca ttccctgggg ttccgtgggc    12180
cccctcctct ctctcttcct tatatatctg tgtccatact tacgtctctc aaataatatc    12240
actactccag gttgaatcac atctcccaca cccaggtagc taactactca ccgggaacgc    12300 catgggcgg ccatgacggt ctcaggctta actcagctga gactctactt ttcccccacg    12360
agttgtttgt tctgctgttt tcctgttcct tgggaacctg ggaagaaccc aggacttgtc    12420
cctctccttc ccctctatgt ccttctagtc tgcctcttgt cagtccccac tgccccaggc    12480
caggcaattc catgcccctg gtcctttcat tcgtgctctt ctcctccctg tctcagcttc    12540
cgaggtgaca gcttacctgg gtgacagcac cacacccatc acactgtgtt gtgtcaacgg    12600
cagtgatcgt tttacttctc cccatctaga ccctgagctc cttgtaggca aggcttgtct    12660
tactttacct ttgtgacctc tgtgtctgtt acagtgcctg gcactaagtc ggtaatttac    12720
tgaatgaacg atgggcccac tttgttgtgt tcacctgtgc cgagctgagg ttcattgact    12780
cccactgcat ccagggata aactctgact tagtcttgga gtggcagata caagcgacac    12840 acaccgtca gctggaaggc tcttgtcctc tttgtgaatc agaaccctgt ttaggcttct    12900
aatcccacat caaagcccat ctcctccatg aaatactcag tttttctagc ctgcactgat    12960
ctcttccttc cctgaacttt caatgtattt aatgtacagc attgttcacg ctaccactgt    13020
attcgtcatt gattgtttca tatttgcaaa atgtttctct ccccagttca gttgtaggct    13080
ccttgtaatc cggcagccca tgccttatat gggctctatg cgcttacgtg ggcctctatg    13140
aaccctcaaa atgtctttg ccaaataaag gccaagccag atggactgag cctgttct     13200 tctccttggc tgtggcctta ctatcttcct gcccctcgta aacagctttg cctgggag     13260 tttgaggctg cagtgagtta tgatcgtgcc actgccctga ggcctgggtg acagagcaag    13320
accttgtctc taaaaaaatt aaataaaaa atttaaaaaa caactttgc caccctaccc     13380 atcacacccc acccgcctga cctgcttcac aggctcccga cggccactgg cttccacctt    13440
ccccatcttt ctcttcccgc ctccatcttt taagctgcga accagcccct gttcctttca    13500
ctgtccagct gtcaatgagc ccagagtccc ttagccacct agtgctttct tccccctcct    13560
```

```
gctgtctctt ggggtcttct ggtgtctgat tctgtcagcg gggcaggtgg cagtacctgt   13620
tctagcattc aggccacttg gggctgatcc acgcattgtt tatgttctag cctgcaggac   13680
agccaggtgg atggccctgc agcgtgggag ccttgcccac ggagtgttga atttcttaat   13740
tgaaatgaat acacttaaat taaaccaaag ttttgtagaa gaaatcctgg ccaggcacgg   13800
tggctcacgc ctgtaatccc aacactttgg gaggccgagg cgggtggatc acctgatgtc   13860
aggagtttaa gaccagcctg gccaacgtgg tgaaatcccg tctctactaa aaatacaaaa   13920
aattagccag gcattgtggt gggtgcttgt aatcccagct gcttgcgggg ctgaggcagg   13980
agaatcgcat gaacccggga ggcggaggtt acaatgagct gagatcgttc cattgcactc   14040
cagtctgggc aacaagagcg aaactccgtc tcaaaaaaaa aagaaatcc tgttggcttt   14100 ctgtgcagtt ttttgatgcc attgtgacac agagaaactt tatttcagga actgcttata   14160
tcaacatcag aacttaagga aatgtctgag tactactttg atgggaaagg gaaagccttt   14220
cgaccaatta ttgtggcgct aatggcccga gcatgcaata ttcatcataa caactcccgg   14280
tgagctcttt ttttcattcc tttcttgttt ttatatttgg caagtctttc ttcccggggt   14340
tacttactgt ttcatttccc atttaagaat tagcatatac cggctgggca tggtggctca   14400
tgcctataat cccagcattc tgggagcctg aggcgggtgg atcgtgagat caggagtttg   14460
agaccagcct ggccaacatg gtgagacccc gtctctacta aaaatacaaa aaaattagc   14520 cgggcgtggt ggcaggtgcc tgtaatccca gctacttggg aggctgaggc aggagaatcg   14580
tttgaatctg ggaggcggag gttgcagtga gccgagatca cgccattgca ttccatcctg   14640
ggaacagagc aagactccgt ctcaaaaaaa ccaaacaaaa caaaaaacat gggggatttt   14700
taaaacaaaa ctttggaggg gatttttaata aacgatagaa ggtatatctt aagaaacaga   14760
gcacgaggga gaaactacta cttactgatt tttatatttt cctttattaa gcttttcagt   14820
tgtcccatta aatgttccct actagattac ggggagttct taacttgagg ttcacgggag   14880
ttgtgggatg tctgtaaaca acttgacatt gtatgcaaaa ttttgtgtat atttggattt   14940
tttggggaag gatttctatg gcttacagtt tattctcaaa gggaagtagg gccctaaaag   15000
ctcaggaccc cgtgtttgtt ttctctctga atcttgctaa ccatggtgtc tgggtagaga   15060
aagtaggaat ccacacaaca gtagactcag acttgacatg tccagaacac agagttgtgg   15120
tggatcctga gacttgcccc cagatccccc gtcagtgcac gactctgccc cagctgctgt   15180
atcaggtatg gttggtacct gttggccttc atttcttagc ctcttcaagg attgccttgg   15240
ctacaaagag tcctctcacc ttaggctgtg ccccttcggg aggcagccca catccaggga   15300
ctgatagatg aagggccatt ctacctgcac accctagagg gtgtttcagg ctgttgattc   15360
cagctcagct tctcctgcta cccagtcctg tatcctctcc ccctccctca ggtgtcagta   15420
atcccaaggg ataatcccga ataaacatcc tgtcctttaa acttcatctc agagtctgcc   15480
tcctgcagaa cctaacttgc aacagagctc agcaaaaccc aagctcattt tattaaagaa   15540
cccagatcaa aaaagagctt tatgggctgg gcacagtggc tcacgcctgt aatcccagca   15600
ctttgggagg ccaaggtggg tggatcacat gagttcagga gtttgaggct agcctggcca   15660
acatggtgaa accccatctc tacaaaaaat ataaaaatta gccagtcgtg gtgacacaca   15720
cctataaatc ccagctactc aggaggctgg ggcaggagaa tcgcttgaac ccaggaggtg   15780
gaggctgcag tgagcagaga ttgcgccact gcactccagc ctaggggaga ctctgtctca   15840
aaaaaaaaaa aaaagaaaag aaaaagagct ttatgataga tttctataaa attgcttcac   15900
```

```
tcactgaatg cagcacagtt atagtgtctg catgtttctc agacaagcca aacctaccta    15960
gcctgctcag ctgcctcatt gaagacactg ttatcactgg cacctggatc ttggcaccat    16020
ccattcctgt gtgaaactct tttagttcta agaagtgaat atcattgcca gcaatcagga    16080
taacagacta cccaaattgt gctgtacaga gatctgttga tatcaatttt gcaaatagcc    16140
aatggcattg gattacatta gtccagtttt caaagctgaa ctagatgttt aggggtcaa     16200 attattagac acagttttca cagtagataa caggttgaga gtccaggtgt gataacaatc    16260
ctgtattcag aggaggtaac ttttatagca ctataaaaaa ctaaggaaat taccaaagcc    16320
tatccctgaa aagactgtaa caaaacagcc atttagcact gactggctcc agtgattcca    16380
aaggtcaggc cactaacaac tgtagagcca ttcctggttt ctgtgtgttc tgtgtcactg    16440
agccagccac tgctgctgct gtttatggga taggcaagaa ggttgctacc aaaggaaatg    16500
gttttgtctt tcacctagga gatggttctg tggatatgtc catagtcact gttaaaacgg    16560
atctttgaag tacattctac agtaagggac acccattaag ctggagattt tgatgagcag    16620
atggtcatca tttcatgcat gagtgcaagg tcaagcataa gaacctcagt gagagcaaga    16680
gggctgcagg gcttgtgacc gtggtgtgtg caccttgttc agcaccctcc atgccaggat    16740
gaggctgatt ctgtctgcaa aggaatcaac tcctatactt tttttttttt ttttgtcttg    16800
ctctgtcacc caggctggag tgcagtggca caatctcagc tcatttcaac ctctgcctcc    16860
caggttcaag cgattcttct gcctcagcct cccaagtagc tgggattaca ggcacacacc    16920
atcacgccca gctaatgttt gtatttttag tagagacggg gtttcatcat gttggccagg    16980
ctagtcttaa actcctgacc tcaagtgatc cgcctgtctc ccctcccaa agtgctgaga     17040 ttaaaggcat gagccaccgc gcctgggcac tcctacactt tccttaccca tccccaattt    17100
gaaagaactg aatgctggtt agtccatagt accctggacc ctatagagaa agctctgcac    17160
agagcaacct ggataagttg tagatccagg tatcatcata ggggtctctc tccacatatc    17220
ccaagattca gaagctcttg taatttcttc ttcagtggca agcaaataag caatagtgtg    17280
aaccctgcat catttatgat gcaactttgc agacatccat tatatccaca gctaaatctg    17340
aaaatattca ggggttgctg cttttagata ccaattattt tctcttgaca ttaaaatgct    17400
aacaaatcta tgactgttag gatcaagtta aaaaaattcc cactgaagag agacagactt    17460
tattctgagc cttacgtgtt tctttaggtt tagaaggtga atgagcagtg gctggggagg    17520
atggcctaga agttgagct cacaggcttc ctccctgcac tctgccattc cttagattgg     17580 aggcgcccttt gatacagatc cctccctaca cactgggggt ttacttgcaa tttaagactt    17640
cacattttat attagtatga acagggaaaa tatattttgt aaaaccacat gtaaacctcg    17700
taaaggattc actggtaggg tcattatatt attctgtcta tttttaggta tgtttgaaac    17760
tcttcattat taaaaaaatt tttttggccg ggtgcggtgg ctcacgtaat ctcagcactc    17820
tgggaggcca aggcaggtgg atcatgtgag gtcatgagtt tgagaccagc cttgccaaca    17880
tggcaaaacc ccatctctac taaaaataca aaattatct gggcgtggtg gcacatgcct     17940
gtagtctcag ctacctggga ggctcaggca gaagaatcac taaacaagg aggcgaaggt     18000 tgcagtgagt caagattgcg ccctgcact ctagcctggg tgaaagagca agactccatc     18060
tcaaaaaaaa aaaagataat ttttaaatc taatgaagga ggaagaaaa gtcctgcag      18120 gcatgctgaa tcatagcata ctcttgcagg tgtgaagtac agaggacgta gccaactctc    18180
aagaccaagg gcttcatttt ccatgctacc ttgcctgtca cctctcccag atcctgggaa    18240
aatgtgatcc actatttcac agtaggaaat agaaatggtg cccagttttt tgaaggcttg    18300
```

-continued

```
attcagtttg gcattttgga gatgtcatct taaggacagt gtgaggtttt tctgtaatct    18360
gtgcattttg gtcatctgtc ccaccctcat gttatggata agcagtggca gcatttccca    18420
gatgtaagct gacacacact aaagctgaac tggataaaaa atacatcagg taaaactatg    18480
gaacatctga aatatgatgt atattctacg tagaagctgt gttacagtac caaataacat    18540
ttcagtttca tcctgatttc atcagtcaac aatttagcca tgcaaaatga cattttttat    18600
tctatttatt tatttattcg gagacagagt ctcgctctac cccccaggct ggagtacagt    18660
ggtgcaagtc tcagctcact gcaacctcca cctcccaggt tcaagcgatt ctcctgcctc    18720
agcctcccaa gtagctggga ttacaggcac ccactaccat gcctggctag ttttttgtatt   18780 tttagtggag acgtggtttc gtcatgttgg ccaggctggt ctcgaactcc tgacctcagg    18840
tgatcctcct gcctcggcgt cccaaagcgc tgggattatg ggcatgagcc actgcgccag    18900
gcgcaaaatg acattttttag atggatatat agtctatgaa atttcaaaat attttaagaa    18960
atctttgttg taataatagc ttcagattac caaaacaact ctagtatctt ggtgagtgct    19020
gccaatttca ttgcaacttc tcagcaggag ccccgtctgc tgatgtaatt tatcataatg    19080
gaagtggtgc ccaacttctg aatgcatgag aaaggctaga ccttacctgt tgttttaagg    19140
taaggtctac tgctaactag taggaggtgt ctaatttatt agactgaaat tcacttgcaa    19200
aaatattcta aaagccttat attaaaaaaa aactgtaaaa gtttatatct tttcctgtgc    19260
attcaactca aagaagatag ggcctagtaa atttacctga aaaatattta agtattctaa    19320
tataaaaact gaatctcact gagggattca ggtggcttaa aactcacctg aaccctgaac    19380
ctctattttc tcatttactg aagtttattg gggttttttgt tttttgtgt gttttttttga    19440 aatgaagtct ctgtcaccca ggctggagtg cagtggcata atctcggctc actgcaacct    19500
ccacttcccg gctcaagtga ttctcctgca tcagcctctc aagtagctgg gattacagat    19560
gcacaccacc atgcccgact aatctttgta ttttaagtag agttggagtt tcaccctgtt    19620
gtccaggctg gtctcgaact cctgacctca gtgatccgc ccgcctcagc cttccagagt     19680
gctgggatta caggcaggaa cctgtaactg tgcctagact acagaagtgg tttttatatg    19740
ctaatttgtc cctaccctcc actgcttttg ttttaatact ccccccttag aagaatttgt    19800
tgtgatctag acatattaag aagttgtaac tgaaatatta ataaagaatg aggccaggcg    19860
tggtggctca cacctgtaat cccagcactt tgggaagctg aggtgggtgg atcacctgaa    19920
gtcaggaatt caagaccagc ctggtcaaca tggtgaaacc ccatctctac taaaaataca    19980
aacattagct ggatgtggtg gtgtgcacat gtaatccaag ctacttggga ggctaaggca    20040
ggagaatggc ttgaacccgg gaggcagagg ttgtagtgag ccgagatcac accattgcac    20100
tccagcctgg gcaataagag tgaaattcca tctcaaaaaa aaaaaaaaa aaaaggaatg    20160 agtagcactg tagacatgat ttccaggctg agagcagttg aaagggtcta gggtttagtt    20220
ctaaggctgc tggtaagagg agccagcgtg acatcatatt ttaaaattat atgtaaagca    20280
agatcaaaag ctttcctcat gctgatttag tgtcgatagt taaattacag cacctttttat   20340 gtagttatac ttcatttttc attgctttct gccgggtctg aggaattgga atgagcatta    20400
ccttgtgcag atgttcagat tcgatttttta aagaaaaagt catatttcag aatccctctc    20460
ccttttttcc cctctaagat acaacctgat ggtatttgaa ataagcatt tggaataagt     20520 gcaacatttg gttagtgtgt gtttaaatga ggatatgttt taggttccaa atggttatttt   20580 cgccagtttg attttcttga aatttagttt ttaaaaattg ccatagatga tggtggtaat    20640
```

-continued

```
aatgattaaa atgaaatggg ggacattccc tctgaactgt aaaatttata tctgtgtcct    20700
gtcttcttga gcctacttat cctatagttt gtgttaaact tgggaaataa agtttaaat     20760
ttctaatgag aaggttaaat gtgagttgga agaaagtttt acaaacatct tctgttggtt    20820
actgaggttg tcatactaaa cgtttaattt aagacattac tacgcggggt gcggtggctt    20880
acgcctgtaa tccacacttt gggaggccaa ggcaggcgga tcacttgagg tcaggagttc    20940
gagaccaacc tagccaacat ggtgaaaccc catctctact aaaaatataa aatttagctg    21000
ggtgtggtgg tgtatgcctg tagtcccagc tactcatgga ggctgaagtg ggagaatcac    21060
ttgaacctgg gaggcgaagg ttgtgagcca atattgcacc actgcactcc agcctgggtg    21120
acagagcgag accctgtctc aaaaacaaga aaagacagta ttaaaagcct tgaacattga    21180
gacagttgag tctttaaaat acttttaaaa aatgcttctc acctatcttc cctatccacc    21240
ccaaaattta attgtaaact tataaactta aacacctgac caagaacact gttataaaga    21300
tgattcttca gcccaataag atcagccaga cttctgatcg tttactgttt ttttggctaa    21360
tggtacaatt tctacttctt caatggggaa ttcataaaat gtagttgtgg cagggtttct    21420
catacatttg taaatgtata gaatggctg tgtggtgaag ccagagtttt ataccgttt     21480
ctcttagaga aataacattc tttatcctag atccgatgtc cagttttcac aagctgattg    21540
ctgagaaggt tctaggcggc gtctgttaaa aagcattgct ttctgttaat tagacatgtg    21600
caagccagcc agcgcgccat agccttaatt gcagaaatga tccacactgc tagtctggtt    21660
cacgatgacg ttattgacga tgcaagttct cgaagaggaa aacacacagt taataagatc    21720
tggggtgaaa agaaggtatg gttttttggt tttttttaaaa tctctcttac tgaatcacac    21780
gcttttcgga ccgcatttgt ttctcagatt tgtctcatta aaaatatgct tgctcaaatg    21840
taatgtggtc ttctgaattt caaaaaagta ttcatgtctt gtccaaatac agatatttga    21900
taaataaata ataaaaaata ccatggaaaa ataaacttag tatttctaat agaattcctt    21960
tggttataag gaaagggatt ttcatggtg tccaaaaaat gtatttcatg aggaatcata    22020
cgttttactt ttgggcttag attacccaga ttcagtttaa ttttttaaac atttgtataa    22080
ttgagtgctg catataaatg ccaaagcaaa caaataaaac taataaaaga aaaagaaac     22140
ctcagagaga tactgttctg ccatgaaaat tctgtctttt gaaatagaag ttctgtaatt    22200
gggtttggtt catatatgta tatattaaag catatttcta tattattagc attgggaata    22260
tgggaaacag ggacttggtt tgaggatgca tagatcctgg gttgaaggat gagaataaag    22320
ttgaacagat gagaatgaaa atgcacaggc atccatcgcc atcaccacac acgtgctcta    22380
caaacaaaaa gtttgtgcag gccaggcgca gtggctcatg cctgtaatcc cagcactttg    22440
ggaggctgag gtgggtggat cacctgaggt caggagttcg agaccagcct ggccaacaag    22500
gcaaaaccct gtcactacta aaaaaacaca aaaattagcc agtgtacacc tgtaatctca    22560
gctactcagg aggcttaggc aggagaatcg cttgaacctg ggagagggag gttgcagtga    22620
gccaatatca cactactgca ctccagcctg gcaacagag tgagactcca tttcaaaaaa    22680
aaaaaaaaag tttgtgcaaa caactacccc accctcacct ccttttctct catagattta    22740
tagtattcct ggttcattcc tatttaattc tccttattaa agaagagat atatgtatat     22800
acacacacac acacacacac acacacacac acacatacat atatatatgt ttattgttat    22860
cttcacatgc tggttttatt tgaacataaa tgactgtttt gaaatcgagt cttgcaattt    22920
catttatatg cctttatttt caattttag attaaaaggt tttacgtcct gttgactaaa    22980
ttctgtacat cagaatgttg gccaaaaagc agatggcgtt tagatttgga gaggatgtgg    23040
```

```
gtaactctat gacccatccc tgccgtcagc tgtatctgtt ttcaggcata gccagtccta   23100
aagccttatg tggagccttg ggcgggggaa gaggatcaag agaacaaatg atggtctccg   23160
ccttggctag cccctgtgtg tctgcctctg ccactgggga cctctttctg agggcaggtc   23220
aaggacacat gtgccgcctt cacctgcctc tttcagttct gacagccatc tgcttagcac   23280
agggctactt gccagttcct acctgtttct gcctctgacc cacaactgct atgttaccgg   23340
tacaaaaccc cccacacaca gtgcccctc ggtgagccct tgttaggcct ggcctgggct    23400
tcctagcact tctttccttt aactcccacc cctggccgtc acagtcctgt ggcttccatg   23460
tcatatgctg gacctttggt ctctaggatc tccccggcca ggtgaagaag gaactaaagg   23520
ccaaaggatc ccgagccttg agctgctaat gatgtagggg ctgggtcagg aatgtaagt   23580 gggtacctat atatcataat ttgtaaaatg actttatagg catatactta catcaggatg   23640
tcttacataa tatgtatatt atataaagtg gtgattaatt ggtaaacaca atgaacatca   23700
ctgtttagat actgaagaac ctaagacaat aagtacctaa atagttatgt tgaaaattct   23760
gtgaactcta gcctttataa ctaattacta cagaatgtaa cacttacggc cgggtgtggt   23820
ggctcacgcc tgtaatccta gcactttggg aggccgaggc agttggatca cttggggcca   23880
ggagttcgag accagcctgg ccaacatggt gaaacccat ctctagtaaa atacaaaaa    23940 tacctgggcg tggtggtgta cgcttgtagt cccagctact catgaggctg aggtgggggg   24000
attgcttgaa cccaggagga gagtctgca gtgagccgag gtcatgccac tgtactcaag    24060
cctgggcaac agagcaagac tctttctcaa aaaaaaaaa aagaatgtaa tatatatctt    24120
taaatatgca aattaatgtg atatataggg tgtatttggt tatagcatat aattcaacta   24180
tttatgcagt agtttataac tagttgctaa tacagtgtag acatccatca cagtctaaag   24240
aagactggaa atatgttgat tgcttagtgt tcaatggaaa actttttttt ttttttgtc    24300 taggaatgag gggcagtgcc acatagtaca aaaagcattt cacttggagc caaaattctt   24360
tggtttaatt tttattgaaa ataacatgta tcgtgccatg ctctggggtg tgctcagtac   24420
tagctgagat gattcctagt ctgagctccc actccactcc accctcccca ctgccctggg   24480
agcatagaga ctagagcatc actgactggt acgcaaggtg tgatggtcgc agcatgcatg   24540
ggtgttgtac acgcacaaaa gggaggcatc tgaccagact gagggatcgg ggggaacttc   24600
ttagaggtgg catctgaacc aattatgcaa ataagtccac tcagtgaaga aggggcaga    24660 acttttgag cagaaggaac agtaagtgga aaggcacaaa ggaagaatga acatccagtg    24720
tagtgaaact gaaggcagct gcattttggt ggggctggtg agtgaagctg ctctccctct   24780
ccaggcattg atttcttcag gtgtcaactg gggagatgga catggtcatc tctgagagcc   24840
aatacagttc aagtactgtc ccaaatctgt aaccgattat tagaaactgg gaagagtgac   24900
atggtcatct ctgagagcca gtccagttca aacactgtcc caaatctgta actgattatt   24960
acgaactggg aagtgacatg gtcatctctg agagccagtc cagttcaaac actgttccaa   25020
atctgtaact gattgttacg gactcctgtt gaggaagaag aagtaaaaaa accctgcatc   25080
caagatgagc ccccacttcc acgaagctcc cttccagtca gtttcatcat tggctctact   25140
gctctgatgg attttcaga acgttctgtt ttccccctgt cttttttctag gctgttcttg    25200 ctggagattt aattctttct gcagcatcta tagctctggc acgaattgga aatacaactg   25260
ttatatctat tttaacccaa gttattgaag atttggtgcg tggtacgttg attctgattt   25320
ttcttctttg ttattcaacc ctggtgttta gccaggcaat aaagccacct ctcaaatgac   25380
```

```
tcctttcctt ctttataggt gaatttcttc agctcgggtc aaaagaaaat gagaatgaaa    25440
gatttgcaca ctaccttgag aagacattca agaagaccgc cagcctgata gccaacagtt    25500
gtaaagcagt atgtacgttc tgtctttctt caagttaaag cctcatagct cttttttggg    25560
agctaatttt cctagaaaat atttcggtga agaatcttaa aatagtaccc aaaaatccca    25620
agaggttaat gaggaaaaga atgacatccc caaacaatag aggacttctg ctgtgttttc    25680 attttttgcca tcttcttttg gtatgcaggc gttgactttt catctttcct tcccaagaat    25740
tcaatcaaaa taagctttcc cgcaccttcc ccaatctgat tgccaaactg tatcattttg    25800
aacaatttat cataatttct ctaatgattg atatcacaca cactcttct gacacttcac     25860 cttttagaaa tgaagtgctc tgttctttaa tataatattt actcaggaaa agatatctgt    25920
tagattgtac tagcattcta tgaacttttt tttgtttttt tgtttttgt gtttttttga     25980 gacagagtct tttgctgtgt ggcccaggct acaaagcagt ggtgtgatct tggctcacta    26040
caacctccac ctcccaggtt caggcaattc tcctgcctca gcttcctag tagctgggac     26100 cacaggtgtg cgccatcaca cccagctaat ttttgtattt ttcataggga tggggttttg    26160
ccatgttggc tgggctggtc tcaaactcct gccctcaagt gatccaccca ccttggccct    26220
gcaaagtact gggattacag gcatgagcca ttgcacctgg ccaatacatt gcacctggcc    26280
aatccttcta atatttttac atgaaatata aacaagtcct atttcttcag agtacaaatt    26340
gagtataagc cataactgtt tttccccttg ctttctccct ccctccgctg tgcatacaca    26400
tgtatacatt tttttttttaa tgagtaatac ctttaatccg tagacaaatg tgtggtattc    26460
atcgttagtc caagaatgaa aagcagtctc tccatagaat tgtttatctg cccatctcta    26520
agcctgacag atacacagag acaaaacctg gacaaatgac attcccatgt aattacagcc    26580
acaaaataag gaagacctgt aagggtcgca tgtcaattgc tgtcatgata gactcctaac    26640
ataattaaca ggtaaagaga gcttttgctc agacctctca gatgaaaaag tctcttgctg    26700
ttagtgtctc tgttttgaaa agtgtcaaga aatgtataat tgcaaggcag aaaagaatga    26760
ggacaatctt ttcttcctaa aaagacctaa tagaaacttt aaggaatgtg aattatgtag    26820
aacatgctag ccacagtctc gaccactttt gtctttttat taaaagggct attatgtttt    26880
tatttccaag aaattatgtg ggtttttttt ttaaagtgag atggaagaaa gtatagacac    26940
gagatgctaa ataagagaat agcctatttt aagtgggtgc tctaacactt ttacagtaat    27000
cctttacata ttatcatgcc cttgatggcc caactctccc tgaaggtcag gatccatcct    27060
cttaacacat tagggtgcct taatattact tactaatatt tatccttaag aggatgtgtt    27120
aagtgaggct cattgataat ttcacaattt gagactgcaa acttagaagc attagcatgg    27180
tcaggcaagg tggctcacac ctgtaatccc agcatttagg gagactgagg cggaaggttt    27240
gcttgtgacc agaagttcaa gaccaaccta ggcaacatag caagatcccc atctctactt    27300
aaaaataatg tttaaaaaat aaagtcttag aagcattagt agtagtgaga ctattggaat    27360
tggaaacacc aagacttact gtctgcacca tgcagacatc ctgcaggcac ggggtggggc    27420
ggcaccaaat tggagctagc acagaaattc actcagtgat ggaagcttac aaagggtcca    27480
aagaaatgga cctgagtcat gatagagagg tttccttgtg gtcactgttt tctgtttaag    27540
aagccaaaga taatgcacag gaattctttt ataaagatat gcacctcatt cttcaaagat    27600
tagcagctga acgaacagtg aacatgttaa cgtggctgga cccttaataa aaatgaaatg    27660
tttcatgctg cccactaggg ggcatgctgg catcgtccca gcactacctc cttttcatgt    27720
ggtttattcc taaactccac agctcttaga ataataaagc aaaatgatag tgtgagctat    27780
```

```
ttgaataaaa gtttctatat ttaagtgcct atgggtggaa atattccaga ggtgttatgg    27840
attcaaaatg ctattttta cgtactcttg gtatttaaaa tgcaaagcca tgcgagctcc    27900
aaataaatgc atgcaaagca aattagacac accaaaaaga ggggaggagg agaactgaaa    27960
gagcagaatt attacagaag aagaactaat gggattgcaa aatgtattga gaattggagg    28020
gaaacttaca agctgcattc tactaaggat accatttctt catctccctt ccttttttta    28080
gtgaaaataa tattaaaatc taagagaggg ctgtctaggg ggattgtttt gtgattgact    28140
gatattaaaa tagaatccat tttaggccgg gcacggtggc tcacacctgt aatcctaaca    28200
ctttaggagg ccgaggtgag tggatcactt tagtccagga tttcaagacc agcctggcca    28260
acatggcaaa accccgtctg tactaaaaat acaaaaatta gccgggcgtg gtggtgcacg    28320
cctgtaatgc cagctacttg ggaagctgag gcaggagaac cgcttgaacc cgggaggtgg    28380
aggttgcagt gagccaagat cactccactg cattccagcc tgggcaatag agcgagagtc    28440
tctcaaaaaa aaaaaacaa accagaattc atgttattat caaaagatga cttatttatt    28500
tacatactta ctcacttgca aaatacattt tgtactcatg caaaatacat tttgtagctt    28560
actaataaag acagtggctt gtttcccagg aaatctggtg gaaatgagac ctgagaggtc    28620
agagggcctg tccagttgtt gttaagccag acagtagctg agttgagact tgaacccaga    28680
gctgggtatg gtaatcctgc cttgtttctc tctctctctc tctcttttt tttttttttc    28740 tgaatttcta ttttctccag ggctgcttgt ggcctggaat taatgggctc tcttcctatt    28800
acttgatttt caaagcctca gagtaccact acagaattgc atattgtggg tcacattagc    28860
agaacactct tttttttttt ttttaattca ttttttgag atggagtctc gctctgttgc    28920
ccaggctgga gcgcagtggc atgatctcag ctcactgcaa cctccacctc ccaggttcaa    28980
gtgattctcc cacctcagcc tcccgagtag ctgggattac aggtgcacac caccacatgc    29040
cacacctggc ctcttttttt tttacaatat tcatatctat ctataggcct cattcagatc    29100
ttgccagttg tgaactgtta taacgaaagg gaaaacatat ttttctgttc cagcatccag    29160
tccaggattt cacgttgcat tttgctgtca tgactctgta gtctcttgtc atctagaaca    29220
gtctttcttt gcctctcatt accttggtat ttggaagagt gcaggccagt tatgttgttg    29280
agcctctcag tcgggcttct ctgatacttc tcaagattcg atccaggtta tgaatatttg    29340
gcaggaatac cacaagagcg gtgctgtcct cagctcctca taccaggagg cgcgtgctgt    29400
cttgtctgtc ccgttactgg tgatgcatgc ctggatcgct tgattaggat actgtcgggc    29460
cgggcacagt ggctcacgcc tgtaatccca gcactttgga aggccgaggt gggcagatta    29520
cctgaggtca agagttcaag accagcctgg ccaacatggt aaaacccat ctctactaaa    29580 attataaaaa attagctggg catggtggcg ggcacctgta atctcagcac tttgggaggc    29640
cgaggcgggt agatcacctg aggtcaagag tttgacaagc gtggccaaca tagtgaaacc    29700
atgtctctac taaaaataca aaaattagcc gggcgtagtg gcaggcgcct ataatcccag    29760
ctactctgga ggctgataca ggagaattgc ttgaatccgg gaggcggagg ttgcagtgag    29820
ccgagattgc accattgcac tcaagcctgg gcaacaagag tgaaactcca tctcaaaaaa    29880
aaaagatact gtctgccagg tttcttcaat ctaaaattac tattttaacc tattttgggc    29940
aaagtatttt cagattatgt aaatattatt ctgatggttg tcaaatggct gttttttctat    30000 tttcatcatt tcttctatat cactcttcta caagaaagtt ggtatcctat ttttttttgtt    30060 attattattt cattctcaaa agagctgaag agttggtatt ccattgtaag gaagctctta    30120
```

```
actgtatggg ctcttggatt cttattttat tctgtatctt ttttttttt tttttttttt    30180
gagccagggt atcactctgt cacccacgct ggagtgcagt ggtgcaatct cagctcactg    30240
caacctccac ctcccgggct caggtgatcc tcccacctca gcctcctgag tagctgggat    30300
tacatgcggc tgccaccata cccggatgac ttttttgtat ttttagtaga gacggggttt    30360
tgccattttg cccaggctgg tctcaaactc ctggcctcaa gtgatcgccc acctcggcct    30420
cccaaagtgc tgggattata ggcgtgagtc accgtgccca gccatcttat tttattctgt    30480
agattataac actgtcatta ttttaatact caattatcca acgtatggcc agtaggggag    30540
gcccctttaac ctggctctgt gtcctccatc attttttcag caccccattt ctggcaggag    30600
atattcagcc ctgttattca ctgttctcca aggagcccac attccttttg gtggaaaatg    30660
gtgttaagaa accagaattt gagtactggg tgtcatcgtt tctagaccca ctcaatggac    30720
agagctagga aatacatgta tgtattatat gtaatgtagg tagatacgtg tatatctttc    30780
tgtacccatc catacttatt caaaaccacg aggtatcaaa cagatagttc caaatccatc    30840
taacaccaca ggatttgtgg tttattccag gattccatct ttccatattt gtaaccccct    30900
tcccaaacag tgagagacct ggctcctctt ctccgcggtg tatttatttg cacaatctga    30960
gaatatacca taggagttta caaattcatg actcatatct ctgtgaaaaa caaacccagt    31020
agctagaatt cagtatttat cattcctttt gtcttgggcc tgaggataat agaatcaaag    31080
cactgttcaa aagttacctt tctctacgta tcagtgtggt tgtgttatta tttggaatat    31140
attaacccat ttatgcctag tgttccatta ttggaatgct aagcttgtgg agttatttct    31200
atcctactgc tcaaggtcat taccaaggtc tgattttca caaaacaaat ttgcaacctc    31260
cagcataaat gggttaatag ttggttcctt ttttttttt tttttttttt tgagacggag    31320
tcttgctctt tcgcccaggc cggagtgcag tggcactatc tcagctcact gcaagctctg    31380
cctcccgggt tcacgccatt ctcctgcctc agcctcccga gtagctggga ctacaggtgc    31440
ccgctaccac gcccggctaa ttttttgtat ttttagtaga gatggggttt catggtgtta    31500
gccaggatgg tctcgatctc ctgacctcgt gatccgcccg cctcggcctc ccaaagtgct    31560
gggattacag gtgtgagcca ccgcgcccag cctagttgga ttcatttta ttccacttta    31620
gggattccct ctcattcttg ctgatttcgt gttttggttt tgagcgtttt gttattgttg    31680
ctgttgtttt gaatgtttga aacaacgtgg ctgggcacag tgtctcatgc ctgtaatcct    31740
agcactttgg gaggccaagg cagatggatt gcttgagccc aggagtttga gaccagcctg    31800
ggcaacatgg cgaaacctct gtctacaagg aatacaaaaa ttagctgggt gtggtagtgc    31860
acacctgaag tcccagctac ctgggaggct gaggtgggag gatcacctga gccctgggag    31920
gtcgaggctg cagtgagctg tgatcacacc actgcactcc agcctggcaa cagagtgaga    31980
ctctgtctaa aaaataata ataataaaaa aataaaaga cattaatgta gctccaaaag    32040
tcagaactat acaatacagt aactctccct tttgccctgt ttcttcccc tacccccttg    32100
taggtaagca gtctcgttca cttctggttc ctccttcctg ggtttcgttt agcacaaaca    32160
ggcagacaca agtatgctat cttcccttct ttctcacagc aagaagtagt accctagact    32220
actctgcttt ccttttgcat ttcttcagtt aacaatttat taggaaaatg attccacatt    32280
ggtttgtagg atcttcctca tttttaaaac cactgtatca gggctgggct tgtaatccca    32340
gcactttggg aggctgaggc ggccgaatca cgaggtcagg agttcgagac cagcctggcc    32400
aacatggtga aacccttctc ccactaaaaa tacaaaaatt agctgggcgt ggtggcacac    32460
acctgtaatc ccagcacttt gggaggccaa agcaggcgga tcacttgaga ccagagttca    32520
```

-continued

```
aggccaggcc ggccaacatg gtggaacccc atctctacta aaagtacaaa aattagccag    32580
gtatggtggt gggtgcctgt aatcccagct actcgggagg ctgaggcaca agaatagctt    32640
gaacccggga ggtggaggtt gtagtgagcc aagatcacgt cactgcactc cagcatgggc    32700
gacaaagtga gactccatct caaaaaaatt aataaataaa taatttaaaa atttttttaa    32760
aagcctctgt atcagatccc attatgtgga catagcatgg tttattcagc caatcttcta    32820
tacatgggca tttaggtttc cagttttaca attacaaaca ctactgcaag ggctgatcgt    32880
gcataaacct attttgtgt tgtgagagga gtgcctgcag ggtgaattta ggggtaattg     32940
cacatgtggt tttgttaggc accaccagat ttccctctgt tgggtctgta ccagtatgtg    33000
tttccaccag cagcttttca gaacctcttt tcccacagcc ttactaacta aatgtgccat    33060
tacacgcttg agtttttgcc agtccagtag aggagaatgt attgcagtgg agttttaatt    33120
tacatctctc cttctgagt gaggtggaac atttttcaga tgcttaaggg ccatttattt     33180
atttgtttat ttatcggagt ctcactctgt cacccaggct ggagtgcagt ggcacgatct    33240
cggctcactg caacctccgc ctcccaggtt caagcaattc tcctgcctca gcctcccaag    33300
tagctgggat tacaggcgtg agccactgcg cccagccctt cccagtctcg ttgagacgtg    33360
gcttgtaagg atgtgatgca aggtgtgaac cttccccaga aagaagtgca tacgcacagc    33420
acagcctggc tgcagcatct gcttcaaaca aaacagttag ccgagctcca cttctcttga    33480
cttaatcatt cttcatgctc cacccatttc cggaaagatg tgaggcatcc ctctgatgct    33540
gagcgcaagt ctgtgcacct ctttgccttc ttgtatgttg tgctatgttg cgtccaattt    33600
gtggcagttg ttttctgttt tcctgctaca gatctaggca gtactgacct gggatgggga    33660
agcaggactc tctggcatgg tctttatgct accccaggga aatctgggat agttgaaatc    33720
tgagcagtaa tgtcccttcg ccatgtgtca ggcagaagct gcccactaaa taagctctgt    33780
tcagcatgtg tgggcacaga ggggacagtg cagacagact gcagctttat gcttacttgg    33840
acacattcct tgacctcttg gaggttctat tttgttgccc agcatagaag cagcactcct    33900
gtgttgaagt gatgaagaga acagtgtctg gagccagacc atgtggatga aattcaggtt    33960
ccagcgtgtt ggagccatgt aatgcctggt accgtctgtg tctcagtttc tcgaacttca    34020
taagtgactt aagatgtgag aactctcaga acagtgccta gcacatagtg gacgctcaga    34080
aattgttagc ttttatcatc accaaccaca taatccatat ttgtgggata ttgtgaggtt    34140
taactcaaat catacaaagt gttcatcata tgtgctccac acattttaat ccattaaaat    34200
gttcactaac agatttttag gccgggcacg gtggctcacg cctgtaatcc cagcactttg    34260
ggaggctgag gcaggcggat cacctgaggt caggagttcg agaccagcct gaaacccgt     34320
ctctactaaa aatacaaaaa ttagctgggc gtggtggcat acggaggttg aggcaggaga    34380
atcgcttgaa cttgggaggt ggagattaca gtgagcccag atcgtgccgc tgcactctag    34440
cctgggtgac agagagactc cgtctccaaa aaaagaaata gatttttaga aaatctttca    34500
cttttcagga agaaagctta tagtctctgt ggctctgtgt tgaggaaaca gcattaatct    34560
cactacagga gactgcttca ctatcagtta tttctacgtg gaaatatctt gattcccagt    34620
atcattctgt cctgagccca gcacatccca ggctgcccaa atcttgccat gctctccttt    34680
gagccaagct gatcttagct tctctcgaaa gtttctgaat tgtcccccat atggtctccc    34740
agactcttca gttgaaaaaa ggagccctcc ctgacagccc aggggtcggt gcctgctcat    34800
gggaaggtgg ttgctgttga aagcagttat gagcttactt tcactcaac tcagtggcca     34860
```

```
cctgacccct tatggtgcat gcaattttac catgtactta tggccaagca ctacatagtc   34920
aacagacctc attaagttgt caaaaagcat tctcaggctg aggacgttag gcaacctggc   34980
tttagttggc agaggtgcgt ggacactgcc aaggctccta tttctggttc cagtggatga   35040
ggtggaggag gattatttgt aataatagca acagccagtg tgcggtggct cacacctgat   35100
aatctcaacg ctttgggagg tggaggtggg aggatcacga gcccaggagt ttgaggccag   35160
cctagacaac atggtgagac tccatctcta tgaaaaaatt aaaaatcagc tgggtgtggt   35220
tgcgcgtgcc tgtagtccca gctactcagg agactgaggc ggaaggaacc cttgagccca   35280
ggagttcaag gttacagtga gctatgatcg caccactgta ccccagcctg gcaacagag   35340 tgagacccta tttctaaaaa gagataataa tagcaaacac acattgagtt ctaaccaggt   35400
gccaggcagt atactgaggg cttaaatgca gcatcatgtc tgtttctcac agcaacccta   35460
caaggtaagt gcttgtgatt tctacattgt acagatgagc aagagagatt cagtaacatg   35520
ccgaggtctt gtagagggca caaatgcagc cccacagtct cacagcagag cccgcagcac   35580
tgcaccacac tgacgcctga gcaaagttca ctccctgact ggagagccac agaggcacga   35640
ccgaaggtca ggggacaggg tttcctagca tccgcgagcc ttacagaaag gcaactgtgc   35700
agtgctccag ctggctttct catggagagt caacagagac atttccctc cagtagaaca   35760 cagaccgtct ctcccctccc ccttgttggt tttacccagg ctttgttttc tgaaaatgtg   35820
gctgggcctg cttaacatgc ttagcagggc actgggaaat gcacttcagt ggccggtgcc   35880
agctagcttt ttggagtttt aaaaagactt tcagaagtct tatttctccc ccattgaaag   35940
gagggaaaag ggttttttata cagttacttc ttttgagaga aatgtggaaa cagtgggacc   36000
agtgaagttc cttccgataa tgaaagagcg atatctgtgt ctgaagcagg aggcttgaga   36060
tgatttttat ggacacacca agaaataact gcattcagaa acaggtgaaa ttcccaacga   36120
tgatgaaaag aaaggactac agatgggaaa attgtgtgtg attacattag tatctcttcc   36180
tgaaatgagg gatacattga tagagatgat taaagccaac agtaatcggg ctagcttgcc   36240
gagtgctaga agtcagtatt tcacagatgg gggtccgttt cttttgcatg tcaagaaggt   36300
ttacttagca tgttaccagc agaactagtc cagttgtagc tcagttttc ctaagcagtg   36360 ggaaaggctg cttatcctgt ctgaaagcag gggttggaga aggagaattt tcttagaatt   36420
taacaacaca atctgagact gaaattcttg actggaaatg cggttttgta catgcttggt   36480
gtccctctga tgtcagcatc tcctgagtgt gtataatcta gccccgctgc ctcctatttt   36540
aaggaattcc ttcagccagg ggtcagctgc tttgttgctg cctggaagca gcttatctca   36600
gaatgctctt tctgtttcag gtctctgttc taggatgtcc cgacccagtg gtgcatgaga   36660
tcgcctatca gtacggaaaa aatgtaggaa tagcttttca ggttagtatg cttttttattt   36720 gtaagaatgg tggcgtagtg atacagtcag cattctcccc tagtgtgtaa tcgtcaaaat   36780
agtaagaacg atggcagcag tgttggcatg gcggtgctcc ttacatccca ttttcctttt   36840
tgccagctaa tagatgatgt attggacttc acctcgtgtt ctgaccagat gggcaaacca   36900
acatcagctg atctgaagct cgggttagcc actggtcctg tcctgttgc ctgtcagcag   36960 gtaggtttta caactccct ttgacacatc actgcatagc cccacagaac tgatgtcccg   37020
cggcacagct gatgggaaga ttgcataaag gaatagatgg gaaggcattc agataagaga   37080
tcacaggtct gcatttgatc ctggctgagt gagatgttgg ggctggtcat ttcaccttgc   37140
taagactgtt tccttatctg taaaattgag aagatcacct ttctcccagg gtggttgtga   37200
ggattagcta agatcctatt tgagatcttt gtgtcttgtg gtgtgccata ggcatttgag   37260
```

```
gtagcatcgt gattatttcc atatattttg gccactggca aagtgaacgg tttctaagtc    37320
ttgattatag gactggactt tggtggtcct cagagcccct aaaaggcat aggaagcatc     37380 aagggcctcc aagcataaga aattctccgg ttctagaagt ttaatgagac tctgctgctc    37440
tgagagaggc tttagaacct cggccattgc ctcaaaatgt caggaagtca gtggagtgca    37500
gtagacccac atagttcctt cttctccgg attgagggac tgagtccccc ttaatgtgaa     37560
tgaaaggctt aggaagcttc aaagatgttc cctcgactga caaagcagac attctcacag    37620
cctcctccag accctgccac atggcttgtg gctgtactga atgttacttg aaataagtga    37680
gacattagct ggtgttggaa catctcgtta atagattttc atcttagtag tatttaattt    37740
gttatgttgc aaagcagtaa gatgttcatc accgtgccat gaaattcaac attagctctt    37800
tggtgtaaaa ttatagtaac ttttggtctt tcagagattt gcctctatt ctgtcttcac     37860 gtttacaaag gtcagtcatg tcctccataa aattcagtga ttccactgtg atacagaaac    37920
cacggccctt gcttttggtg ggtttctgat tggagagagg aaaggtcatc tttcacccac    37980
tatctagcat agccattggc agcatgattc ttcccagggg aggctgacgt tctgggtggc    38040
tggaccaggc tactttggca gcttgctaag gctatgaatg gagatgttgg ggtactcggt    38100
aggaacaccc gccctcatta ttacaaggct tccatcctct caaactttgg aggctgaggt    38160
aagaagtgaa aggtatgctg taaataggtc ctctctccca atgaggctta cttgccagcc    38220
caaaatcaaa gagtataata catgtgccca gttttgacaa aaatttataa aacctccttt    38280
tgtacattaa ggcaagagtg aggaacattt gagccatgta ggtgttatgc tggggattag    38340
aaaaatgagg cactggctac cagtaaccta tataactgcg aacattactt ctcagatact    38400
tgttagtaaa catgagtgaa ggaaagcaag atggactgag tgtgctgaaa tccagctagc    38460
ttggtaaaga ttcctttacc taggctcaga ttatcaggat aaaaggaaaa agcctttttc    38520
cctggagaag tctatgagaa agttttggtt gctctatttg taaaaatctt caaattgtta    38580
agtacttgtt atgaaccccca ggatactaag ttaccggttg agtcctactt aaaccttaag    38640
gtgactgggt gagaggaggc tggcctcttc ggactgtgtt tcactctgaa tatatttcag    38700
aagaaactaa cttactttcc cctacacaca caaaggagta atggctatct ctgctttcat    38760
atatagtggg ggaaagggga aatggacctc tgcatagtat ctgtcagtaa tctacaagag    38820
actgaaaaat gctggttagg cggtggctca tgcctgtaat cccagcactt tgggaggctg    38880
aggcagttgg attatgaggt caggagttca agaccagcct gaccaatatg gtggaaaccc    38940
cgtctctact aaaaatacaa aaattagccg ggcctggtgg tgcatgcctg taatcccagc    39000
tactcgggag gccaaggaag gagaatcctt gaacctggga ggcagaggtt gcagtgagcc    39060
gagactgcac tccagcctgg gtgacagagt gagactccgt ctcaaaaaaa aaaaaaaagg    39120
ctggttaaaa aaagcaagca aaaggaaaaa aaaagattac tgtacccgaa gccatggttt    39180
tatgtgtgct ttgctgggaa atcccagtca tgaggcacct actcatgctc accagacagc    39240
agtgttctca tctgcccata aggcagtgag ttgaaaaggc acattgcagc ctcagaaaag    39300
ggaacacaga atggagtcca agcaggaagt gactctggac aggactcatt tcaaaagtag    39360
actgatgttt ctgtcttgtg gcacatgggc cagaagttag ccaagtatgt atttataagt    39420
tgccttctaa taaaacagca aggttaggct cttttgtgga atacactgta aaacaagaga    39480
ttcttagcaa gaaatgtgtc aaaagatata tgggactaag attaattcag gtaaaacaa     39540 gttccaaaaa taacgtaaga atatgcaata tctccactta atgaaaatgt gttttagtt    39600
```

-continued

```
tacaaaggat tctttcatac attatctcta atctcacaac tcctctttgt ggtagatatt    39660
atggtgttta ttctgcaagt aagaaactga tgcccaaacc tcgccaaaat taaacatctg    39720
gtaaatggca cagcagggaa ctgaacaagt ctaagaccag tattcatttt attacatcat    39780
acatagtgtt attgccactg gtaatgctga gaagttagta gctatgatac cacacaggcc    39840
ttcccacaga gcaggtaact aacccacctg ggcactgacg atactcaaag aatcatctct    39900
gtgtcatgtc tttgctattg taaacaacat acctacttgg tggagtagtt ctaagacgtc    39960
tgtaatcctt tcccttttggt ag                                            39982
```

<210> SEQ ID NO 4
<211> LENGTH: 308
<212> TYPE: PRT
<213> ORGANISM: Homo sapiens

<400> SEQUENCE: 4

```
Ala Gln Ala His Arg Gln Lys Gly Leu Asp Leu Ser Gln Ile Pro Tyr
  1               5                  10                  15

Phe Asn Leu Val Lys His Leu Thr Pro Ala Cys Pro Asn Val Tyr Ser
             20                  25                  30

Ile Ser Gln Phe His His Thr Thr Pro Tyr Ser Lys Thr His Ser Gly
         35                  40                  45

Glu Lys Tyr Thr Asp Pro Phe Lys Leu Gly Trp Arg Asp Leu Lys Gly
     50                  55                  60

Leu Tyr Glu Gly Ile Arg Lys Glu Pro Leu Ile Ser Thr Thr Glu Leu
 65                  70                  75                  80

Lys Glu Ile Ser Glu Tyr Tyr Phe Asp Val Lys Gly Lys Ala Phe Arg
                 85                  90                  95

Pro Ile Ile Val Val Leu Met Ala Arg Ala Cys Asn Ile His His Asn
            100                 105                 110

Asn Ser Arg His Val Gln Ala Ser Gln Arg Ala Ile Ala Leu Ile Ala
        115                 120                 125

Glu Met Ile His Thr Ala Ser Leu Val His Asp Asp Val Ile Asp Asp
    130                 135                 140

Ala Ser Ser Arg Arg Gly Lys His Thr Val Asn Lys Ile Trp Gly Glu
145                 150                 155                 160

Lys Lys Ala Val Leu Ala Gly Asp Leu Ile Leu Ser Ala Ala Ser Ile
                165                 170                 175

Ala Leu Ala Arg Ile Gly Asn Thr Thr Val Ile Ser Ile Leu Thr Gln
            180                 185                 190

Val Ile Glu Asp Leu Val Arg Gly Glu Phe Leu Gln Leu Gly Ser Lys
        195                 200                 205

Glu Asn Glu Asn Glu Arg Phe Ala His Tyr Leu Glu Lys Thr Phe Lys
    210                 215                 220

Lys Thr Ala Ser Leu Ile Ala Asn Ser Cys Lys Ala Val Ser Val Leu
225                 230                 235                 240

Gly Cys Pro Asp Pro Val Val His Glu Ile Ala Tyr Gln Tyr Gly Lys
                245                 250                 255

Asn Val Gly Ile Ala Phe Gln Leu Ile Asp Asp Val Leu Asp Phe Thr
            260                 265                 270

Ser Cys Ser Asp Gln Met Gly Lys Pro Thr Ser Ala Asp Leu Lys Leu
        275                 280                 285
```

```
Gly Leu Ala Thr Gly Pro Val Leu Phe Ala Cys Gln Gln Phe Pro Glu
    290                 295                 300

Met Asn Ala Met
305
```

ISOLATED HUMAN ENZYME PROTEINS, NUCLEIC ACID MOLECULES ENCODING HUMAN ENZYME PROTEINS, AND USES THEREOF

This application is a Division of U.S. application Ser. No. 09/820,924 filed Mar. 30, 2001, now U.S. Pat. No. 6,555,351 issued Apr. 29, 2003.

FIELD OF THE INVENTION

The present invention is in the field of enzyme proteins that are related to the trans-prenyltransferase subfamily, recombinant DNA molecules, and protein production. The present invention specifically provides novel peptides and proteins and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the trans-prenyltransferase subfamily.

The present invention has substantial similarity to trans-prenyltransferase (polyprenyl pyrophosphate synthetase). Trans-prenyltransferase synthesizes the side-chain moiety of coenzyme Q, taking place in microsomes of Golgi system. Trans-prenyltransferase, a ubiquitous protein, is a member of the coenzyme Q biosynthesis pathway, and a very important enzyme involved in biosynthesis of polyprenyls and coenzyme Q. CoQ synthesis is also dependent on trans-prenyltransferase activity on the level of intracellular substrate concentration. In addition, CoQ level may be regulated in blood as well as in various tissues. Thus, the enzyme of the present invention may be a potential drug target for anti-cancer treatment. For a review related to trans-prenyltransferase, see Appelkvist et al., Mol Aspects Med 1994;15 Suppl:s37–46; Rotig et al., Lancet Jul. 29, 2000;356 (9227):391–5.

Enzyme proteins, particularly members of the trans-prenyltransferase subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the trans-prenyltransferase subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the trans-prenyltransferase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver.

DESCRIPTION OF THE FIGURE SHEETS

FIGS. 1A–1B provide the nucleotide sequence of a cDNA molecule sequence that encodes the enzyme protein of the present invention. (SEQ ID NO: 1) In addition, structure and functional information is provided, such as ATG start, stop and tissue distribution, where available, that allows one to readily determine specific uses of inventions based on this molecular sequence. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver.

FIGS. 2A–2B provide the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIGS. 3A–3U provide genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. 57 SNPs, including 8 indels, have been identified in the gene encoding the enzyme protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the trans-prenyltransferase subfamily. Utilizing these sequences, additional genomic sequences were assembled and transcript and/or cDNA sequences were isolated and characterized. Based on this analysis, the present invention provides amino acid sequences of human enzyme peptides and proteins that are related to the trans-prenyltransferase subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the trans-prenyltransferase subfamily and the expression pattern observed. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known trans-prenyltransferase family or subfamily of enzyme proteins.

Specific Embodiments

Peptide Molecules

The present invention provides nucleic acid sequences that encode protein molecules that have been identified as being members of the enzyme family of proteins and are related to the trans-prenyltransferase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology*, 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of. 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. As indicated by the data presented in FIG. 3, the map position was determined to be on chromosome 10 by ePCR.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. As indicated by the data presented in FIG. 3, the map position was determined to be on chromosome 10 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more filly described below.

FIG. 3 provides information on SNPs that have been found in the gene encoding the enzyme protein of the present invention. SNPs were identified at 57 different nucleotide positions in introns and regions 5' and 3' of the ORF. Such SNPs in introns and outside the ORF may affect control/regulatory elements.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver. A large percentage of pharmaceutical agents are being developed that modulate the activity of enzyme proteins, particularly members of the trans-prenyltransferase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the trans-prenyltransferase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Phannacol. Physiol. 23(10–11):983–985. (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO: 1, transcript sequence and SEQ ID NO:3, genomic sequence), or any nucleic acid molecule that encodes the protein provided in FIG. 2, SEQ ID. NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 10 by ePCR.

FIG. 3 provides information on SNPs that have been found in the gene encoding the enzyme protein of the present invention. SNPs were identified at 57 different nucleotide positions in introns and regions 5' and 3' of the ORF. Such SNPs in introns and outside the ORF may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 57 SNPs, including 8 indels, have been identified in the gene encoding the enzyme protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 10 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the T cells from T cell leukemia, B cells from Burkitt lymphoma, neuroblastoma cells, duodenal adenocarcinoma cell line, adenocarcinoma cell line, stomach, breast, whole liver.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme protein of the present invention. SNPs were identified at 57 different nucleotide positions in introns and regions 5' and 3' of the ORF. Such SNPs in introns and outside the ORF may affect control/regulatory elements. As indicated by the data presented in FIG. 3, the map position was determined to be on chromosome 10 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme protein of the present invention. SNPs were identified at 57 different nucleotide positions in introns and regions 5' and 3' of the ORF. Such SNPs in introns and outside the ORF may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the T cells from T cell leukemia, B cells from Burkitt lymphoma, neuroblastoma cells, duodenal adenocarcinoma cell line, adenocarcinoma cell line, stomach and breast detected by a virtual northern blot. In addition, PCR-based tissue screening panels indicate expression in whole liver. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme protein of the present invention. SNPs were identified at 57 different nucleotide positions in introns and regions 5' and 3' of the ORF. Such SNPs in introns and outside the ORF may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES$^2$ (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication Will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. PNAS 89:6232–6236 (1992). Another example of a recombinase system is the FLP recombinase system of S. cerevisiae (O'Gorman et al. Science 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. Nature 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo'and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide, wherein the amino acid sequence of said polypeptide consists of SEQ ID NO:2.

2. An isolated polypeptide, wherein the amino acid sequence of said polypeptide comprises SEQ ID NO:2.

3. An isolated trans-prenyltransferase, wherein the amino acid sequence of said trans-prenyltransferase consists of an amino sequence having at least 99% sequence identity to SEQ ID NO:2.

4. An isolated trans-prenyltransferase, wherein the amino acid sequence of said trans-prenyltransferase comprises an amino acid sequence having at least 99% sequence identity to SEQ ID NO:2.

5. The polypeptide of claim 1, further comprising a heterologous amino acid sequence.

6. The polypeptide of claim 2, further comprising a heterologous amino acid sequence.

7. The trans-prenyltransferase of claim 3, further comprising a heterologous amino acid sequence.

8. The trans-prenyltransferase of claim 4, further comprising a heterologous amino acid sequence.

9. A composition comprising the polypeptide of claim 1 and a carrier.

10. A composition comprising the polypeptide of claim 2 and a carrier.

11. A composition comprising the trans-prenyltransferase of claim 3 and a carrier.

12. A composition comprising the trans-prenyltransferase of claim 4 and a carrier.

13. A composition comprising the polypeptide of claim 5 and a carrier.

14. A composition comprising the polypeptide of claim 6 and a carrier.

15. A composition comprising the trans-prenyltransferase of claim 7 and a carrier.

16. A composition comprising the trans-prenyltransferase of claim 8 and a carrier.

* * * * *